(12) United States Patent
Weiss et al.

(10) Patent No.: US 11,339,395 B2
(45) Date of Patent: May 24, 2022

(54) RNA-BASED REGULATORY TECHNOLOGIES FOR MIRNA SENSORS

(71) Applicant: Massachusetts Institute of Technology, Cambridge, MA (US)

(72) Inventors: Ron Weiss, Newton, MA (US); Kevin J. Lebo, Weymouth, MA (US); Jin Huh, Watertown, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 239 days.

(21) Appl. No.: 16/528,697

(22) Filed: Aug. 1, 2019

(65) Prior Publication Data
US 2020/0040338 A1    Feb. 6, 2020

Related U.S. Application Data

(60) Provisional application No. 62/713,186, filed on Aug. 1, 2018.

(51) Int. Cl.
| | | |
|---|---|---|
| C12N 15/113 | (2010.01) | |
| C12N 9/22 | (2006.01) | |
| C12N 15/85 | (2006.01) | |

(52) U.S. Cl.
CPC .............. *C12N 15/113* (2013.01); *C12N 9/22* (2013.01); *C12N 15/85* (2013.01); *C12N 2310/113* (2013.01); *C12N 2800/80* (2013.01)

(58) Field of Classification Search
None
See application file for complete search history.

(56) References Cited

U.S. PATENT DOCUMENTS

| | | | | |
|---|---|---|---|---|
| 2013/0202532 A1* | 8/2013 | Benenson | ............... | G16B 25/10 424/9.1 |
| 2017/0159135 A1* | 6/2017 | Benenson | ............... | C12N 15/63 |
| 2019/0032141 A1 | 1/2019 | Weiss et al. | | |

FOREIGN PATENT DOCUMENTS

| | | | | |
|---|---|---|---|---|
| WO | WO-2016040395 A1 * | 3/2016 | ............. | C12N 15/85 |

OTHER PUBLICATIONS

Siuti et al. Nature Biotechnology 2013, vol. 31, pp. 448-453 (Year: 2013).*
Tyler Wagner, Dissertation, Boston University, retrieved on-line from http://open.bu.edu on Sep. 20, 2021, pp. 1-133 (Year: 2017).*
BME PhD Prospectus Defense—Tyler Wagner Boston University, retrieved on-line from http://bu.edu/phdpbin/calendar/event.php?id=cid=448&oid=0 on Sep. 21, 2021, p. 1 (Year: 2015).*
Johanning et al., A sindbis virus mRNA polynucleotide vector achieves prolonged and high level heterologous gene expression in vivo. Nucleic Acids Research. Jan. 1, 1995;23(9):1495-1501.
Kiani et al., CRISPR transcriptional repression devices and layered circuits in mammalian cells. Nat Methods. May 5, 2014;11(7):723-6. doi: 10.1038/nmeth.2969.
Lee et al., Programmable control of bacterial gene expression with the combined CRISPR and antisense RNA system. Nucleic Acids Research. Feb. 2, 2016;44(5):2462-73. doi: 10.1093/nar/gkw056.
Nissim et al., Multiplexed and programmable regulation of gene networks with an integrated RNA and CRISPR/Cas toolkit in human cells. Mol Cell. May 22, 2014;54(4):698-710. doi: 10.1016/j.molcel.2014.01.022.
Smerdou et al., Non-viral amplification systems for gene transfer: vectors based on alphaviruses. Curr Opin Mol Ther. Jan. 1, 1998;1(2):244-51.
Wroblewska et al., Mammalian synthetic circuits with RNA binding proteins for RNA-only delivery. Nat Biotechnol. Aug. 2015;33(8):839-41. doi: 10.1038/nbt.3301. Epub Aug. 3, 2015. PMID: 26237515; PMCID: PMC4532950.
Xie et al., Multi-input RNAi-based logic circuit for identification of specific cancer cells. Science. Sep. 2, 2011;333(6047):1307-11. doi: 10.1126/science. 1205527. PMID: 21885784.

* cited by examiner

*Primary Examiner* — Brian Whiteman
(74) *Attorney, Agent, or Firm* — Wolf, Greenfield & Sacks, P.C.

(57) ABSTRACT

Provided herein are genetic circuits and cell state classifiers for detecting the microRNA profile of a cell. In some embodiments, the cell state classifiers described herein utilize an endoribonuclease and a self-amplifying RNA molecule for controlling the expression of an output molecule. In some embodiments, the cell state classifiers described herein are encoded on a single RNA transcript, which is then processed to produce individual genetic circuits that function independently. The genetic circuits and cell state classifiers described herein may be used in various applications (e.g., therapeutic or diagnostic applications).

11 Claims, 4 Drawing Sheets
Specification includes a Sequence Listing.

SEQUENCE LISTING

```
<160> NUMBER OF SEQ ID NOS: 54

<210> SEQ ID NO 1
<211> LENGTH: 264
<212> TYPE: PRT
<213> ORGANISM: Pyrococcus furiosus

<400> SEQUENCE: 1

Met Arg Phe Leu Ile Arg Leu Val Pro Glu Asp Lys Asp Arg Ala Phe
1               5                   10                  15

Lys Val Pro Tyr Asn His Gln Tyr Tyr Leu Gln Gly Leu Ile Tyr Asn
            20                  25                  30

Ala Ile Lys Ser Ser Asn Pro Lys Leu Ala Thr Tyr Leu His Glu Val
        35                  40                  45

Lys Gly Pro Lys Leu Phe Thr Tyr Ser Leu Phe Met Ala Glu Lys Arg
    50                  55                  60

Glu His Pro Lys Gly Leu Pro Tyr Phe Leu Gly Tyr Lys Lys Gly Phe
65                  70                  75                  80

Phe Tyr Phe Ser Thr Cys Val Pro Glu Ile Ala Glu Ala Leu Val Asn
                85                  90                  95

Gly Leu Leu Met Asn Pro Glu Val Arg Leu Trp Asp Glu Arg Phe Tyr
            100                 105                 110

Leu His Glu Ile Lys Val Leu Arg Glu Pro Lys Lys Phe Asn Gly Ser
        115                 120                 125

Thr Phe Val Thr Leu Ser Pro Ile Ala Val Thr Val Val Arg Lys Gly
    130                 135                 140

Lys Ser Tyr Asp Val Pro Pro Met Glu Lys Glu Phe Tyr Ser Ile Ile
145                 150                 155                 160

Lys Asp Asp Leu Gln Asp Lys Tyr Val Met Ala Tyr Gly Asp Lys Pro
                165                 170                 175

Pro Ser Glu Phe Glu Met Glu Val Leu Ile Ala Lys Pro Lys Arg Phe
            180                 185                 190
```

Arg Ile Lys Pro Gly Ile Tyr Gln Thr Ala Trp His Leu Val Phe Arg
        195                 200                 205

Ala Tyr Gly Asn Asp Asp Leu Leu Lys Val Gly Tyr Glu Val Gly Phe
    210                 215                 220

Gly Glu Lys Asn Ser Leu Gly Phe Gly Met Val Lys Val Glu Gly Asn
225                 230                 235                 240

Lys Thr Thr Lys Glu Ala Glu Glu Gln Glu Lys Ile Thr Phe Asn Ser
            245                 250                 255

Arg Glu Glu Leu Lys Thr Gly Val
            260

<210> SEQ ID NO 2
<211> LENGTH: 792
<212> TYPE: DNA
<213> ORGANISM: Pyrococcus furiosus

<400> SEQUENCE: 2

```
atgcgcttcc tcattcgtct cgtgcctgag gataaggatc gggcctttaa agtgccatat      60
aaccatcagt attacctgca gggcctcatc tataatgcca tcaaatcctc caatccgaag     120
ctggccacct acctgcatga ggtgaagggt cccaaactgt tcacctacag cctgtttatg     180
gccgaaaaac gcgaacaccc taaggggctg ccttactttt ggggtacaa gaagggcttc      240
ttctactttt ctacctgcgt gccggagatc gctgaagcac tggtcaacgg actcctgatg     300
aatccagagg tgcgcctgtg ggacgaacgc ttctacctgc acgaaattaa ggttttgaga     360
gagcctaaga agttcaacgg ctctaccttc gtcaccctgt ctccgattgc tgtgactgtc     420
gtgaggaagg gtaagagtta tgatgtcccc cctatggaga aggagtttta cagtatcatc     480
aaagacgacc tgcaagataa ggtatgtgatg gcctacggcg acaagccccc atccgaattc     540
gagatggagg tgctgattgc taagccgaaa cggtttcgta ttaagcctgg catctatcag     600
acagcctggc acctggtttt tagggcctac ggaaacgacg acctgctgaa ggttggttac     660
gaggttgggt tcggagaaaa gaactccctg ggattcggca tggtgaaggt ggaggggaac     720
aagaccacaa agaagctga agagcaggaa aagatcacct tcaactctcg cgaggagctg     780
aagaccggcg tg                                                          792
```

<210> SEQ ID NO 3
<211> LENGTH: 29
<212> TYPE: DNA
<213> ORGANISM: Pyrococcus furiosus

<400> SEQUENCE: 3

```
gttacaataa gactaaatag aattgaaag                                        29
```

<210> SEQ ID NO 4
<211> LENGTH: 187
<212> TYPE: PRT
<213> ORGANISM: Pseudomonas aeruginosa

<400> SEQUENCE: 4

Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu His Gln Ala Leu
            20                  25                  30

Val Ala Gln Gly Gly Asp Arg Ile Gly Val Ser Phe Pro Asp Leu Asp
        35                  40                  45

```
Glu Ser Arg Ser Arg Leu Gly Glu Arg Leu Arg Ile His Ala Ser Ala
 50                  55                  60

Asp Asp Leu Arg Ala Leu Leu Ala Arg Pro Trp Leu Glu Gly Leu Arg
 65                  70                  75                  80

Asp His Leu Gln Phe Gly Glu Pro Ala Val Val Pro His Pro Thr Pro
                 85                  90                  95

Tyr Arg Gln Val Ser Arg Val Gln Ala Lys Ser Asn Pro Glu Arg Leu
                100                 105                 110

Arg Arg Arg Leu Met Arg Arg His Asp Leu Ser Glu Glu Ala Arg
            115                 120                 125

Lys Arg Ile Pro Asp Thr Val Ala Arg Ala Leu Asp Leu Pro Phe Val
        130                 135                 140

Thr Leu Arg Ser Gln Ser Thr Gly Gln His Phe Arg Leu Phe Ile Arg
145                 150                 155                 160

His Gly Pro Leu Gln Val Thr Ala Glu Glu Gly Phe Thr Cys Tyr
                165                 170                 175

Gly Leu Ser Lys Gly Gly Phe Val Pro Trp Phe
            180                 185
```

<210> SEQ ID NO 5
<211> LENGTH: 564
<212> TYPE: DNA
<213> ORGANISM: Pseudomonas aeruginosa

<400> SEQUENCE: 5

```
atggaccact atctcgacat tcggctgcga cctgacccgg agtttcctcc cgcccaactt      60
atgagcgtgc tgttcggcaa attgcaccag gccctggtag ctcaaggcgg tgaccgaatt     120
ggagtgagct tccctgacct ggatgagtct aggtcccgac tgggtgagag actcagaatc     180
cacgcatccg ccgacgacct cagagcactg ctggcccgcc cctggctgga gggcctcaga     240
gatcacttgc agtttggaga gccagccgtc gtgcctcacc ctaccccata caggcaagtg     300
tctagagtcc aggccaagag taaccccgaa cggctgcggc ggaggttgat gaggcggcac     360
gacctgtccg aagaagaggc acggaaaaga attcccgaca ccgttgctag ggctcttgat     420
ttgcccttcg tcaccttcg atcacagtcc accggacaac atttccgcct gttcattagg      480
cacgggcctc tgcaggtcac tgccgaagag ggcggattca cttgctacgg gctgtccaag     540
ggagggttcg ttccatggtt ctaa                                            564
```

<210> SEQ ID NO 6
<211> LENGTH: 28
<212> TYPE: DNA
<213> ORGANISM: Pseudomonas aeruginosa

<400> SEQUENCE: 6

```
gttcactgcc gtataggcag ctaagaaa                                         28
```

<210> SEQ ID NO 7
<211> LENGTH: 199
<212> TYPE: PRT
<213> ORGANISM: Escherichia coli

<400> SEQUENCE: 7

```
Met Tyr Leu Ser Lys Ile Ile Ile Ala Arg Ala Trp Ser Arg Asp Leu
 1               5                  10                  15

Tyr Gln Leu His Gln Glu Leu Trp His Leu Phe Pro Asn Arg Pro Asp
                 20                  25                  30
```

Ala Ala Arg Asp Phe Leu Phe His Val Glu Lys Arg Asn Thr Pro Glu
            35                  40                  45

Gly Cys His Val Leu Leu Gln Ser Ala Gln Met Pro Val Ser Thr Ala
 50                  55                  60

Val Ala Thr Val Ile Lys Thr Lys Gln Val Glu Phe Gln Leu Gln Val
 65                  70                  75                  80

Gly Val Pro Leu Tyr Phe Arg Leu Arg Ala Asn Pro Ile Lys Thr Ile
                 85                  90                  95

Leu Asp Asn Gln Lys Arg Leu Asp Ser Lys Gly Asn Ile Lys Arg Cys
            100                 105                 110

Arg Val Pro Leu Ile Lys Glu Ala Glu Gln Ile Ala Trp Leu Gln Arg
            115                 120                 125

Lys Leu Gly Asn Ala Ala Arg Val Glu Asp Val His Pro Ile Ser Glu
        130                 135                 140

Arg Pro Gln Tyr Phe Ser Gly Glu Gly Lys Asn Gly Lys Ile Gln Thr
145                 150                 155                 160

Val Cys Phe Glu Gly Val Leu Thr Ile Asn Asp Ala Pro Ala Leu Ile
                165                 170                 175

Asp Leu Leu Gln Gln Gly Ile Gly Pro Ala Lys Ser Met Gly Cys Gly
            180                 185                 190

Leu Leu Ser Leu Ala Pro Leu
        195

<210> SEQ ID NO 8
<211> LENGTH: 597
<212> TYPE: DNA
<213> ORGANISM: Escherichia coli

<400> SEQUENCE: 8
atgtacctca gtaagatcat catcgcccgc gcttggtccc gtgacctgta ccaactgcac    60
caagagctct ggcacctctt ccccaacagg ccagatgccg ctagagactt cctgttccac   120
gtggagaagc gtaacacccc cgaagggtgc cacgtgctgt tgcagagtgc ccagatgcca   180
gtgagtaccg ctgttgccac tgtcatcaag actaaacaag ttgaattcca actgcaagtg   240
ggcgtccctc tgtatttccg cctcagggcc aaccccatca aaaccatcct ggacaaccag   300
aagcggctgg atagcaaagg taatatcaag agatgccgcg tgcctctgat caaggaggcc   360
gagcagatcg cttggctgca acgcaagctg ggtaacgccg cgagagtgga agatgtgcac   420
ccaatctccg agcgcccgca gtatttctcc ggggagggga agaacggcaa aattcagact   480
gtctgcttcg aggggtgct cactattaac gacgccctg ctctgatcga cctcctgcag   540
cagggcattg ggcccgcgaa gagcatggga tgcggattgt tgagcctggc acccctg      597

<210> SEQ ID NO 9
<211> LENGTH: 29
<212> TYPE: DNA
<213> ORGANISM: Escherichia coli

<400> SEQUENCE: 9
gtagtcccca cgcgtgtggg gatggaccg                                      29

<210> SEQ ID NO 10
<211> LENGTH: 42
<212> TYPE: PRT
<213> ORGANISM: Artificial Sequence
<220> FEATURE:
<223> OTHER INFORMATION: Synthetic Polypeptide

```
<400> SEQUENCE: 10

Lys Leu Ser His Gly Phe Pro Pro Glu Val Glu Glu Gln Asp Asp Gly
1               5                   10                  15

Thr Leu Pro Met Ser Cys Ala Gln Glu Ser Gly Met Asp Arg His Pro
            20                  25                  30

Ala Ala Cys Ala Ser Ala Arg Ile Asn Val
        35                  40

<210> SEQ ID NO 11
<211> LENGTH: 159
<212> TYPE: PRT
<213> ORGANISM: Artificial Sequence
<220> FEATURE:
<223> OTHER INFORMATION: Synthetic Polypeptide

<400> SEQUENCE: 11

Met Ile Ser Leu Ile Ala Ala Leu Ala Val Asp Tyr Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155

<210> SEQ ID NO 12
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 12

Met Ser Leu Ala Leu Ser Leu Thr Ala Asp Gln Met Val Ser Ala Leu
1               5                   10                  15

Leu Asp Ala Glu Pro Pro Ile Leu Tyr Ser Glu Tyr Asp Pro Thr Arg
            20                  25                  30

Pro Phe Ser Glu Ala Ser Met Met Gly Leu Leu Thr Asn Leu Ala Asp
        35                  40                  45

Arg Glu Leu Val His Met Ile Asn Trp Ala Lys Arg Val Pro Gly Phe
    50                  55                  60

Val Asp Leu Ala Leu His Asp Gln Val His Leu Leu Glu Cys Ala Trp
65                  70                  75                  80

Met Glu Ile Leu Met Ile Gly Leu Val Trp Arg Ser Met Glu His Pro
                85                  90                  95
```

```
Gly Lys Leu Leu Phe Ala Pro Asn Leu Leu Asp Arg Asn Gln Gly
            100                 105                 110
Lys Cys Val Glu Gly Gly Val Glu Ile Phe Asp Met Leu Leu Ala Thr
        115                 120                 125
Ser Ser Arg Phe Arg Met Met Asn Leu Gln Gly Glu Glu Phe Val Cys
130                 135                 140
Leu Lys Ser Ile Ile Leu Leu Asn Ser Gly Val Tyr Thr Phe Leu Ser
145                 150                 155                 160
Ser Thr Leu Lys Ser Leu Glu Glu Lys Asp His Ile His Arg Val Leu
                165                 170                 175
Asp Lys Ile Thr Asp Thr Leu Ile His Leu Met Ala Lys Ala Gly Leu
            180                 185                 190
Thr Leu Gln Gln Gln His Gln Arg Leu Ala Gln Leu Leu Leu Ile Leu
        195                 200                 205
Ser His Ile Arg His Met Ser Ser Lys Arg Met Glu His Leu Tyr Ser
    210                 215                 220
Met Lys Cys Lys Asn Val Val Pro Leu Ser Asp Leu Leu Leu Glu Met
225                 230                 235                 240
Leu Asp Ala His Arg Leu
                245

<210> SEQ ID NO 13
<211> LENGTH: 101
<212> TYPE: DNA
<213> ORGANISM: Artificial Sequence
<220> FEATURE:
<223> OTHER INFORMATION: Synthetic Polynucleotide

<400> SEQUENCE: 13
acttccatca tagttatggc catgactact ctagctagca gtgttaaatc attcagctac      60
ctgagagggg cccctataac tctctacggc taacctgaat g                         101

<210> SEQ ID NO 14
<211> LENGTH: 103
<212> TYPE: DNA
<213> ORGANISM: Artificial Sequence
<220> FEATURE:
<223> OTHER INFORMATION: Synthetic Polynucleotide

<400> SEQUENCE: 14
acttccatca tagttatggc catgactact ctagctagca gtgttaaatc attcagctac      60
ctgagagggg cccctataac tctctacggc taacctgaat gga                       103

<210> SEQ ID NO 15
<211> LENGTH: 113
<212> TYPE: DNA
<213> ORGANISM: Artificial Sequence
<220> FEATURE:
<223> OTHER INFORMATION: Synthetic Polynucleotide

<400> SEQUENCE: 15
acttccatca tagttatggc catgactact ctagctagca gtgttaaatc attcagctac      60
ctgagagggg cccctataac tctctacggc taacctgaat ggactacgac ata            113

<210> SEQ ID NO 16
<211> LENGTH: 128
<212> TYPE: DNA
<213> ORGANISM: Artificial Sequence
<220> FEATURE:
<223> OTHER INFORMATION: Synthetic Polynucleotide
```

<400> SEQUENCE: 16
acttccatca tagttatggc catgactact ctagctagca gtgttaaatc attcagctac    60
ctgagagggg cccctataac tctctacggc taacctgaat ggactacgac atagtctagt   120
ccgccaag                                                            128

<210> SEQ ID NO 17
<211> LENGTH: 207
<212> TYPE: PRT
<213> ORGANISM: Artificial Sequence
<220> FEATURE:
<223> OTHER INFORMATION: Synthetic Polypeptide

<400> SEQUENCE: 17

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
        50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 18
<211> LENGTH: 621
<212> TYPE: DNA
<213> ORGANISM: Artificial Sequence
<220> FEATURE:
<223> OTHER INFORMATION: Synthetic Polynucleotide

<400> SEQUENCE: 18
atgtcaagac tcgacaagag caaggtgatt aacagtgcac tggaacttct caatgaagtt    60
gggatcgagg ggctgactac tagaaaactc gcacagaaac tggggggtga gcagcccacc   120
ttgtactggc acgttaaaaa caaaagggcc ctgctggatg ctctggccat cgagatgctg   180
gataggcatc ataccccactt ctgccctctg gaaggagaat cctggcagga tttccttaga   240
aacaacgcca gtcctttcg ctgtgctctt cttagccacc gggatggtgc taaagtccat   300
ctcggcacac gaccaactga gaagcagtac gaaactctcg agaaccagct ggcctttctc   360

```
tgtcaacagg gctttctct tgaaaacgcc ctgtacgcac tgagtgcagt tgggcacttt      420
acactcggat gtgttctgga ggaccaagaa catcaggtgg caaaggaaga gagggagacc      480
cctacgactg actccatgcc ccctctcttg aggcaggcaa tagaattgtt cgaccatcag      540
ggcgcagaac ccgcctttct gtttgggctg gaactgatta tctgcggtct tgagaaacag      600
ctgaagtgcg agtccgggag c                                                621
```

<210> SEQ ID NO 19
<211> LENGTH: 124
<212> TYPE: DNA
<213> ORGANISM: Artificial Sequence
<220> FEATURE:
<223> OTHER INFORMATION: Synthetic Polynucleotide

<400> SEQUENCE: 19

```
atccaggcag agaaaggtcg atacggacgg aatgtggtgg cctggatcaa caacaacaaa      60
atccaggcag agaaaggtcg atacggacgg aatgtggtgg cctggatcaa caacaacaac     120
actg                                                                   124
```

<210> SEQ ID NO 20
<211> LENGTH: 300
<212> TYPE: PRT
<213> ORGANISM: Artificial Sequence
<220> FEATURE:
<223> OTHER INFORMATION: Synthetic Polypeptide

<400> SEQUENCE: 20

```
Met Leu Pro Leu Asp Ser Leu Leu His Leu Thr Ala Pro Ala Pro
1               5                   10                  15

Ala Pro Ala Pro Ala Pro Arg Arg Ser His Gln Thr Pro Thr Pro Pro
            20                  25                  30

His Ser Phe Leu Ser Pro Asp Ala Gln Val Leu Val Leu Ala Ile Ser
        35                  40                  45

Ser His Pro Leu Pro Thr Leu Ala Ala Phe Leu Ala Ser Arg Arg Asp
    50                  55                  60

Glu Leu Leu Arg Ala Asp Ile Thr Ser Leu Leu Lys Ala Leu Glu Leu
65                  70                  75                  80

Ser Gly His Trp Glu Trp Ala Leu Ala Leu Leu Arg Trp Ala Gly Lys
                85                  90                  95

Glu Gly Ala Ala Asp Ala Ser Ala Leu Glu Met Val Val Arg Ala Leu
            100                 105                 110

Gly Arg Glu Gly Gln His Asp Ala Val Cys Ala Leu Leu Asp Glu Thr
        115                 120                 125

Pro Leu Pro Pro Gly Ser Arg Leu Asp Val Arg Ala Tyr Thr Thr Val
    130                 135                 140

Leu His Ala Leu Ser Arg Ala Gly Arg Tyr Glu Arg Ala Leu Glu Leu
145                 150                 155                 160

Phe Ala Glu Leu Arg Arg Gln Gly Val Ala Pro Thr Leu Val Thr Tyr
                165                 170                 175

Asn Val Val Leu Asp Val Tyr Gly Arg Met Gly Arg Ser Trp Pro Arg
            180                 185                 190

Ile Val Ala Leu Leu Asp Glu Met Arg Ala Ala Gly Val Glu Pro Asp
        195                 200                 205

Gly Phe Thr Ala Ser Thr Val Ile Ala Ala Cys Cys Arg Asp Gly Leu
    210                 215                 220
```

Val Asp Glu Ala Val Ala Phe Phe Glu Asp Leu Lys Ala Arg Gly His
225                 230                 235                 240

Ala Pro Cys Val Val Thr Tyr Asn Ala Leu Leu Gln Val Phe Gly Lys
            245                 250                 255

Ala Gly Asn Tyr Thr Glu Ala Leu Arg Val Leu Gly Glu Met Glu Gln
        260                 265                 270

Asn Gly Cys Gln Pro Asp Ala Val Thr Tyr Asn Glu Leu Ala Gly Thr
    275                 280                 285

Tyr Ala Arg Ala Gly Phe Phe Glu Glu Ala Ala Arg
290                 295                 300

<210> SEQ ID NO 21
<211> LENGTH: 2252
<212> TYPE: DNA
<213> ORGANISM: Artificial Sequence
<220> FEATURE:
<223> OTHER INFORMATION: Synthetic Polynucleotide

<400> SEQUENCE: 21

| | | | | | |
|---|---|---|---|---|---|
| atgctcccct | tggacagtct | cctgctgcat | ctcaccgccc | cgcccccgc | cccagcccct | 60 |
| gctccaagaa | ggtctcatca | aacgccgacc | ccccctcaca | gcttcctgtc | ccctgatgct | 120 |
| caggtgttgg | tactcgcaat | cagttctcac | cctctgccta | ccctggctgc | tttcctcgct | 180 |
| agcaggcggg | atgagttgct | gagggccgat | atcacctctc | tccttaaggc | acttgagctg | 240 |
| tctgggcact | gggaatgggc | attggccctg | ctgcgatggg | caggtaagga | gggagctgcc | 300 |
| gatgctagcg | ctttggagat | ggtcgtaaga | gcactcggta | gagaaggcca | gcatgacgca | 360 |
| gtctgtgctc | tgctggacga | aactccattg | cctccaggca | gcagactgga | cgtacgggcc | 420 |
| tacaccaccg | tgcttcacgc | cctctcaaga | gccggtaggt | acgagagagc | tctcgagctg | 480 |
| ttcgctgaac | tcagaagaca | gggcgtggcc | ccaaccttgg | taacttataa | cgtggtactg | 540 |
| gacgtctacg | gccgaatggg | gagaagttgg | ccgcgcatcg | tcgcattgct | cgacgaaatg | 600 |
| cgggccgcag | gcgtcgagcc | agatgggttt | accgcaagca | cggtgatcgc | tgcttgctgc | 660 |
| cgggatggtt | tggtgatga | gccgtggcc | ttctttgagg | acttgaaggc | caggggtcac | 720 |
| gcaccttgtg | tcgtaaccta | taacgcactg | ttgcaggtgt | tcggcaaggc | tgggaattat | 780 |
| actgaggccc | tgagagttct | tggcgaaatg | gagcagaacg | ggtgccagcc | agatgctgtg | 840 |
| acatataatg | agctggccgg | aacctacgca | cgcgccggct | tctttgagga | ggccgcccgg | 900 |
| tgtctggaca | cgatggccag | taagggcctg | cttcctaacg | cattcacata | caataccgtg | 960 |
| atgacagcat | atgaaatgt | ggggaaggtc | gacgaagctc | tcgcccttt | cgatcagatg | 1020 |
| aaaaagactg | gcttcgttcc | caacgtgaac | acgtacaacc | tggtcctggg | gatgctggga | 1080 |
| aagaaatcaa | gattcacggt | aatgttgaa | atgttgggcg | aaatgagcag | gtcaggatgt | 1140 |
| acccctaaca | gggttacttg | gaatactatg | ctcgctgtgt | gtggaaagcg | agggatggaa | 1200 |
| gattacgtga | cacgggttct | ggagggcatg | cggagttgcg | gtgtcgagct | gtcccgagac | 1260 |
| acatacaaca | ccctcatcgc | tgcttatggg | aggtgcggta | gccggacaaa | tgcttttaag | 1320 |
| atgtataacg | aaatgacgtc | cgcagggttc | actccctgca | tcactacata | taacgctctg | 1380 |
| ctgaatgtgc | tctctcggca | aggagactgg | tccactgctc | agtcaatcgt | ttcaaagatg | 1440 |
| cggactaagg | gctttaagcc | caacgagcaa | tcttactcac | tcctcctgca | gtgttacgca | 1500 |
| aaggggggca | atgtggcagg | aattgcagcc | atcgaaaacg | aagtttacgg | gtccggcgct | 1560 |
| gttttcccat | cttgggtgat | cctgaggact | cttgtaatcg | ctaatttcaa | atgtcgccgc | 1620 |

```
ttggacggca tggaaactgc tttccaggag gtaaaggcca gggggtataa tcctgatttg    1680
gtgatattca actcaatgct ttccatctac gctaagaatg gtatgtatag caaagcaact    1740
gaggtcttcg actcaattaa gaggtcaggt ctgtccccag accttataac ttacaattcc    1800
ttgatggata tgtatgccaa gtgtagcgag tcctgggaag ctgaaaagat tcttaatcag    1860
ctgaaatgtt cccagactat gaagcccgat gttgttagct ataatacagt tatcaacgga    1920
ttctgcaaac agggccttgt gaagaagcc  cagagagtgc tgtccgaaat ggtcgccgac    1980
ggcatggctc cttgcgctgt gacctaccat acattggtcg gcggctattc ctctctcgag    2040
atgttctccg aggccaggga ggtcatcggc tacatggtgc aacatggact gaaacctatg    2100
gaactgacct ataggagggt ggtggaatca tactgcagag ccaagcgatt cgaggaagct    2160
cggggtttcc tgtccgaagt gtctgagact gatctggact tcgacaaaaa agctttggaa    2220
gcatacatcg aggacgctca atttgggcgc ta                                  2252
```

<210> SEQ ID NO 22
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 22

```
attgtatcct taaccatttc ttttattgta tccttaacca tttctttt                 47
```

<210> SEQ ID NO 23
<211> LENGTH: 130
<212> TYPE: PRT
<213> ORGANISM: Artificial Sequence
<220> FEATURE:
<223> OTHER INFORMATION: Synthetic Polypeptide

<400> SEQUENCE: 23

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
    50                  55                  60

Val Pro Lys Val Ala Thr Gln Thr Val Gly Gly Glu Glu Leu Pro Val
65                  70                  75                  80

Ala Gly Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
130
```

<210> SEQ ID NO 24
<211> LENGTH: 390
<212> TYPE: DNA
<213> ORGANISM: Artificial Sequence
<220> FEATURE:
<223> OTHER INFORMATION: Synthetic Polynucleotide

<400> SEQUENCE: 24

```
atggcttcta actttactca gttcgttctc gtcgacaatg gcggaactgg cgacgtgact    60
gtcgccccaa gcaacttcgc taacggggtc gctgaatgga tcagctctaa ctcgcgttca   120
caggcttaca agtaacctg tagcgttcgt cagagctctg cgcagaagcg caaatacacc    180
atcaaagtcg aggtgcctaa agtggcaacc cagactgttg gtggtgagga gcttcctgta   240
gccggttggc gttcgtactt aaatatggaa ctaaccattc caattttcgc cacgaattcc   300
gactgcgagc ttattgttaa ggcaatgcaa ggcctcctaa aagatggaaa cccgattccc   360
tcggccatcg cagcaaactc cggcatctac                                    390
```

<210> SEQ ID NO 25
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 25

```
acatgaggat cacccatgtc tgcaggtcga ctctagaaaa catgaggatc acccatgtcc    60
tgcaggtcga ctctagaaa                                                79
```

<210> SEQ ID NO 26
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 26

Met Tyr Val Arg Phe Glu Val Pro Glu Asp Met Gln Asn Glu Ala Leu
1               5                   10                  15

Ser Leu Leu Glu Lys Val Arg Glu Ser Gly Lys Val Lys Lys Gly Thr
            20                  25                  30

Asn Glu Thr Thr Lys Ala Val Glu Arg Gly Leu Ala Lys Leu Val Tyr
        35                  40                  45

Ile Ala Glu Asp Val Asp Pro Pro Glu Ile Val Ala His Leu Pro Leu
    50                  55                  60

Leu Cys Glu Glu Lys Asn Val Pro Tyr Ile Tyr Val Lys Ser Lys Asn
65                  70                  75                  80

Asp Leu Gly Arg Ala Val Gly Ile Glu Val Pro Cys Ala Ser Ala Ala
                85                  90                  95

Ile Ile Asn Glu Gly Glu Leu Arg Lys Glu Leu Gly Ser Leu Val Glu
            100                 105                 110

Lys Ile Lys Gly Leu Gln Lys
        115

<210> SEQ ID NO 27
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 27

```
atgtacgtga gatttgaggt tcctgaggac atgcagaacg aagctctgag tctgctggag    60
aaggttaggg agagcggtaa ggtaaagaaa ggtaccaacg agacgacaaa ggctgtggag   120
aggggactgg caaagctcgt ttacatcgca gaggatgttg acccgcctga gatcgttgct   180
```

```
catctgcccc tcctctgcga ggagaagaat gtgccgtaca tttacgttaa aagcaagaac    240
gaccttggaa gggctgtggg cattgaggtg ccatgcgctt cggcagcgat aatcaacag    300 ggagagctga gaaggagct tggaagcctt gtggagaaga ttaaaggcct tcagaag       357
```

<210> SEQ ID NO 28
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 28

```
gggcgtgatc cgaaaggtga cccggatctg gggcgtgatc cgaaaggtga cccggatcca    60
ccggtc                                                               66
```

<210> SEQ ID NO 29
<211> LENGTH: 286
<212> TYPE: PRT
<213> ORGANISM: Artificial Sequence
<220> FEATURE:
<223> OTHER INFORMATION: Synthetic Polypeptide

<400> SEQUENCE: 29

```
Met Pro Ala Ala Thr Val Asp His Ser Gln Arg Ile Cys Glu Val Trp
1               5                  10                  15

Ala Cys Asn Leu Asp Glu Glu Met Lys Lys Ile Arg Gln Val Ile Arg
            20                  25                  30

Lys Tyr Asn Tyr Val Ala Met Asp Thr Glu Phe Pro Gly Val Val Ala
        35                  40                  45

Arg Pro Ile Gly Glu Phe Arg Ser Asn Ala Asp Tyr Gln Tyr Gln Leu
    50                  55                  60

Leu Arg Cys Asn Val Asp Leu Leu Lys Ile Ile Gln Leu Gly Leu Thr
65                  70                  75                  80

Phe Met Asn Glu Gln Gly Glu Tyr Pro Pro Gly Thr Ser Thr Trp Gln
                85                  90                  95

Phe Asn Phe Lys Phe Asn Leu Thr Glu Asp Met Tyr Ala Gln Asp Ser
            100                 105                 110

Ile Glu Leu Leu Thr Thr Ser Gly Ile Gln Phe Lys Lys His Glu Glu
        115                 120                 125

Glu Gly Ile Glu Thr Gln Tyr Phe Ala Glu Leu Leu Met Thr Ser Gly
    130                 135                 140

Val Val Leu Cys Glu Gly Val Lys Trp Leu Ser Phe His Ser Gly Tyr
145                 150                 155                 160

Asp Phe Gly Tyr Leu Ile Lys Ile Leu Thr Asn Ser Asn Leu Pro Glu
                165                 170                 175

Glu Glu Leu Asp Phe Phe Glu Ile Leu Arg Leu Phe Phe Pro Val Ile
            180                 185                 190

Tyr Asp Val Lys Tyr Leu Met Lys Ser Cys Lys Asn Leu Lys Gly Gly
        195                 200                 205

Leu Gln Glu Val Ala Glu Gln Leu Glu Leu Glu Arg Ile Gly Pro Gln
    210                 215                 220

His Gln Ala Gly Ser Asp Ser Leu Leu Thr Gly Met Ala Phe Phe Lys
225                 230                 235                 240

Met Arg Glu Met Phe Phe Glu Asp His Ile Asp Asp Ala Lys Tyr Cys
                245                 250                 255
```

Gly His Leu Tyr Gly Leu Gly Ser Gly Ser Ser Tyr Val Gln Asn Gly
            260                 265                 270

Thr Gly Asn Ala Tyr Glu Glu Ala Asn Lys Gln Ser Val
        275                 280                 285

<210> SEQ ID NO 30
<211> LENGTH: 858
<212> TYPE: DNA
<213> ORGANISM: Artificial Sequence
<220> FEATURE:
<223> OTHER INFORMATION: Synthetic Polynucleotide

<400> SEQUENCE: 30
atgccagcgg caactgtaga tcatagccaa agaatttgtg aagtttgggc ttgcaacttg     60
gatgaagaga tgaagaaaat tcgtcaagtt atccgaaaat ataattacgt tgctatggac    120
accgagtttc aggtgtggt tgcaagaccc attggagaat tcaggagcaa tgctgactat    180
caataccaac tattgcggtg taatgtagac ttgttaaaga taattcagct aggactgaca    240
tttatgaatg agcaaggaga ataccctcca ggaacttcaa cttggcagtt taattttaaa    300
tttaatttga cggaggacat gtatgcccag gactctatag agctactaac aacatctggt    360
atccagttta aaaacatga ggaggaagga attgaaaccc agtactttgc agaacttctt    420
atgacttctg gagtggtcct ctgtgaaggg gtcaaatggt tgtcatttca gcggttac     480 gactttggct acttaatcaa atcctaacc aactctaact tgcctgaaga gaacttgac    540 ttctttgaga tccttcgatt gttttttcct gtcatttatg atgtgaagta cctcatgaag    600
agctgcaaaa atctcaaagg tggattacag gaggtggcag aacagttaga gctggaacgg    660
ataggaccac aacatcaggc aggatctgat tcattgctca caggaatggc ctttttcaaa    720
atgagagaaa tgttctttga agatcatatt gatgatgcca aatattgtgg tcatttgtat    780
ggccttggtt ctggttcatc ctatgtacag aatggcacag gaatgcata tgaagaggaa    840 gccaacaagc agtcagtt                                                  858

<210> SEQ ID NO 31
<211> LENGTH: 483
<212> TYPE: PRT
<213> ORGANISM: Artificial Sequence
<220> FEATURE:
<223> OTHER INFORMATION: Synthetic Polypeptide

<400> SEQUENCE: 31

Met Ser Thr Ala Arg Thr Glu Asn Pro Val Ile Met Gly Leu Ser Ser
1               5                   10                  15

Gln Asn Gly Gln Leu Arg Gly Pro Val Lys Ala Ser Ala Gly Pro Gly
            20                  25                  30

Gly Gly Gly Thr Gln Pro Gln Pro Gln Leu Asn Gln Leu Lys Asn Thr
        35                  40                  45

Ser Thr Ile Asn Asn Gly Thr Pro Gln Gln Ala Gln Ser Met Ala Ala
    50                  55                  60

Thr Ile Lys Pro Gly Asp Asp Trp Lys Lys Thr Leu Lys Leu Pro Pro
65                  70                  75                  80

Lys Asp Leu Arg Ile Lys Thr Ser Asp Val Thr Ser Thr Lys Gly Asn
                85                  90                  95

Glu Phe Glu Asp Tyr Cys Leu Lys Arg Glu Leu Leu Met Gly Ile Phe
            100                 105                 110

Glu Met Gly Trp Glu Lys Pro Ser Pro Ile Gln Glu Glu Ser Ile Pro
        115                 120                 125

Ile Ala Leu Ser Gly Arg Asp Ile Leu Ala Arg Ala Lys Asn Gly Thr
130                 135                 140

Gly Lys Ser Gly Ala Tyr Leu Ile Pro Leu Leu Glu Arg Leu Asp Leu
145                 150                 155                 160

Lys Lys Asp Asn Ile Gln Ala Met Val Ile Val Pro Thr Arg Glu Leu
                165                 170                 175

Ala Leu Gln Val Ser Gln Ile Cys Ile Gln Val Ser Lys His Met Gly
                180                 185                 190

Gly Ala Lys Val Met Ala Thr Thr Gly Gly Thr Asn Leu Arg Asp Asp
            195                 200                 205

Ile Met Arg Leu Asp Asp Thr Val His Val Val Ile Ala Thr Pro Gly
210                 215                 220

Arg Ile Leu Asp Leu Ile Lys Lys Gly Val Ala Lys Val Asp His Val
225                 230                 235                 240

Gln Met Ile Val Leu Asp Glu Ala Asp Lys Leu Leu Ser Gln Asp Phe
                245                 250                 255

Val Gln Ile Met Glu Asp Ile Ile Leu Thr Leu Pro Lys Asn Arg Gln
                260                 265                 270

Ile Leu Leu Tyr Ser Ala Thr Phe Pro Leu Ser Val Gln Lys Phe Met
            275                 280                 285

Asn Ser His Leu Gln Lys Pro Tyr Glu Ile Asn Leu Met Glu Glu Leu
290                 295                 300

Thr Leu Lys Gly Val Thr Gln Tyr Tyr Ala Tyr Val Thr Glu Arg Gln
305                 310                 315                 320

Lys Val His Cys Leu Asn Thr Leu Phe Ser Arg Leu Gln Ile Asn Gln
                325                 330                 335

Ser Ile Ile Phe Cys Asn Ser Ser Gln Arg Val Glu Leu Leu Ala Lys
            340                 345                 350

Lys Ile Ser Gln Leu Gly Tyr Ser Cys Phe Tyr Ile His Ala Lys Met
            355                 360                 365

Arg Gln Glu His Arg Asn Arg Val Phe His Asp Phe Arg Asn Gly Leu
370                 375                 380

Cys Arg Asn Leu Val Cys Thr Asp Leu Phe Thr Arg Gly Ile Asp Ile
385                 390                 395                 400

Gln Ala Val Asn Val Val Ile Asn Phe Asp Phe Pro Lys Leu Ala Glu
                405                 410                 415

Thr Tyr Leu His Arg Ile Gly Arg Ser Gly Arg Phe Gly His Leu Gly
            420                 425                 430

Leu Ala Ile Asn Leu Ile Thr Tyr Asp Asp Arg Phe Asn Leu Lys Ser
            435                 440                 445

Ile Glu Glu Gln Leu Gly Thr Glu Ile Lys Pro Ile Pro Ser Asn Ile
450                 455                 460

Asp Lys Ser Leu Tyr Val Ala Glu Tyr His Ser Glu Pro Ala Glu Asp
465                 470                 475                 480

Glu Lys Pro

<210> SEQ ID NO 32
<211> LENGTH: 1449
<212> TYPE: DNA
<213> ORGANISM: Artificial Sequence
<220> FEATURE:
<223> OTHER INFORMATION: Synthetic Polynucleotide

<400> SEQUENCE: 32

```
atgagcacag ctcgcaccga gaacccggtg attatgggcc tgtccagcca gaacggacag    60
ctcagagggc ctgtaaaggc ttcagcaggc cccggcggag gcggcacaca accacaacca   120
cagcttaatc agcttaagaa tactagcact attaataacg gaacaccgca gcaggcccaa   180
agcatggctg ccacaattaa acccggagat gactggaaga agaccctgaa gctccctcca   240
aaagatctca ggattaaaac tagcgatgtt acttcaacaa agggaaatga gttcgaagac   300
tactgtctga agcgagagtt gctgatgggg atttcgaaa tgggctggga agcccctct    360 cctattcaag aagagagcat ccccatcgct ctgtccggga gggacatcct tgccagggct   420
aaaaatggga ccgaaaaatc aggagcttac ttgatcccac tccttgaaag gcttgatctc   480
aagaaggaca acatccaagc tatggttatc gtgccaacta gagaactcgc cctccaggtc   540
agccagattt gcatccaggt gagtaagcac atgggcggag ctaaggtgat ggctacaact   600
ggagggacta acctgcgaga cgacataatg agacttgatg acacagtcca tgtggtcatc   660
gctacacctg ggaggattct ggatctgatc aaaaaaggag tggcaaaggt ggatcatgtg   720
cagatgatag tcttggacga ggccgacaaa ctgctgagcc aagactttgt gcagatcatg   780
gaggatatca tcttgacact ccccaagaac cgacagattc tgctgtactc cgcaacattt   840 cctcttttccg ttcagaaatt catgaactca catctccaga aaccttatga gatcaatttg   900
atggaagaac tgacactgaa gggcgtgacc cagtattatg cctacgttac tgagaggcaa   960
aaggtccact gcctgaatac tctcttctcc aggctccaga tcaaccagtc tatcatcttt  1020
tgcaatagct cccagcgagt cgagctgctg gctaagaaga tctcacagct tggatattcc  1080
tgtttctaca tccatgctaa gatgagacaa gagcacagaa accgcgtctt tcatgatttc  1140
cggaacggac tctgtcgcaa cctggtttgc acagatcttt ttactagagg catcgatatc  1200
caagcagtga acgtggttat caacttcgac tttcccaaac tcgccgagac ttatcttcat  1260
agaattggcc gatccggtag gtttgggcac ctggggctcg ccatcaatct cattacgtat  1320
gatgataggt tcaacctcaa gtcaatagaa gagcagttgg ggaccgagat caaaccaatc  1380
ccgagcaata ttgacaaatc actctatgtg gccgaatacc attcagagcc tgccgaggat  1440
gagaagcct                                                         1449
```

<210> SEQ ID NO 33
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 33

```
caccacgaac ctgatgagtc cgtgaggacg aaacgagcta gctcgtcgtt cgtgctg       57
```

<210> SEQ ID NO 34
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 34

```
ggcgtcggag tatccaatca gtggatgtac tactccctga tgagtcccaa ataggacgaa    60
acgcc                                                                65
```

<210> SEQ ID NO 35
<211> LENGTH: 64

<212> TYPE: DNA
<213> ORGANISM: Artificial Sequence
<220> FEATURE:
<223> OTHER INFORMATION: Synthetic Polynucleotide

<400> SEQUENCE: 35
gggtgccctg tcggaggatg tgctttcctc cctgatgagt ccgtgaggac gaaacagggc    60
accc    64

<210> SEQ ID NO 36
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 36
ggccggcatg gtcccagcct cctcgctggc gccggctggg caacatgctt cggcatggcg    60
aatgggac    68

<210> SEQ ID NO 37
<211> LENGTH: 341
<212> TYPE: DNA
<213> ORGANISM: Artificial Sequence
<220> FEATURE:
<223> OTHER INFORMATION: Synthetic Polynucleotide

<400> SEQUENCE: 37
atagggcgga gggaagctca tcagtggggc cacgagctga gtgcgtcctg tcactccact    60
cccatgtccc ttgggaaggt ctgagactag ggccagaggc ggccctaaca gggctctccc   120
tgagcttcgg ggaggtgagt tcccagagaa cggggctccg cgcgaggtca gactgggcag   180
gagatgccgt ggaccccgcc cttcggggag gggcccggcg gatgcctcct ttgccggagc   240
ttggaacaga ctcacggcca gcgaagtgag ttcaatggct gaggtgaggt accccgcagg   300
ggacctcata acccaattca gactactctc ctccgcccat t   341

<210> SEQ ID NO 38
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 38
gacgctggtg gctggcactc ctggtttcca ggacggggtt caagtccctg cggtgtct    58

<210> SEQ ID NO 39
<211> LENGTH: 110
<212> TYPE: RNA
<213> ORGANISM: Artificial Sequence
<220> FEATURE:
<223> OTHER INFORMATION: Synthetic Polypeptide

<400> SEQUENCE: 39
gauucgucag uaggguugua aagguuuuuc uuuuccugag aaaacaaccu uuuguuuucu    60 caggguuuugc uuuuuggccu uucccuagcu uuaaaaaaaa aaaagcaaaa   110

<210> SEQ ID NO 40
<211> LENGTH: 74
<212> TYPE: RNA
<213> ORGANISM: Artificial Sequence
<220> FEATURE:

```
<223> OTHER INFORMATION: Synthetic Polypeptide

<400> SEQUENCE: 40
gccgccgcag guguuucuuu uacugagugc agcccauggc cgcacucagg uuuugcuuuu    60
caccuuccca ucug                                                      74

<210> SEQ ID NO 41
<211> LENGTH: 64
<212> TYPE: RNA
<213> ORGANISM: Artificial Sequence
<220> FEATURE:
<223> OTHER INFORMATION: Synthetic Polypeptide

<400> SEQUENCE: 41
gcuggguuuu uccuuguucg caccggacac cuccagugac cagacggcaa gguuuuaucc    60
cagu                                                                  64

<210> SEQ ID NO 42
<211> LENGTH: 25
<212> TYPE: RNA
<213> ORGANISM: Artificial Sequence
<220> FEATURE:
<223> OTHER INFORMATION: Synthetic Polypeptide

<400> SEQUENCE: 42
aaaaaggcuc uuuucagagc accca                                          25

<210> SEQ ID NO 43
<211> LENGTH: 118
<212> TYPE: RNA
<213> ORGANISM: Artificial Sequence
<220> FEATURE:
<223> OTHER INFORMATION: Synthetic Polypeptide

<400> SEQUENCE: 43
uuaaaacagc ucugggguug uacccacccc agaggcccac guggcggcua guacuccggu    60
auugcgguac ccuuguacgc cuguuuauua ucccuuccc guaacuuaga cgcacaaa     118

<210> SEQ ID NO 44
<211> LENGTH: 573
<212> TYPE: DNA
<213> ORGANISM: Unknown
<220> FEATURE:
<223> OTHER INFORMATION: Encephalomyocarditis virus

<400> SEQUENCE: 44
cccctctccc tccccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctaggggt ctttcccctc tcgccaaagg   180
aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa agccacgtg tataagatac acctgcaaag gcggcacaac cccagtgcca   360
cgttgtgagt tggatagttg tggaaagagt caaatggctc acctcaagcg tattcaacaa   420
ggggctgaag gatgcccaga aggtacccca ttgtatggga tctgatctgg ggcctcggtg   480
cacatgcttt acatgtgttt agtcgaggtt aaaaaacgtc taggccccccc gaaccacggg   540 gacgtggttt tccttttgaaa aacacgatga taa                               573
```

```
<210> SEQ ID NO 45
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 45
tttgtattca gcccatatcg                                              20

<210> SEQ ID NO 46
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 46
aacgatatgg gctgaataca aa                                           22

<210> SEQ ID NO 47
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 47
tttaattaaa gacttcaagc g                                            21

<210> SEQ ID NO 48
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 48
ccgcttgaag tctttaatta aa                                           22

<210> SEQ ID NO 49
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 49
taattgtcaa atcagagtgc                                              20

<210> SEQ ID NO 50
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 50
aagcactctg atttgacaat ta                                           22

<210> SEQ ID NO 51
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 51
tttatgagga atctctttgg                                                    20

<210> SEQ ID NO 52
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 52
aaccaaagag attcctcata aa                                                 22

<210> SEQ ID NO 53
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 53
ttcgaagtat tccgcgtacg                                                    20

<210> SEQ ID NO 54
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 54
cacgtacgcg gaatacttcg aa                                                 22
```

RNA-BASED REGULATORY TECHNOLOGIES FOR MIRNA SENSORS

RELATED APPLICATION

This application claims the benefit of the filing date under 35 U.S.C. § 119 of U.S. Provisional Application Ser. No. 62/713,186, filed Aug. 1, 2018, the entire contents of which are incorporated by reference herein.

GOVERNMENT SUPPORT

This invention was made with Government support under Grant Nos. R01 CA173712 and P50 GM098792 awarded by the National Institutes of Health. The Government has certain rights in the invention.

BACKGROUND

The ability to classify individual cell types in complex biological samples (e.g., in a tissue or during cellular differentiation) can be achieved using the unique expression patterns of microRNAs in specific cell types or in individual cells. Such cell state classifiers allowing gene circuits to respond to miRNAs with "low" and "high" activity in the cell have been developed. Such cell state classifiers can be used to activate therapeutic genes in specific cells, identify or eliminate cells in a diseased state, or monitor differentiation in a tissue.

SUMMARY

Provided herein are cell state classifiers designed to launch a self-amplifying RNA (e.g., a self-amplifying replicon derived from a virus) that expresses an output molecule (e.g., a detectable molecule or a therapeutic molecule) at very high levels. Further provided herein are cell state classifiers that are encoded in one single initial RNA transcript. In such cell state classifiers, the expression of the output molecule is regulated translationally. The cell state classifiers provided herein either produce more robust output signals, or are easier to implement in various applications.

Accordingly, some aspects of the present disclosure provide cell state classifiers, comprising: (i) a first sensor circuit comprising a promoter operably linked to a nucleotide sequence encoding a first activator and one or more target sites for a first microRNA; (ii) a second sensor circuit comprising: (a) a first part comprising a promoter operably linked to a nucleotide sequence encoding a second activator, and one or more target sites for a second microRNA; and (b) a second part comprising a promoter that is activated by the second activator, operably linked to a nucleotide sequence encoding an endoribonuclease, and one or more target sites for a second microRNA; and (iii) a signal circuit comprising an activatable promoter that is activated by the first activator, operably linked to a nucleotide encoding a self-amplifying RNA comprising a subgenomic promoter operably linked to a nucleotide sequence encoding an output molecule, one or more target sites for the first microRNA, and a recognition site for the endoribonuclease of (ii)(b).

In some embodiments, the endoribonuclease belongs to the CRISPR-associated endoribonuclease 6 (Cas6) family. In some embodiments, the endoribonuclease comprises Csy4, Cse3, Cas6, or a variant thereof. In some embodiments, the endoribonuclease comprises Csy4 fused to a degradation domain. In some embodiments, the degradation domain is selected from the group consisting of: PEST, DDd, and DDe.

In some embodiments, the self-amplifying RNA is derived from a virus. In some embodiments, the virus is an alphavirus. In some embodiments, the subgenomic promoter is SGP30.

In some embodiments, the one or more target sites for the first microRNA is located upstream and/or downstream of the nucleotide sequence encoding the first activator in the first sensor circuit. In some embodiments, the one or more target sites for the first microRNA is located upstream and/or downstream of the nucleotide sequence encoding the output molecule in the signal circuit. In some embodiments, the one or more target sites for the second microRNA is located upstream and/or downstream of the nucleotide sequence encoding the second activator in (ii)(a) of the second sensor circuit. In some embodiments, the one or more target sites for the second microRNA is located upstream and/or downstream of the nucleotide sequence encoding the endoribonuclease in (ii)(b) of the second sensor circuit.

In some embodiments, the output molecule is a detectable molecule. In some embodiments, the output molecule is a therapeutic molecule.

Other aspects of the present disclosure provide cell state classifiers, comprising a promoter operably linked to a nucleic acid molecule comprising: (i) a first sensor circuit comprising one or more recognition sites for a RNA repressor, operably linked to a nucleotide sequence encoding an output molecule, and one or more target sites for a first microRNA; and (ii) a second sensor circuit that is downstream of the first sensor circuit, comprising a nucleotide sequence encoding the RNA repressor and one or more target sites for a second microRNA, wherein the first sensor circuit and the second sensor circuit are separated by a splitter comprising, from 5' to 3', a first RNA stabilizer, a cleavage site, a second RNA stabilizer, and an internal ribosome entry site.

In some embodiments, the RNA repressor comprises a RNA binding protein. In some embodiments, the RNA binding protein is selected from the group consisting of: TetR, MS2CP, PPR10, and L7Ae. In some embodiments, the RNA binding protein is fused to a modifying domain. In some embodiments, the modifying domain is CNOT7 or DDX6. In some embodiments, the RNA repressor is an endoribonuclease. In some embodiments, the endoribonuclease is Cas6, Cse3 or Csy4.

In some embodiments, the first RNA stabilizer is a synthetic poly-adenylated tail or a RNA triple helix structure. In some embodiments, the first RNA stabilizer is a MALAT1 triplex. In some embodiments, the second RNA stabilizer comprises a 5' RNA cloverleaf element. In some embodiments, the 5' RNA cloverleaf element is derived from poliovirus.

In some embodiments, the cleavage site in the splitter comprises a recognition site for an endoribonuclease. In some embodiments, the endoribonuclease is Cas6, Cse3 or Csy4. In some embodiments, the endoribonuclease is Csy4. In some embodiments, the cleavage site comprises a cis-acting ribozyme. In some embodiments, the cis-acting ribozyme is selected from the group consisting of: hammerhead ribozymes and hepatitis delta virus ribozymes.

In some embodiments, the cell state classifier contains a plurality of the second sensor circuit, each comprising one or more microRNA binding sites for a second microRNA. In some embodiments, each of the plurality of the second sensor circuit comprises a nucleotide sequence encoding a same RNA repressor. In some embodiments, each of the plurality of the second sensor circuit comprises a nucleotide sequence encoding a different RNA repressor. In some embodiments, each second circuit is separated by the splitter.

In some embodiments, the output molecule is a detectable molecule. In some embodiments, the output molecule is a therapeutic molecule.

RNA molecules encoded by the cell state classifiers described are provided. Such RNA molecule contains: (i) a first sensor circuit comprising one or more recognition sites for a RNA repressor, operably linked to a nucleotide sequence encoding an output molecule, and one or more target sites for a first microRNA; and (ii) a second sensor circuit that is downstream of the first sensor circuit, comprising a subgenomic promoter operably linked to a nucleotide sequence encoding the RNA repressor and one or more target sites for a second microRNA, wherein the first sensor circuit and the second sensor circuit are separated by a splitter comprising, from 5' to 3', a first RNA stabilizer, a cleavage site, a second RNA stabilizer, and an internal ribosome entry site.

Cells containing the cell state classifiers described herein are provided. In some embodiments, the cell is a prokaryotic cell. In some embodiments, the prokaryotic cell is a bacterial cell. In some embodiments, the cell is a eukaryotic cell. In some embodiments, the eukaryotic cell is a plant cell, an insect cell, or a mammalian cell. In some embodiments, the mammalian cell is a human cell. In some embodiments, the cell is a diseased cell. In some embodiments, the cell is a cancer cell. In some embodiments, the cell does not express the first microRNA. In some embodiments, the cell expresses the second microRNA. In some embodiments, the cell expresses the first microRNA and does not express the second microRNA. In some embodiments, the cell expresses the first microRNA and expresses the second microRNA. In some embodiments, the cell does not the first microRNA and does not express the second microRNA.

Other aspects of the present disclosure provide methods containing maintaining the cells described herein. In some embodiments, the method further comprises detecting the output molecule. In some embodiments, the method further comprises comprising classifying the cell.

Other aspects of the present disclosure provide methods containing delivering the cell state classifier described herein to a cell and detecting an output molecule.

Methods of treating a disease or disorder are provided. The method contains delivering the cell state classifier described herein to a cell, wherein the output molecule is a therapeutic molecule that is effective for treating the disease or disorder. In some embodiments, the method contains administering an effective amount of a composition comprising the cell state classifier described herein to a subject in need thereof, wherein the output molecule is a therapeutic molecule that is effective for treating the disease or disorder. In some embodiments, the composition further comprises a pharmaceutically acceptable carrier. In some embodiments, the cell is a diseased cell. In some embodiments, the cell is a cancer cell.

Methods of diagnosing a disease or disorder are provided. The method contains delivering the cell state classifier described herein to a cell. In some embodiments, the method contains administering an effective amount of a composition comprising the cell state classifier described herein to a subject in need thereof. In some embodiments, the composition further comprises a pharmaceutically acceptable carrier. In some embodiments, the cell is a diseased cell. In some embodiments, the cell is a cancer cell. In some embodiments, the method further comprises detecting the output molecule. In some embodiments, the lack of expression of the output molecule indicates the disease or disorder. In some embodiments, the expression of the output molecule indicates the disease or disorder.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

The accompanying drawings are not intended to be drawn to scale. For purposes of clarity, not every component may be labeled in every drawing.

(FIG. 1A) Expression of mKate from a standard constitutive promoter (top) vs. DREP (bottom). Standard promoters express more mKate as transfection efficiency rises, while DREP expresses the maximum amount of mKate regardless of transfection efficiency. This is due to the self-amplification of the replicon RNA. (FIG. 1B) DREP regulation by rtTA and Dox. DREP was placed under control of a TRE-tight promoter, and rtTA was added. Without Dox, few cells express DREP (top). Addition of Dox results in high DREP expression (bottom). (FIG. 1C) Regulation of DREP by Csy4. A Csy4 recognition site was placed in the 3' UTR of the DREP payload. Without Csy4 protein, DREP expresses (top). Addition of Csy4 nearly completely represses DREP (bottom).

(FIG. 3A) The RNA-regulation-based miRNA classifier can be encoded on a single transcript, using a splitter (right) consisting of a MALAT1 triplex, a ribozyme Csy4 recognition site, a poliovirus cloverleaf, and an IRES. (FIG. 3B) Additional high sensors can be incorporated by adding more splitters, and encoding the same repressor under control of different miRNAs. (FIG. 3C) Additional high sensors can also use different mRNA repressors, including: nucleases such as Cse3, Cas6, Csy4; RNA binding proteins such as TetR, PPR10, and MS2CP; and RBP-bound functional domains, such as CNOT7 or DDX6.

DETAILED DESCRIPTION OF CERTAIN EMBODIMENTS

Figure 1A:
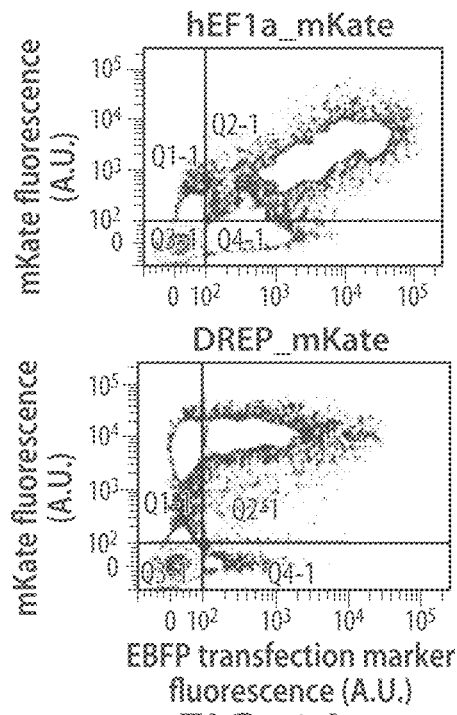
FIGS. 1A-1C: DREP regulation.

Described herein are cell state classifiers that can detect the microRNA profile of a cell and classify the cell accordingly. In some embodiments, the cell state classifiers of the present disclosure are designed to express an output molecule at a very high level, when a matching microRNA profile is detected. In some embodiments, the cell state classifiers of the present disclosure are encoded on a single RNA transcript, making it easier to use in various applications.

A "cell state classifier," as used herein, refers to a system with multiple genetic circuits integrated together by transcriptional or translational control, which is able to sense a microRNA profile (e.g., one or more microRNAs) in a cell and produce an output molecule (e.g., a detectable molecule or a therapeutic molecule) accordingly. A "microRNA profile," as used herein, refers to the expression levels of one or more microRNAs in a cell or a cell type. The microRNA profile may contain expression levels of microRNAs that have no expression or lower expression (e.g., at least 30% lower), and/or expression levels of microRNAs that express or have higher expression (e.g., at least 30% higher) in a cell or a cell type, compared to another cell or a different cell type, respectively. MicroRNAs that have no expression or lower expression is referred to herein as "microRNA-low" or "miR-low," while microRNAs that express or have high expression is referred to herein as "microRNA-high" or "miR-high."

In part, the cell state classifier of the present disclosure is designed to detect miRNA by incorporating target sites of the miRNA to be detected into different genetic circuits (e.g., sensor circuit and/or signal circuit). Expression of the microRNA leads to the degradation of mRNAs encoding the molecules that are produced by these circuits (e.g., activators, repressors, or output molecules), thus leading to different signal output by the cell state classifier, which may be detected and used for classifying the cell.

Multiple inputs (e.g., microRNAs) can be sensed simultaneously by coupling their detection to different portions of the genetic circuit such that the output molecule is produced only when the correct input profile of miRNAs is detected. The cell state classifier may be used in various applications. In some embodiments, the genetic circuits described herein may be used for the detection of a diseased cell (e.g., a cancer cell). In some embodiments, detection of the diseased cell (e.g., the cancer cell) may be achieved via the expression of a detectable output molecule (e.g., a fluorescent protein) upon detection of a matching microRNA profile. As such, the cell state classifier of the present disclosure may be used for diagnosing a disease (e.g., cancer). In some embodiments, detection of the diseased cell (e.g., a cancer cell) may be coupled with the expression of a therapeutic molecule for treating a disease (e.g., cancer).

The cell state classifier described herein comprises various genetic circuits (also termed "circuits") that perform different functions. A "genetic circuit" is a functional unit of the cell state classifier. The genetic circuits of the present disclosure may function in sensing the microRNA profile, producing output molecules, producing control signal, or regulating the signals sensed or produced by the cell state classifier.

Cell State Classifier Producing Endoribonuclease-Regulated Output Signals

Some aspects of the present disclosure provide cell state classifiers comprising: (i) a first sensor circuit comprising a promoter operably linked to a nucleotide sequence encoding a first activator and one or more target sites for a first microRNA; (ii) a second sensor circuit comprising (a) a first part comprising a promoter operably linked to a nucleotide sequence encoding a second activator, and one or more target sites for a second microRNA; and (b) a second part comprising a promoter that is activated by the second activator, operably linked to a nucleotide sequence encoding an endoribonuclease, and one or more target sites for a second microRNA; and (iii) a signal circuit comprising an activatable promoter that is activated by the first activator, operably linked to a nucleotide sequence encoding a self-amplifying RNA comprising a subgenomic promoter operably linked to a nucleotide sequence encoding an output molecule, one or more target sites for the first microRNA, and a recognition site for the endoribonuclease.

A "sensor circuit" is a genetic circuit that detects the microRNA profile of the cell. Different types of sensor circuits are used in the cell state classifier for detecting microRNA-high and microRNA-low. Sensor circuits comprise microRNA target sites for the microRNAs to be detected.

The cell state classifier described herein comprises a first sensor circuit that detects a first microRNA that does not express or expresses at a low (e.g., undetectable) level in a cell. Such first microRNA is referred to as "microRNA-low" or "miR-low" herein. The first sensor circuit is also referred to interchangeably herein as the "microRNA-low sensor" or "miR-low sensor." As described herein, the first sensor circuit comprises one or more (e.g., 1, 2, 3, 4, 5, 6, 7, 8, 9, 10, or more) target sites of the first microRNA (microRNA-low) to be detected. In some embodiments, one first sensor circuit is used for the detection of one or multiple (e.g., 2, 3, 4, 5, 6, 7, 8, 9, 10, or more) microRNA-low.

Figure 2:
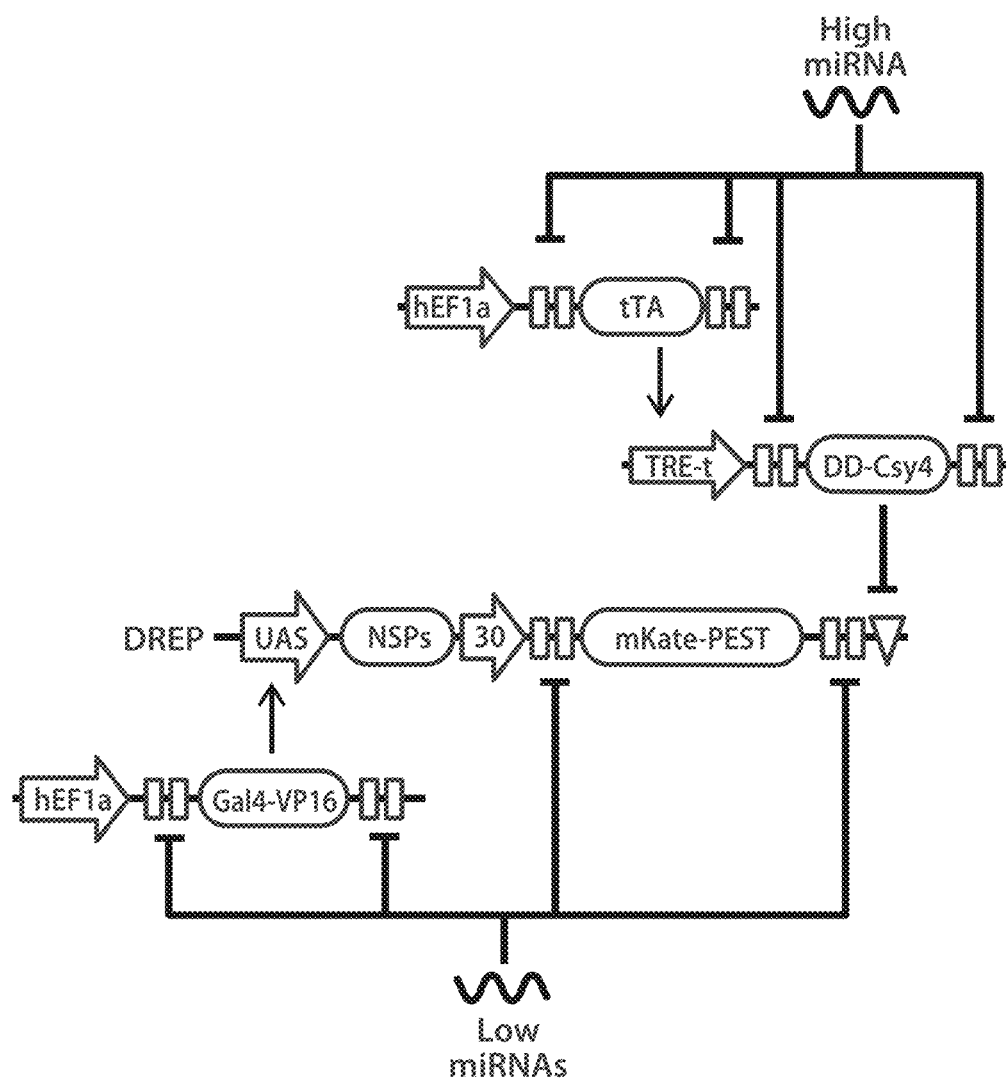
FIG. 2: Design for a miRNA classifier to control DREP expression. Payload of interest (mKate-PEST above) is expressed from the subgenomic region of a DNA-launched replicon. The DREP expression is regulated by a Gal4-VP16-inducible promoter, and by a Csy4-recognition site in the 3' UTR. Csy4 (with various degradation domains) is expressed from a TRE-tight promoter, regulated by tTA. "Low" miRNA sensors are built into the DREP payload and the Gal4-VP16 mRNA, while "high" miRNA sensors are located in the UTRs of Csy4 and tTA mRNAs.

The first sensor circuit further comprises a promoter operably linked to a nucleotide sequence encoding a first activator. In some embodiments, in the first sensor circuit, the one or more (e.g., 1, 2, 3, 4, 5, 6, 7, 8, 9, 10, or more) target sites for the first microRNA are inserted into non-coding regions of the circuit. For example, such non-coding region may be upstream and/or downstream of the nucleotide sequence encoding the first activator. In some embodiments, the target sites for the first microRNA are upstream of the nucleotide sequence encoding the first activator. In some embodiments, the target sites for the first microRNA are downstream of the nucleotide sequence encoding the first activator. In some embodiments, the target sites for the first microRNA are downstream and upstream of the nucleotide sequence encoding the first activator. In some embodiments, the first activator is Gal4-VP16, as shown in FIG. 2.

The cell state classifier comprises a second sensor circuit that detects a second microRNA that expresses at a high level (e.g., expression level is detectable by the cell state classifier or high) in a cell. Such second microRNA are referred to as "microRNA-high" or "miR-high" herein. The second sensor circuit is also referred to interchangeably herein as the "microRNA-high sensor" or "miR-high sensor."

The second sensor circuit comprises two parts that are linked together via transcriptional control. The first part of the second sensor circuit comprises one or more (e.g., 1, 2, 3, 4, 5, 6, 7, 8, 9, 10, or more) target sites of the second microRNA (microRNA-high), and a promoter operably linked to a nucleotide sequence encoding a second activator, which is different from the first activator of the first sensor circuit. In some embodiments, in the first part of the second sensor circuit, the one or more (e.g., 1, 2, 3, 4, 5, 6, 7, 8, 9, 10, or more) target sites for the second microRNA are inserted into non-coding regions of the circuit. For example, such non-coding region may be upstream and/or downstream of the nucleotide sequence encoding the second activator. In some embodiments, the target sites for the second microRNA are downstream of the nucleotide sequence encoding the second activator. In some embodiments, the target sites for the second microRNA are upstream of the nucleotide sequence encoding the second activator. In some embodiments, the target sites for the second microRNA are downstream and upstream of the nucleotide sequence encoding the second activator. In some embodiments, the promoter of the first part of the second sensor circuit is a constitutive promoter. In some embodiments, the promoter of the first part of the second sensor circuit is an inducible promoter. It is to be understood that the second activator is different from the first activator.

The second part of the second sensor circuit comprises one or more (e.g., 1, 2, 3, 4, 5, 6, 7, 8, 9, 10, or more) target sites of the second microRNA (microRNA-high), and a promoter that is activated by the second activator, operably linked to a nucleotide sequence encoding an endoribonuclease. In some embodiments, the second activator is tTA, the promoter of the second part of the second sensor circuit is TRE-t, and the endoribonuclease is Csy4, as shown in FIG. 2.

In some embodiments, in the second part of the second sensor circuit, the one or more (e.g., 1, 2, 3, 4, 5, 6, 7, 8, 9, 10, or more) target sites for the second microRNA are inserted into non-coding regions of the circuit. For example, such non-coding region may be upstream and/or downstream of the nucleotide sequence encoding the endoribonuclease. In some embodiments, the target sites for the second microRNA are downstream of the nucleotide sequence encoding the endoribonuclease. In some embodiments, the target sites for the second microRNA are upstream of the nucleotide sequence encoding the endoribonuclease. In some embodiments, the target sites for the second microRNA are downstream and upstream of the nucleotide sequence encoding the endoribonuclease.

An "endoribonuclease," as used herein, refers to an endonuclease that cleaves an RNA molecule in a sequence specific manner, e.g., at a recognition site. Site-specific RNA endoribonucleases have been described in the art. For example, the *Pyrococcus furiosus* CRISPR-associated endoribonuclease 6 (Cas6) is found to cleave RNA molecules in a site specific manner (Carte et al., *Genes & Dev.* 2008. 22: 3489-3496, incorporated herein by reference). In another example, endoribonucleases that cleave RNA molecules in a site-specific manner are engineered, which recognize an 8-nucleotide (nt) RNA sequence and make a single cleavage in the target (Choudhury et al., *Nature Communications* 3, Article number: 1147 (2012), incorporated herein by reference).

In some embodiments, the endoribonuclease belongs to the CRISPR-associated endoribonuclease 6 (Cas6) family. Cas6 nucleases from different bacterial species may be used. Non-limiting examples of Cas6 family nucleases include Cas6, Csy4 (also known as Cas6f), and Cse3 (also known as CasE). Table 1 provides the amino acid and nucleotide sequences of exemplary endoribonucleases and their respective recognition sites. In some embodiments, a trans-acting ribozyme (e.g., RNase P as shown in Table 6) can also perform the function of the endoribonuclease.

TABLE 1

Non-limiting, Exemplary Endoribonucleases and Recognition Sites

| Endoribonuclease/ Bacterial species | Amino acid sequence | Gene Sequence | Recognition site sequence |
| --- | --- | --- | --- |
| Cas6/*Pyrococcus furiosus* | MRFLIRLVPEDKDR AFKVPYNHQYYLQ GLIYNAIKSSNPKL ATYLHEVKGPKLFT YSLFMAEKREHPK GLPYFLGYKKGFFY FSTCVPEIAEALVN GLLMNPEVRLWDE RFYLHEIKVLREPK KFNGSTFVTLSPIA VTVVRKGKSYDVP PMEKEFYSIIKDDL QDKYVMAYGDKPP SEFEMEVLIAKPKR FRIKPGIYQTAWHL VFRAYGNDDLLKV GYEVGFGEKNSLG FGMVKVEGNKTTK EAEEQEKITFNSRE ELKTGV (SEQ ID NO: 1) | ATGCGCTTCCTCATTCGTCTCGTGCCT GAGGATAAGGATCGGGCCTTTAAAGT GCCATATAACCATCAGTATTACCTGC AGGGCCTCATCTATAATGCCATCAAA TCCTCCAATCCGAAGCTGGCCACCTA CCTGCATGAGGTGAAGGGTCCCAAAC TGTTCACCTACAGCCTGTTTATGGCCG AAAAACGCGAACACCCTAAGGGGCTG CCTTACTTTTTGGGGTACAAGAAGGG CTTCTTCTACTTTTCTACCTGCGTGCC GGAGATCGCTGAAGCACTGGTCAACG GACTCCTGATGAATCCAGAGGTGCGC CTGTGGGACGAACGCTTCTACCTGCA CGAAATTAAGGTTTTGAGAGAGCCTA AGAAGTTCAACGGCTCTACCTTCGTC ACCCTGTCTCCGATTGCTGTGACTGTC GTGAGGAAGGGTAAGAGTTATGATGT CCCCCCTATGGAGAAGGAGTTTTACA GTATCATCAAAGACGACCTGCAAGAT AAGTATGTGATGGCCTACGGCGACAA GCCCCCATCCGAATTCGAGATGGAGG TGCTGATTGCTAAGCCGAAACGGTTT CGTATTAAGCCTGGCATCTATCAGAC AGCCTGGCACCTGGTTTTTAGGGCCTA CGGAAACGACGACCTGCTGAAGGTTG GTTACGAGGTTGGGTTCGGAGAAAAG AACTCCCTGGGATTCGGCATGGTGAA GGTGGAGGGGAACAAGACCACAAAA GAAGCTGAAGAGCAGGAAAAGATCA CCTTCAACTCTCGCGAGGAGCTGAAG ACCGGCGTG (SEQ ID NO: 2) | GTTACAAT AAGACTAA ATAGAATT GAAAG (SEQ ID NO: 3) |
| Csy4/*Pseudomonas aeruginosa* | MDHYLDIRLRPDPE FPPAQLMSVLFGKL HQALVAQGGDRIG VSFPDLDESRSRLG ERLRIHASADDLRA LLARPWLEGLRDH LQFGEPAVVPHPTP | ATGGACCACTATCTCGACATTCGGCT GCGACCTGACCCGGAGTTTCCTCCCG CCCAACTTATGAGCGTGCTGTTCGGC AAATTGCACCAGGCCCTGGTAGCTCA AGGCGGTGACCGAATTGGAGTGAGCT TCCCTGACCTGGATGAGTCTAGGTCCC GACTGGGTGAGAGACTCAGAATCCAC | GTTCACTG CCGTATAG GCAGCTAA GAAA (SEQ ID NO: 6) |

TABLE 1-continued

Non-limiting, Exemplary Endoribonucleases and Recognition Sites

| Endoribonuclease/ Bacterial species | Amino acid sequence | Gene Sequence | Recognition site sequence |
|---|---|---|---|
| | YRQVSRVQAKSNP ERLRRRLMRRHDL SEEEARKRIPDTVA RALDLPFVTLRSQS TGQHFRLFIRHGPL QVTAEEGGFTCYG LSKGGFVFNF (SEQ ID NO: 4) | GCATCCGCCGACGACCTCAGAGCACT GCTGGCCCGCCCCTGGCTGGAGGGCC TCAGAGATCACTTGCAGTTTGGAGAG CCAGCCGTCGTGCCTCACCCTACCCCA TACAGGCAAGTGTCTAGAGTCCAGGC CAAGAGTAACCCCGAACGGCTGCGGC GGAGGTTGATGAGGCGGCACGACCTG TCCGAAGAAGAGGCACGGAAAAGAA TTCCCGACACCGTTGCTAGGGCTCTTG ATTTGCCCTTCGTCACCCTTCGATCAC AGTCCACCGGACAACATTTCCGCCTG TTCATTAGGCACGGGCCTCTGCAGGT CACTGCCGAAGAGGGCGGATTCACTT GCTACGGGCTGTCCAAGGGAGGGTTC GTTCCATGGTTCTAA (SEQ ID NO: 5) | |
| Cse3/Escherichia coli | MYLSKIIIARAWSR DLYQLHQEDATHLF PNRPDAARDFLFHV EKRNTPEGCHVLL QSAQMWVSTAVAT VIKTKQVEFQLQVG VPLYFRLRANPIKTI LDNQKRLDSKGNI KRCRVPLIKEAEQI AWLQRKLGNAAR VEDVHPISERPQYF SGEGKNGKIQTVCF EGVLTINDAPALID LLQQGIGPAKSMG CGLLSLAPL (SEQ ID NO: 7) | ATGTACCTCAGTAAGATCATCATCGC CCGCGCTTGGTCCCGTGACCTGTACCA ACTGCACCAAGAGCTCTGGCACCTCT TCCCCAACAGGCCAGATGCCGCTAGA GACTTCCTGTTCCACGTGGAGAAGCG TAACACCCCCGAAGGGTGCCACGTGC TGTTGCAGAGTGCCCAGATGCCAGTG AGTACCGCTGTTGCCACTGTCATCAA GACTAAACAAGTTGAATTCCAACTGC AAGTGGGCGTCCCTCTGTATTTCCGCC TCAGGGCCAACCCCATCAAAACCATC CTGGACAACCAGAAGCGGCTGGATAG CAAAGGTAATATCAAGAGATGCCGCG TGCCTCTGATCAAGGAGGCCGAGCAG ATCGCTTGGCTGCAACGCAAGCTGGG TAACGCCGCGAGAGTGGAAGATGTGC ACCCAATCTCCGAGCGCCCGCAGTAT TTCTCCGGGGAGGGGAAGAACGGCAA AATTCAGACTGTCTGCTTCGAGGGGG TGCTCACTATTAACGACGCCCCTGCTC TGATCGACCTCCTGCAGCAGGGCATT GGGCCCGCGAAGAGCATGGGATGCGG ATTGTTGAGCCTGGCACCCCTG (SEQ ID NO: 8) | GTAGTCCC CACGCGTG TGGGGATG GACCG (SEQ ID NO: 9) |

In some embodiments, the strength of the endoribonuclease is tuned, such that the inhibition level of the endoribonuclease on the signal circuit is tuned. For example, in some embodiments, the endoribonuclease (e.g., Csy4) may be fused to a degradation domain, such that its cellular-half life is reduced (e.g., by at least 20%, at least 30%, at last 40%, at least 50%, at least 60%, at least 70%, at least 80% or more). In some embodiments, reducing the half-life of the endoribonuclease reduces its activity (e.g., by at least 20%, at least 30%, at last 40%, at least 50%, at least 60%, at least 70%, at least 80% or more).

A "degradation domain," as used herein, refers to a protein domain or motif, which, when fused to another protein or polypeptide, directs the protein or polypeptide to degradation, e.g., by the proteasome, thus reducing the cellular half-life of the protein or polypeptide. Such degradation domains are known in the art. For example, a PEST sequence may be fused to the endoribonuclease (e.g., Csy4) to direct it to degradation. A "PEST sequence" is a peptide sequence that is rich in proline (P), glutamic acid (E), serine (S), and threonine (T) and associated with proteins that have a short intracellular half-life, e.g., as described in Roger et al., *Science.* 234 (4774): 364-8, 1986, incorporated herein by reference. Other known degradation domains may also be used, e.g., the DDd degradation, or the DDe degradation domain. Non-limiting, exemplary degradation domains and sequences are provided in Table 2.

TABLE 2

Non-limiting, Exemplary Degradation Domains

| Degradation Domain | Amino Acid Sequence |
|---|---|
| PEST | KLSHGFPPEVEEQDDGTLPMSCAQESGMDRHPAACASARINV (SEQ ID NO: 10) |
| DDd | MISLIAALAVDYVIGMENAMPWNLPADLAWFKRNTLNKPVIMGRHTWESIGRPLPGRKN IILSSQPSTDDRVTWVKSVDEAIAACGDVPEIMVIGGGRVIEQFLPKAQKLYLTHIDAEVE GDTHFPDYEPDDWESVFSEFHDADAQNSHSYCFEILERR (SEQ ID NO: 11) |

TABLE 2-continued

Non-limiting, Exemplary Degradation Domains

| Degradation Domain | Amino Acid Sequence |
|---|---|
| DDe | MSLALSLTADQMVSALLDAEPPILYSEYDPTRPFSEASMMGLLTNLADRELVHMINWAK RVPGFVDLALHDQVHLLECAWMEILMIGLVWRSMEHPGKLLFAPNLLLDRNQGKCVEG GVEIFDMLLATSSRFRMMNLQGEEFVCLKSIILLNSGVYTFLSSTLKSLEEKDHIHRVLDKI TDTLIHLMAKAGLTLQQQHQRLAQLLLILSHIRHMSSKRMEHLYSMKCKNVVPLSDLLL EMLDAHRL (SEQ ID NO: 12) |

The cell state classifier described herein further comprises a signal circuit. A "signal circuit," as used herein, refers to a genetic circuit that responds to the sensor circuits and in turn produces an output molecule. The signal circuit of the present disclosure comprises an activatable promoter operably linked to a nucleotide sequence encoding a self-amplifying RNA replicon. An "activatable promoter" is a promoter that can be activated (e.g., by an activator) to drive the expression of the nucleotide sequence that it is operably linked to. The activatable promoter of the signal circuit is activated by the first activator of the first sensor circuit.

A "self-amplifying RNA," as used herein, refers to an RNA molecule that can amplify itself in a host cell, leading to an amplification of the amount of RNA encoding the desired gene product and enhanced efficiency of expression of the encoded gene products (e.g., the output molecule). Such self-amplifying RNA molecules are also interchangeably herein as "replicons." The self-amplifying RNA of the present disclosure may be encoded on a DNA molecule (e.g., the signal circuit described herein) and placed under control of an activatable promoter. Activation of the activatable promoter (e.g., by the second activator) leads to the production of the self-amplifying RNA. As such, the self-amplifying RNA is also referred to as a "DNA-launched replicon" (DREP).

Self-amplifying RNAs are found in positive-strand RNA viruses and use their own encoded viral polymerase to amplify itself, e.g., as described in Johanning et al., *Nucleic Acids Res.*, 23(9):1495-1501 (1995); and Khromykh et al., *Current Opinion in Molecular Therapeutics*, 2(5):556-570 (2000); Smerdou et al., *Current Opinion in Molecular Therapeutics*, 1(2):244-251 (1999), incorporated herein by reference.

A "positive-strand RNA virus" is a virus that uses positive sense, single-stranded RNA as its genetic material. The self-amplifying RNA of the present disclosure comprises nucleotide sequences encoding all the components it needs for self-amplification, e.g., a replicase and/or transcriptase. The replicase is translated as a polyprotein which autocleaves to provide a replication complex, which creates genomic negative-strand copies of the positive-strand RNA. The genomic strand transcripts can themselves be transcribed to give further copies of the positive-stranded parent RNA (i.e., amplification) and also to yield large amounts of subgenomic mRNAs from which large amounts of a molecule of interest can be expressed.

In some embodiments, the self-replicating RNA molecules described herein are derived from alphaviruses. Non-limiting examples of alphaviruses includes, without limitation, a Sindbis virus, a Semliki Forest virus, an eastern equine encephalitis virus, a Venezuelan equine encephalitis virus, etc. In some embodiments, a replicons derived from one species of alphavirus can use a replicase from a different alphavirus.

Suitable wild-type alphavirus sequences are known in the art and are available from sequence depositories, such as the American Type Culture Collection, Rockville, Md. Non-limiting examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

While natural alphavirus genomes encode structural virion proteins in addition to the non-structural replicase polyprotein, the self-amplifying RNA of the present disclosure, in some embodiments, do not encode alphavirus structural proteins. Thus, the self-amplifying RNA can lead to the production of genomic RNA copies of itself in a cell, but not to the production of RNA-containing alphavirus virions and cannot perpetuate itself in infectious form.

In some embodiments, the self-amplifying RNA of the present disclosure is derived from a positive-strand RNA virus that is not an alphavirus, e.g., without limitation, picornavirus, flavivirus, rubivirus, pestivirus, hepacivirus, calicivirus, or coronavirus.

The self-amplifying RNAs of the present disclosure comprises a subgenomic promoter operably linked to a nucleotide sequence encoding an output molecule. A "subgenomic promoter," as used herein, refers to a promoter added to an RNA molecule (e.g., a positive strand viral RNA) to drive the expression of a gene of interest alone. In the context of a virus, the gene of interest is typically heterologous to the virus. The gene of interest of the present disclosure is the output molecule. Non-limiting examples of subgenomic promoters that may be used in accordance with the present disclosure include: SGP3, SGP5, SGP15, and SGP30. In some embodiments, the subgenomic promoter is SGP30. Non-limiting, exemplary subgenomic promoters and sequences are provided in Table 3.

TABLE 3

Non-limiting, Exemplary Sub genomic Promoters

| Subgenomic Promoters | Nucleotide Sequences |
|---|---|
| SGP3 | ACTTCCATCATAGTTATGGCCATGACTACTCTAGCTAGCAGTGTTAAATCATTCAG CTACCTGAGAGGGGCCCCTATAACTCTCTACGGCTAACCTGAATG (SEQ ID NO: 13) |
| SGP5 | ACTTCCATCATAGTTATGGCCATGACTACTCTAGCTAGCAGTGTTAAATCATTCAG CTACCTGAGAGGGGCCCCTATAACTCTCTACGGCTAACCTGAATGGA (SEQ ID NO: 14) |
| SGP15 | ACTTCCATCATAGTTATGGCCATGACTACTCTAGCTAGCAGTGTTAAATCATTCAG CTACCTGAGAGGGGCCCCTATAACTCTCTACGGCTAACCTGAATGGACTACGACA TA (SEQ ID NO: 15) |
| SGP30 | ACTTCCATCATAGTTATGGCCATGACTACTCTAGCTAGCAGTGTTAAATCATTCAG CTACCTGAGAGGGGCCCCTATAACTCTCTACGGCTAACCTGAATGGACTACGACA TAGTCTAGTCCGCCAAG (SEQ ID NO: 16) |

The self-amplifying RNA of the present disclosure comprises one or more (e.g., 1, 2, 3, 4, 5, 6, 7, 8, 9, 10, or more) target sites for the first microRNA (microRNA-low). In some embodiments, the first microRNA target sites are downstream of the nucleotide sequence encoding the output molecule. In some embodiments, the first microRNA target sites are upstream of the nucleotide sequence encoding the output molecule. In some embodiments, the first microRNA target sites are downstream and upstream of the nucleotide sequence encoding the output molecule.

The self-amplifying RNA of the present disclosure further comprises a recognition site for the endoribonuclease encoded by the second part of the second sensor circuit. A "recognition site for an endoribonuclease" refers to a ribonucleotide sequence that is recognized, bound, and cleaved by the endoribonuclease. The recognition site for an endoribonuclease may be 4-20 nucleotides long. For example, the recognition site may be 4, 5, 6, 7, 8, 9, 10, 11, 12, 13, 14, 15, 16, 17, 18, 19, or 20 nucleotides long. In some embodiments, endoribonuclease recognition sites that are shorter than 4 ribonucleotides or longer than 20 nucleotides are used. Non-limiting exemplary endoribonucleases and their respective recognition sites are provided in Table 1. In some embodiments, the recognition site is placed inside the nucleotide sequence encoding the self-amplifying RNA. In some embodiments, the recognition site is placed in a non-coding region within the nucleotide sequence under control of the subgenomic promoter. For example, the recognition site may be placed between the subgenomic promoter and the nucleotide sequence encoding the output molecule, or downstream of the nucleotide sequence encoding the output molecule.

In some embodiments, the cell state classifier of the present disclosure further comprises a control circuit. A "control circuit" refers to a circuit that produces a constant signal independent of the input (e.g., the microRNA profile of a cell) and may be used to control for variations caused by other factors other than the microRNA profile, e.g., transfection, cellular health, etc. The control circuit comprises a constitutive promoter operably linked to a nucleotide sequence encoding a control signal that is different from the first output molecule or the second output molecule. The control signal is typically a detectable molecule such as a fluorescent molecule.

Further provided herein are the functionalities of the cell state classifiers and methods of using them. In some embodiments, the methods comprising delivering the cell state classifiers described herein into a cell (e.g., by any of the methods described herein and known to one skilled in the art). In some embodiments, the methods comprises maintaining the cell containing the cell state classifiers. In some embodiments, the maintaining is carried out under conditions to allow the cell state classifier to function. In some embodiments, the presence of the cell state classifier in the cell does not change the native microRNA profile of the cell.

Once introduced into a cell that has a detectable microRNA profile, the cell state classifier described herein is able to detect the microRNAs in the cell and produce an output (e.g., a detectable molecule or a therapeutic molecule) accordingly. In some embodiments, no microRNA input is detected. For example, this may occur if none of the microRNAs the cell state classifier is designed to detect (either microRNA-high or microRNA-low) are expressed in the cell (e.g., expression level is not detectable). As such, the first activator is expressed in the absence of microRNA-low inhibition, leading to the production of the self-amplifying RNA molecule in the signal circuit, which contains the recognition sites for the endoribonuclease. Further, in the absence of the microRNA-high inhibition, the second activator expresses, activating the expression of the endoribonuclease. The endoribonuclease recognizes and cleaves at its recognition sites in the self-amplifying RNA, leading to degradation of the RNA molecule and no expression of the output molecule.

In some embodiments, the first microRNA expresses (e.g., has a detectable expression level by the cell state classifier), and the first activator in the first sensor circuit (e.g., Gal4-VP16 in FIG. 2) does not express because the first microRNA mediate the degradation of the mRNA encoding the first activator (translational control). As such, the activatable promoter of the signal circuit is not activated, leading to no expression of the output molecule (e.g., mKate-PEST in FIG. 2).

In some embodiments, the second microRNA (microRNA-high) expresses (e.g., has a detectable expression level by the cell state classifier) or has a high expression level, and thus the second activator in the first part of the second sensor circuit (e.g., tTA in FIG. 2) does not express, because the second microRNA mediates the degradation of the mRNA encoding the second activator (translational control). As a result, the endoribonuclease (e.g., DD-Csy4 in FIG. 2) does not express in the absence of transcriptional activation by the second activator. Without the endoribonuclease, the self-amplifying RNA molecule produced from the signal circuit (e.g., when the first microRNA also does not express) is not cleaved by the endoribonuclease and not degraded. The self-amplifying RNA then self-amplifies, leading to high level expression of the output molecule.

Figure 1B:
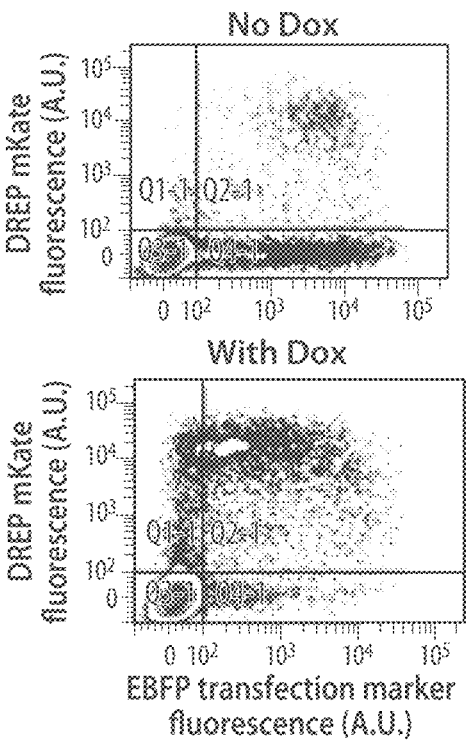

The expression of the output molecule encoded by the self-amplifying RNA is tightly regulated, both translationally and by the endoribonuclease. As demonstrated herein, e.g., in FIG. 1C, the presence of the endoribonuclease (Csy4) nearly completely repressed the expression of the output molecule (mKate) encoded on the self-amplifying RNA. Conversely, when the self-amplifying RNA is expressed but the endoribonuclease is absent, high levels of the output molecule is produced (FIG. 1B).

In some embodiments, the cell state classifier detects the expression of the first set of microRNAs (microRNA-low) and the expression of the second set of microRNAs (microRNA-high), e.g., via microRNA binding sites in the first or second sensor circuits. As such, the cell state classifier also has a logic function, where the cell state classifier produces an output molecule only when a matching microRNA profile is detected. In some embodiments, a matching microRNA profile comprises: (i) the first microRNAs (microRNA-low) does not express or the expression level is low (e.g., undetectable by the cell state classifier); and (ii) the expression level of the second microRNA (microRNA-high) is high (e.g., at least detectable by the cell state classifier), and the output molecule is produced by the cell state classifier. In some embodiments, the first microRNA (microRNA low) expresses (e.g., expression level is detectable by the cell state classifier) or has high expression level, and the second microRNA (microRNA-high) does not express (e.g., expression level is not detectable by the cell state classifier), and no output molecule or very low output molecule is produced by the cell state classifier. In some embodiments, the first microRNA does not express or the expression level is low (e.g., expression level is not detectable by the cell state classifier), and the second microRNAs (microRNA-high) does not express or the expression level is low (e.g., expression level is not detectable by the cell state classifier), and no output molecule or very low output molecule is produced by the cell state classifier. In some embodiments, the first microRNAs (microRNA low) expresses (e.g., expression level is detectable by the cell state classifier) or has high expression level, and the second microRNA expresses or has high expression level, and no output molecule or very low output molecule is produced by the cell state classifier.

By placing the target sites for the first or second microRNA (microRNA-low or microRNA-high) in different circuits of the cell state classifier, additional functions of the cell state classifiers can be provided. For example, if the first sensor circuit comprises target sites for the second microRNA (miRNA-high) and the second sensor circuit comprising target sites for the first microRNA (miRNA-low), then the output of the cell state classifier circuit would be reversed such that output would be produced only in cells in which miRNA-low, but not miRNA-high, is expressed.

In some embodiments, to classify the cell, the method further comprises detecting an output molecule produced by the cell state classifier. For example, the output molecule may be a fluorescent protein or an enzyme that acts on a substrate to produce a detectable molecule. One skilled in the art is familiar with methods of detecting different detectable molecules.

Cell State Classifier Encoded by a Single RNA Transcript

Other aspects of the present disclosure provide cell state classifiers that are encoded on a single RNA transcript. Such cell state classifiers include a promoter operably linked to a nucleic acid molecule, which when transcribed, generates a single RNA transcript containing all the components required for a functional cell state classifier.

The nucleic acid molecule described herein comprises a first sensor circuit and a second sensor circuit downstream of the first sensor circuit, separated by a splitter. The first and second sensor circuits are transcribed as a single RNA transcript, but are split post-transcription such that the first and second sensor circuits are separated, allowing for independent regulation of the different components of the cell state classifier (e.g., the RNA repressor or the output molecule). "Splitting" of the first and second sensor circuits is achieved via cleavage of the initial RNA transcript within the splitter (e.g., by an endoribonuclease or a ribozyme). RNA stabilizers are needed at the cleaved 5' and 3' ends to prevent the cleaved fragments from degradation.

Figure 3A:
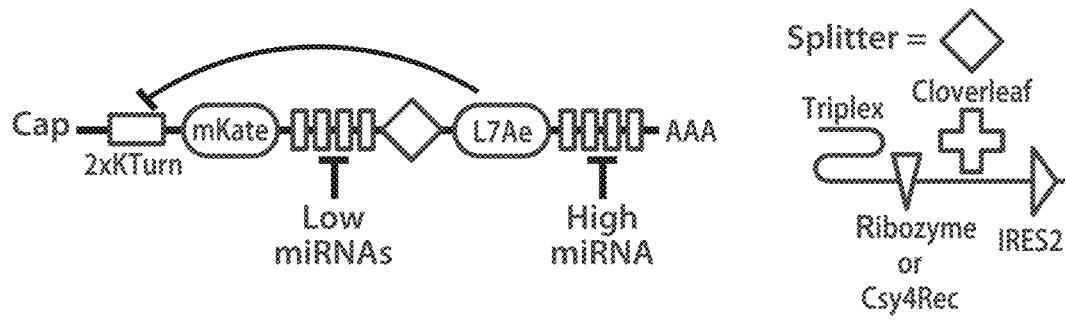
FIGS. 3A-3C: Design for a miRNA classifier encoded as a single transcript. Shown here are the RNA version of the miRNA classifier, which may be encoded by a DNA version of the microRNA classifier and placed under the control of a promoter.
Figure 3B:
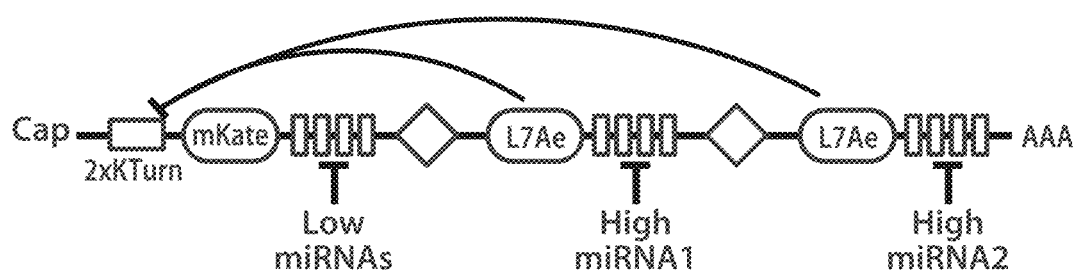
Figure 3C:
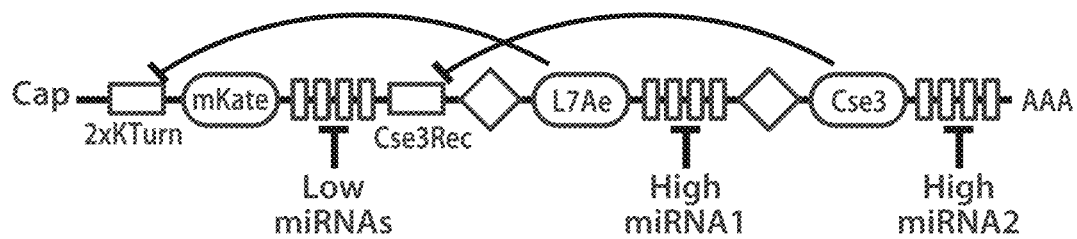

The first sensor circuit comprises one or more (e.g., 1, 2, 3, 4, 5, 6, 7, 8, 9, 10, or more) binding sites for a RNA repressor, operably linked to a nucleotide sequence encoding an output molecule, and one or more (e.g., 1, 2, 3, 4, 5, 6, 7, 8, 9, 10, or more) target sites for a first microRNA (microRNA-low). In some embodiments, the second sensor circuit is downstream (3') of the first sensor circuit (e.g., as shown in FIGS. 3A-3C), and comprises a nucleotide sequence encoding the RNA repressor and one or more target sites for a second microRNA.

A "RNA repressor," as used herein, refers to a protein that inhibits the expression of the output molecule. Inhibition of output molecule expression may be achieved via different methods. For example, one or more recognition sites of a RNA binding protein may be placed upstream of and are operably linked to the nucleotide sequence encoding the output molecule, and binding of RNA binding proteins to the recognition sites can block translation. The one or more recognition sites of the RNA binding protein are "operably linked to" the nucleotide sequence encoding the output molecule, when binding of the RNA binding protein to the recognition sites can inhibit the expression of the output molecule. In another example, cleavage and degradation of the mRNA by an endoribonuclease inhibits expression of the output molecule.

In some embodiments, the RNA repressor is a RNA binding protein. A "RNA binding protein," as used herein, refers to a protein that bind to RNA (i.e., "target sites"). The binding of a RNA binding protein to RNA may be dependent on the RNA sequence, or the structure of the RNA. As such, the targets sites of the RNA binding protein, may comprise a specific sequence motif, or form a specific structure (e.g., a stem-loop structure). Any RNA binding protein may be used as the RNA repressor of the present disclosure. Non-limiting examples of RNA binding proteins and their respective target site sequences are provided in Table 4.

TABLE 4

Non-limiting Examples of RNA Binding Proteins and Target Sites

| RNA binding protein | Amino acid sequence | Gene sequence | Target site sequence |
|---|---|---|---|
| TetR | MSRLDKSKVINSALELLN EVGIEGLTTRKLAQKLGV EQPTLYWHVKNKRALLD ALAIEMLDRHHTHFCPLE GESWQDFLRNNAKSFRC ALLSHRDGAKVHLGTRPT EKQYETLENQLAFLCQQG FSLENALYALSAVGHFTL GCVLEDQEHQVAKEERET PTTDSMPPLLRQAIELFDH QGAEPAFLFGLELIICGLE KQLKCESGS (SEQ ID NO: 17) | ATGTCAAGACTCGACAAGAGCAAGGTGATT AACAGTGCACTGGAACTTCTCAATGAAGTT GGGATCGAGGGGCTGACTACTAGAAAACT CGCACAGAAACTGGGGGTTGAGCAGCCCA CCTTGTACTGGCACGTTAAAAACAAAAGGG CCCTGCTGGATGCTCTGGCCATCGAGATGC TGGATAGGCATCATACCCACTTCTGCCCTC TGGAAGGAGAATCCTGGCAGGATTTCCTTA GAAACAACGCCAAGTCCTTTCGCTGTGCTC TTCTTAGCCACCGGGATGGTGCTAAAGTCC ATCTCGGCACACGACCAACTGAGAAGCAGT ACGAAACTCTCGAGAACCAGCTGGCCTTTC TCTGTCAACAGGGCTTTTCTCTTGAAAACG CCCTGTACGCACTGAGTGCAGTTGGGCACT TTACACTCGGATGTGTTCTGGAGGACCAAG AACATCAGGTGGCAAAGGAAGAGAGGGAG ACCCCTACGACTGACTCCATGCCCCCTCTCT TGAGGCAGGCAATAGAATTGTTCGACCATC AGGGCGCAGAACCCGCCTTTCTGTTTGGGC TGGAACTGATTATCTGCGGTCTTGAGAAAC AGCTGAAGTGCGAGTCCGGGAGC (SEQ ID NO: 18) | ATCCAGG CAGAGAA AGGTCGA TACGGAC GGAATGT GGTGCC GGTGTCA TGGATCA ACAACAA CAAAATC CAGGCAG AGAAAGG TCGATAC GGACGGA ATGTGGT GGCCTGG ATCAACA ACAACAA CACTG (SEQ ID NO: 19) |
| PPR10 | MLPLDSLLLHLTAPAPAP APAPRRSHQTPTPPHSFLS PDAQVLVLAISSHPLPTLA AFLASRRDELLRADITSLL KALELSGHWEWALALLR WAGKEGAADASALEMV VRALGREGQHDAVCALL DETPLPPGSRLDVRAYTT VLHALSRAGRYERALELF AELRRQGVAPTLVTYNV VLDVYGRMGRSWPRIVA LLDEM RAAGVEPDGFTASTVIAA CCRDGLVDEAVAFFEDLK ARGHAPCVVTYNALLQV FGKAGNYTEALRVLGEM EQNGCQPDAVTYNELAG TYARAGFFEEAAR (SEQ ID NO: 20) | ATGCTCCCTTGGACAGTCTCCTGCTGCATC TCACCGCCCCCGCCCCGCCCCAGCCCCTG CTCCAAGAAGGTCTCATCAAACGCCGACCC CCCCTCACAGCTTCCTGTCCCCTGATGCTCA GGTGTTGGTACTCGCAATCAGTTCTCACCC TCTGCCTACCCTGGCTGCTTTCCTCGCTAGC AGGCGGGATGAGTTGCTGAGGGCCGATATC ACCTCTCTCCTTAAGGCACTTGAGCTGTCTG GGCACTGGGAATGGGCATTGGCCCTTCTGC GATGGGCAGGTAAGGAGGGAGCTGCCGAT GCTAGCGCTTTGGAGATGGTCGTAAGAGCA CTCGGTAGAGAAGGCCAGCATGACGCAGT CTGTGCTCTGCTGGACGAAACTCCATTGCC TCCAGGCAGCAGACTGGACGTACGGGCCTA CACCACCGTGCTTCACGCCCTCTCAAGAGC CGGTAGGTACGAGAGAGCTCTCGAGCTGTT CGCTGAACTCAGAAGACAGGGCGTGGCCC CAACCTTGGTAACTTATAACGTGGTACTGG ACGTCTACGGCCGAATGGGGAGAAGTTGG CCGCGCATCGTCGCATTGCTCGACGAAATG CGGGCCGCAGGCGTCGAGCCAGATGGGTTT ACCGCAAGCACGGTGATCGCTGCTTGCTGC CGGGATGGTTTGGTGGATGAAGCCGTGGCC TTCTTTGAGGACTTGAAGGCCAGGGGTCAC GCACCTTGTGTCGTAACCTATAACGCACTG TTGCAGGTGTTCGGCAAGGCTGGGAATTAT ACTGAGGCCCTGAGAGTTCTTGGCGAAATG GAGCAGAACGGGTGCCAGCCAGATGCTGT GACATATAATGAGCTGGCCGGAACCTACGC ACGCGCCGGCTTCTTTGAGGAGGCCGCCCG GTGTCTGGACACGATGGCCAGTAAGGGCCT GCTTCCTAACGCATTCACATACAATACCGT GATGACAGCATATGGAAATGTGGGGAAGG TCGACGAAGCTCTCGCCCTTTTCGATCAGA TGAAAAAGACTGGCTTCGTTCCCAACGTGA ACACGTACAACCTGGTCCTGGGGATGCTGG GAAAGAAATCAAGATTCACGGTAATGTTGG AAATGTTGGGCGAAATGAGCAGGTCAGGA TGTACCCCTAACAGGGTTACTTGGAATACT ATGCTCGCTGTGTGTGGAAAGCGAGGGATG GAAGATTACGTGACACGGGTTCTGGAGGGC ATGCGGAGTTGCGGTGTCGAGCTGTCCCGA GACACATACAACACCCTCATCGCTGCTTAT GGGAGGTGCGGTAGCCGGACAAATGCTTTT AAGATGTATAACGAAATGACGTCCGCAGG GTTCACTCCCTGCATCACTACATATAACGC TCTGCTGAATGTGCTCTCTCGGCAAGGAGA CTGGTCCACTGCTCAGTCAATCGTTTCAAA GATGCGGACTAAGGGCTTTAAGCCCAACGA GCAATCTTACTCACTCCTCCTGCAGTGTTAC GCAAAGGGGGGCAATGTGGCAGGAATTGC | ATTGTAT CCTTAAC CATTTCTT TTATTGT ATCCTTA ACCATTT CTTT (SEQ ID NO: 22) |

TABLE 4-continued

Non-limiting Examples of RNA Binding Proteins and Target Sites

| RNA binding protein | Amino acid sequence | Gene sequence | Target site sequence |
|---|---|---|---|
| | | AGCCATCGAAAACGAAGTTTACGGGTCCGG CGCTGTTTTCCCATCTTGGGTGATCCTGAGG ACTCTTGTAATCGCTAATTTCAAATGTCGCC GCTTGGACGGCATGGAAACTGCTTTCCAGG AGGTAAAGGCCAGGGGGTATAATCCTGATT TGGTGATATTCAACTCAATGCTTTCCATCTA CGCTAAGAATGGTATGTATAGCAAAGCAAC TGAGGTCTTCGACTCAATTAAGAGGTCAGG TCTGTCCCAGACCTTATAACTTACAATTCC TTGATGGATATGTATGCCAAGTGTAGCGAG TCCTGGGAAGCTGAAAAGATTCTTAATCAG CTGAAATGTTCCCAGACTATGAAGCCCGAT GTTGTTAGCTATAATACAGTTATCAACGGA TTCTGCAAACAGGGCCTTGTGAAAGAAGCC CAGAGAGTGCTGTCCGAAATGGTCGCCGAC GGCATGGCTCCTTGCGCTGTGACCTACCAT ACATTGGTCGGCGGCTATTCCTCTCTCGAG ATGTTCTCCGAGGCCAGGGAGGTCATCGGC TACATGGTGCAACATGGACTGAAACCTATG GAACTGACCTATAGGAGGGTGGTGGAATC ATACTGCAGAGCCAAGCGATTCGAGGAAG CTCGGGGTTTCCTGTCCGAAGTGTCTGAGA CTGATCTGGACTTCGACAAAAAAGCTTTGG AAGCATACATCGAGGACGCTCAATTTGGGC GCTA (SEQ ID NO: 21) | |
| MS2CP | MASNFTQFVLVDNGGTG DVTVAPSNFANGVAEWIS SNSRSQAYKVTCSVRQSS AQKRKYTIKVEVPKVATQ TVGGEELPVAGWRSYLN MELTIPIFATNSDCELIVK AMQGLLKDGNPIPSAIAA NSGIY (SEQ ID NO: 23) | ATGGCTTCTAACTTTACTCAGTTCGTTCTCG TCGACAATGGCGGAACTGGCGACGTGACTG TCGCCCCAAGCAACTTCGCTAACGGGGTCG CTGAATGGATCAGCTCTAACTCGCGTTCAC AGGCTTACAAAGTAACCTGTAGCGTTCGTC AGAGCTCTGCGCAGAAGCGCAAATACACC ATCAAAGTCGAGGTGCCTAAAGTGGCAACC CAGACTGTTGGTGGTGAGGAGCTTCCTGTA GCCGGTTGGCGTTCGTACTTAAATATGGAA CTAACCATTCCAATTTTCGCCACGAATTCC GACTGCGAGCTTATTGTTAAGGCAATGCAA GGCCTCCTAAAAGATGGAAACCCGATTCCC TCGGCCATCGCAGCAAACTCCGGCATCTAC (SEQ ID NO: 24) | ACATGAG GATCACC CATGTCT GCAGGTC GACTCTA GAAAACA TGAGGAT CACCCAT GTCCTGC AGGTCGA CTCTAGA AA (SEQ ID NO: 25) |
| L7Ae | MYVRFEVPEDMQNEALS LLEKVRESGKVKKGTNET TKAVERGLAKLVYIAEDV DPPEIVAHLPLLCEEKNVP YIYVKSKNDLGRAVGIEV PCASAAIINEGELRKELGS LVEKIKGLQK (SEQ ID NO: 26) | ATGTACGTGAGATTTGAGGTTCCTGAGGAC ATGCAGAACGAAGCTCTGAGTCTGCTGGAG AAGGTTAGGGAGAGCGGTAAGGTAAAGAA AGGTACCAACGAGACGACAAAGGCTGTGG AGAGGGGACTGGCAAAGCTCGTTTACATCG CAGAGGATGTTGACCCGCCTGAGATCGTTG CTCATCTGCCCCTCCTCTGCGAGGAGAAGA ATGTGCCGTACATTTACGTTAAAAGCAAGA ACGACCTTGGAAGGGCTGTGGGCATTGAGG TGCCATGCGCTTCGGCAGCGATAATCAACG AGGGAGAGCTGAGAAAGGAGCTTGGAAGC CTTGTGGAGAAGATTAAAGGCCTTCAGAAG (SEQ ID NO: 27) | GGGCGTG ATCCGAA AGGTGAC CCGGATC TGGGGCG TGATCCG AAAGGTG ACCCGGA TCCACCG GTC (SEQ ID NO: 28) |

In some embodiments, to repress translation, the recognition sites of RNA binding proteins are placed upstream of the coding sequence. For example, in some embodiments, the one or more (e.g., 1, 2, 3, 4, 6, 7, 8, 9, 10 or more) recognition sites of the RNA binding protein is placed immediately upstream (no spacer between them) of the nucleotide sequence encoding the output molecule. The start of the coding sequence is marked by a start codon, usually AUG. In some embodiments, the one or more (e.g., 1, 2, 3, 4, 6, 7, 8, 9, 10 or more) recognition sites of the RNA binding protein is placed upstream of the nucleotide sequence encoding the output molecule and is separated by a ribonucleotide spacer. The ribonucleotide spacer may be 2-30 nucleotides long. For example, the ribonucleotide spacer may be 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides long. Shorter and longer ribonucleotide spacers may also be used. In some embodiments, the binding of RNA binding proteins to the recognition sites blocks translation. In some embodiments, translation is blocked via inhibition of translation initiation.

In some embodiments, the RNA repressor is fused to a modifying domain. A "modifying domain" as used herein, refers to a protein or polypeptide, or a functional domain thereof, that is capable to modify a ribonucleoprotein complex formed between the RNA molecule and the RNA binding protein. The modification may be to the ribonucleotide bases (with or without changing the ribonucleotide sequence), to the structure of the RNA molecule containing the RNA binding protein target sites, or the remodeling of the ribonucleoprotein complex. Such modifying domains have been described in the art. For example, Cooke et al. (*J Biol Chem.* 285(37): 28506-28513, 2010, incorporated herein by reference) describes a CCR4-CAF1-NOT deadenylation complex that, when associated with RNA binding proteins, represses translation in mammalian cells. Cooke further demonstrates that CAF1 (also known as CNOT7) represses translation independent of deadenylation. In another example, Weston et al. (*Nucleic Acids Res.* 34(10): 3082-3094, 2006, incorporated herein by reference) demonstrates that DEAD-box RNA helicase family proteins (e.g., DDX6, Xp54, etc.) play key roles in mRNA degradation and in earlier remodeling of messenger ribonucleoprotein complexes during translation initiation. Accordingly, in some embodiments, the RNA binding protein is fused to a CNOT7 protein. In some embodiments, the RNA binding protein is fused a DEAD-box RNA helicase protein (e.g., DDX6, or Xp54). The amino acid and nucleotide sequences of non-limiting, exemplary modifying domains are provided in Table 5.

TABLE 5

Non-limiting, Exemplary Modifying Domains for Translation Repression

| Modifying domain | Amino acid sequence | Nucleotide sequence (cDNA) |
|---|---|---|
| CNOT7 | MPAATVDHSQRICEVWACN LDEEMKKIRQVIRKYNYVA MDTEFPGVVARPIGEFRSNA DYQYQLLRCNVDLLKIIQLG LTFMNEQGEYPPGTSTWQF NFKFNLTEDMYAQDSIELLT TSGIQFKKHEEEGIETQYFA ELLMTSGVVLCEGVKWLSF HSGYDFGYLIKILTNSNLPEE ELDFFEILRLFFPVIYDVKYL MKSCKNLKGGLQEVAEQLE LERIGPQHQAGSDSLLTGM AFFKMREMFFEDHIDDAKY CGHLYGLGSGSSYVQNGTG NAYEEEANKQSV (SEQ ID NO: 29) | ATGCCAGCGGCAACTGTAGATCATAGCCAAAGAAT TTGTGAAGTTTGGGCTTGCAACTTGGATGAAGAGAT GAAGAAAATTCGTCAAGTTATCCGAAAATATAATTA CGTTGCTATGGACACCGAGTTTCCAGGTGTGGTTGC AAGACCCATTGGAGAATTCAGGAGCAATGCTGACT ATCAATACCAACTATTGCGGTGTAATGTAGACTTGT TAAAGATAATTCAGCTAGGACTGACATTTATGAATG AGCAAGGAGAATACCCTCCAGGAACTTCAACTTGG CAGTTTAATTTTAAATTTAATTTGACGGAGGACATG TATGCCCAGGACTCTATAGAGCTACTAACAACATCT GGTATCCAGTTTAAAAAACATGAGGAGGAAGGAAT TGAAACCCAGTACTTTGCAGAACTTCTTATGACTTC TGGAGTGGTCCTCTGTGAAGGGGTCAAATGGTTGTC ATTTCATAGCGGTTACGACTTTGGCTACTTAATCAA AATCCTAACCAACTCTAACTTGCCTGAAGAAGAACT TGACTTCTTTGAGATCCTTCGATTGTTTTTTCCTGTC ATTTATGATGTGAAGTACCTCATGAAGAGCTGCAAA AATCTCAAAGGTGGATTACAGGAGGTGGCAGAACA GTTAGAGCTGGAACGGATAGGACCACAACATCAGG CAGGATCTGATTCATTGCTCACAGGAATGGCCTTTT TCAAAATGAGAGAAATGTTCTTTGAAGATCATATTG ATGATGCCAAATATTGTGGTCATTTGTATGGCCTTG GTTCTGGTTCATCCTATGTACAGAATGGCACAGGGA ATGCATATGAAGAGGAAGCCAACAAGCAGTCAGTT (SEQ ID NO: 30) |
| DDX6 | MSTARTENPVIMGLSSQNG QLRGPVKASAGPGGGGTQP QPQLNQLKNTSTINNGTPQQ AQSMAATIKPGDDWKKTLK LPPKDLRIKTSDVTSTKGNE FEDYCLKRELLMGIFEMGW EKPSPIQEESIPIALSGRDILA RAKNGTGKSGAYLIPLLERL DLKKDNIQAMVIVPTRELAL QVSQICIQVSKHMGGAKVM ATTGGTNLRDDIMRLDDTV HVVIATPGRILDLIKKGVAK VDHVQMIVLDEADKLLSQD FVQIMEDIILTLPKNRQILLY SATFPLSVQKFMNSHLQKP YEINLMEELTLKGVTQYYA YVTERQKVHCLNTLFSRLQI NQSIIFCNSSQRVELLAKKIS QLGYSCFYIHAKMRQEHRN RVFHDFRNGLCRNLVCTDL FTRGIDIQAVNVVINFDFPKL AETYLHRIGRSGRFGHLGLA INLITYDDRFNLKSIEEQLGT EIKPIPSNIDKSLYVAEYHSE PAEDEKP (SEQ ID NO: 31) | ATGAGCACAGCTCGCACCGAGAACCCGGTGATTAT GGGCCTGTCCAGCCAGAACGGACAGCTCAGAGGGC CTGTAAAGGCTTCAGCAGGCCCCGGCGGAGGCGGC ACACAACCACAACCACAGCTTAATCAGCTTAAGAA TACTAGCACTATTAATAACGGAACACCGCAGCAGG CCCAAAGCATGGCTGCCACAATTAAACCCGGAGAT GACTGGAAGAAGACCCTGAAGCTCCCTCCAAAAGA TCTCAGGATTAAAACTAGCGATGTTACTTCAACAAA GGGAAATGAGTTCGAAGACTACTGTCTGAAGCGAG AGTTGCTGATGGGGATTTTCGAAATGGGCTGGGAG AAGCCCTCTCCTATTCAAGAAGAGAGCATCCCCATC GCTCTGTCCGGGAGGGACATCCTTGCCAGGGCTAAA AATGGGACCGGAAAATCAGGAGCTTACTTGATCCC ACTCCTTGAAAGGCTTGATCTCAAGAAGGACAACAT CCAAGCTATGGTTATCGTGCCAACTAGAGAACTCGC CCTCCAGGTCAGCCAGATTTGCATCCAGGTGAGTAA GCACATGGGCGGAGCTAAGGTGATGGCTACAACTG GAGGGACTAACCTGCGAGACGACATAATGAGACTT GATGACACAGTCCATGTGGTCATCGCTACACCTGGG AGGATTCTGGATCTGATCAAAAAAGGAGTGGCAAA GGTGGATCATGTGCAGATGATAGTCTTGGACGAGG CCGACAAACTGCTGAGCCAAGACTTTGTCAGATCA TGGAGGATATCATCTTGACACTCCCCAAGAACCGAC AGATTCTGCTGTACTCCGCAACATTTCCTCTTTCCGT TCAGAAATTCATGAACTCACATCTCCAGAAACCTTA TGAGATCAATTTGATGGAAGAACTGACACTGAAGG GCGTGACCCAGTATTATGCCTACGTTACTGAGAGGC AAAAGGTCCACTGCCTGAATACTCTCTTCTCCAGGC TCCAGATCAACCAGTCTATCATCTTTTGCAATAGCT CCCAGCGAGTCGAGCTGCTGGCTAAGAAGATCTCA CAGCTTGGATATTCCTGTTTCTACATCCATGCTAAG ATGAGACAAGCACAGAAACCGCGTCTTTCATGA TTTCCGGAACGGACTCTGTCGCAACCTGGTTTGCAC AGATCTTTTTACTAGAGGCATCGATATCCAAGCAGT GAACGTGGTTATCAACTTCGACTTTCCCAAACTCGC CGAGACTTATCTTCATAGAATTGGCCGATCCGGTAG |

TABLE 5-continued

Non-limiting, Exemplary Modifying Domains for Translation Repression

| Modifying domain | Amino acid sequence | Nucleotide sequence (cDNA) |
|---|---|---|
| | | GTTTGGGCACCTGGGGCTCGCCATCAATCTCATTAC GTATGATGATAGGTTCAACCTCAAGTCAATAGAAG AGCAGTTGGGGACCGAGATCAAACCAATCCCGAGC AATATTGACAAATCACTCTATGTGGCCGAATACCAT TCAGAGCCTGCCGAGGATGAGAAGCCT (SEQ ID NO: 32) |

In some embodiments, the RNA repressor is an endoribonuclease, which represses the expression of the output molecule by cleaving and degrading the mRNA encoding the output molecule. Any of the endoribonucleases described herein (e.g., the endoribonucleases listed in Table 1) may be used for this purpose. When endoribonucleases are used as RNA repressors, the recognition sites for the RNA repressor are the recognition and cleavage sites for the endoribonucleases (e.g., also listed in Table 1). The recognition sites for endoribonucleases sites may be upstream and/or downstream of the nucleotide sequence encoding the output molecule. In some embodiments, the recognition sites are the recognition sites for the endoribonuclease Cse3.

In some embodiments, the RNA repressor is a trans-acting ribozyme. A "trans-acting ribozyme," as used herein, refers to a ribozyme that cleaves an external substrate in a specific-manner. In these instances, the cleavage site for the RNA cleaver in the RNA transcript of the present disclosure comprises the recognition and cleavage sites for the trans-acting ribozyme. Non-limiting, exemplary trans-acting ribozymes are provided in Table 6.

As described herein, the first sensor circuit and the second sensor circuit are initially connected by a splitter in the RNA transcript. A "splitter," as used herein, refers to a ribonucleotide sequence containing multiple elements for separating (e.g., by endoribonuclease cleavage) the first and the second circuits and for the stabilization of the RNA fragments after the separating. The splitter comprises, from 5' to 3', a first RNA stabilizer, a cleavage site, a second RNA stabilizer, and an internal ribosome entry site.

To separate the first sensor circuit and the second sensor circuit, the RNA transcript containing both is cleaved at the cleavage site in the splitter, generating two RNA fragments, the 5' fragment comprises the first sensor circuit and the 3' fragment containing the second sensor circuit. In some embodiments, the cleavage is carried out by an endoribonuclease. In some embodiments, the cleavage site in the splitter comprises the recognition and cleavage site of an endoribonuclease (e.g., any endoribonuclease described herein, such as those listed in Table 1). In some embodiments, the endoribonuclease is Csy4 and the cleavage site in the splitter comprises one or more (e.g., 1, 2, 3, or more) recognition and cleavage sites of Csy4.

In some embodiments, the cleavage is carried out by a ribozyme (e.g., acting ribozyme). A "ribozyme" is a RNA molecule that is capable of catalyzing specific biochemical reactions, similar to the action of protein enzymes. In some embodiments, the ribozyme used in the splitters of the present disclosure is a cis-acting ribozyme. A "cis-acting ribozyme" refers to a ribozyme that catalyzes self-cleavage (intramolecular or "in-cis" catalysis) from the RNA molecule that contains the ribozyme itself. In these instances, the cleavage site in the splitter of the present disclosure comprises a cis-acting ribozyme, which upon cleavage, excises itself and leaving two separated fragments of the initial RNA transcript. In some embodiments, the ribozyme used in the splitters of the present disclosure is a trans-acting ribozyme. Suitable acting ribozymes that may be used in accordance with the present disclosure and their respective sequences include, without limitation: hammerhead ribozymes, Hepatitis delta virus ribozymes, hairpin ribozymes, twister ribozymes, twister sister ribozymes, pistol ribozymes, hatchet ribozymes, glmS ribozymes, varkud satellite ribozymes, and spliceozyme ribozymes. The nucleotide sequences of the ribozymes are provided in Table 6.

TABLE 6

Non-limiting, Exemplary Ribozymes and Sequences

| Ribozyme | Cis or trans | Nucleotide sequence |
|---|---|---|
| Hammerhead | Cis | CACCACGAACCTGATGAGTCCGTGAGGACGAAACGAGCTAGCTCGT CGTTCGTGCTG (SEQ ID NO: 33) |
| Schistosoma-like hammerhead ribozyme | Cis | GGCGTCGGAGTATCCAATCAGTGGATGTACTACTCCCTGATGAGTCC CAAATAGGACGAAACGCC (SEQ ID NO: 34) |
| Satellite virus hammerhead ribozyme | Cis | GGGTGCCCTGTCGGAGGATGTGCTTTCCTCCCTGATGAGTCCGTGAG GACGAAACAGGGCACCC (SEQ ID NO: 35) |
| Hepatitis delta virus ribozymes | Cis | GGCCGGCATGGTCCCAGCCTCCTCGCTGGCGCCGGCTGGGCAACATG CTTCGGCATGGCGAATGGGAC (SEQ ID NO: 36) |
| RNase P | trans | ATAGGGCGGAGGGAAGCTCATCAGTGGGGCCACGAGCTGAGTGCGT CCTGTCACTCCACTCCCATGTCCCTTGGGAAGGTCTGAGACTAGGGC CAGAGGCGGCCCTAACAGGGCTCTCCCTGAGCTTCGGGGAGGTGAG |

TABLE 6-continued

Non-limiting, Exemplary Ribozymes and Sequences

| Ribozyme | Cis or trans | Nucleotide sequence |
|---|---|---|
| | | TTCCCAGAGAACGGGGCTCCGCGCGAGGTCAGACTGGGCAGGAGAT<br>GCCGTGGACCCCGCCCTTCGGGGAGGGGCCCGGCGGATGCCTCCTTT<br>GCCGGAGCTTGGAACAGACTCACGGCCAGCGAAGTGAGTTCAATGG<br>CTGAGGTGAGGTACCCCGCAGGGGACCTCATAACCCAATTCAGACT<br>ACTCTCCTCCGCCCATT (SEQ ID NO: 37)<br>Exemplary RNase P recognition sequence:<br>GACGCTGGTGGCTGGCACTCCTGGTTTCCAGGACGGGGTTCAAGTCC<br>CTGCGGTGTCT (SEQ ID NO: 38) |

RNA fragments with free and unprotected 3' ends (in the 5' fragment) and 5' ends (in the 3' fragment) are generated upon cleavage, which are rapid degraded if unprotected. The splitter described herein comprises RNA stabilizers for the protection of the fragments generated from cleavage. A "RNA stabilizer," refers to a RNA sequence that, when present in a RNA molecule (e.g., at the 5' end or 3' end), protects the RNA molecule from degradation. In some embodiments, the RNA stabilizer sequence forms secondary structures that blocks access of exoribonucleases to the unprotected ends of the RNA molecule. The splitter described herein comprises a first RNA stabilizer, which, after cleavage, is at the 3' end of the 5' fragment (the fragment that contains the first sensor circuit), thus preventing degradation of the 5' fragment. Non-limiting examples of RNA stabilizers that may be used as the first RNA stabilizer of the present disclosure include: synthetic polyadenylated tails, and stabilizing RNA triple helix structures such as MALAT1 (e.g., as described in Brown et al., *Nature Structural & Molecular Biology* 21, 633-640, 2014, incorporated herein by reference), MENβenB triplex, HSHV PAN triplex, and histone stem loop. The splitter described herein further comprises a second RNA stabilizer, which, after cleavage, is at the 5' end of the 3' fragment (the fragment that contains the second sensor circuit), thus preventing degradation of the 3' fragment. In some embodiments, the second RNA stabilizer of the present disclosure is a 5' cloverleaf element. In some embodiments, the 5' cloverleaf element is derived from a virus, such as a poliovirus. Such 5' cloverleaf element are described in the art, e.g., in Murray et al., *RNA* 7: 1126-1141, 2001, incorporated herein by reference. The nucleotide sequences of non-limiting, exemplary RNA stabilizer sequences are provided in Table 7.

TABLE 7

Non-limiting, Exemplary RNA Stabilizers

| RNA stabilizer | 5' or 3' | Nucleotide sequence |
|---|---|---|
| MALAT1 | 3' | GAUUCGUCAGUAGGGUUGUAAAGGUUUUUCUUUUCCUGAGAAACAA<br>CCUUUUGUUUUCUCAGGUUUUGCUUUUUGGCCUUUCCCUAGCUUUAA<br>AAAAAAAAAGCAAAA (SEQ ID NO: 39) |
| MENβ triplex | 3' | GCCGCCGCAGGUGUUUCUUUUACUGAGUGCAGCCCAUGGCCGCACUC<br>AGGUUUUGCUUUUCACCUUCCCAUCUG (SEQ ID NO: 40) |
| KSHV PAN triplex | 3' | GCUGGGUUUUUCCUUGUUCGCACCGGACACCUCCAGUGACCAGACGG<br>CAAGGUUUUAUCCCAGU (SEQ ID NO: 41) |
| histone stem loop. | 3' | AAAAAGGCUCUUUUCAGAGCACCCA (SEQ ID NO: 42) |
| poliovirus cloverleaf element | 5' | UUAAAACAGCUCUGGGGUUGUACCCACCCCAGAGGCCCACGUGGCGG<br>CUAGUACUCCGGUAUUGCGGUACCCUUGUACGCCUGUUUUAUACUCC<br>CUUCCCGUAACUUAGACGCACAAA (SEQ ID NO: 43) |

The RNA stabilizers stabilize the RNA fragments containing the first or second sensor circuit, generated by cleavage at the cleavage site in the splitter in the cell state classifier RNA transcript. A RNA fragment is considered to be stabilized when the half-life of the RNA fragment is at least 20% longer with of the RNA stabilizer, compared to without the RNA stabilizer. For example, a RNA fragment is considered to be stabilized when the half-life of the RNA fragment is at least 20%, at least 30%, at least 40%, at least 50%, at least 60%, at least 70%, at least 90%, at least 100%, at least 2-fold, at least 5-fold, at least 10-fold, at least 50-fold, or at least 100-fold longer, compared to without the RNA stabilizer. In some embodiments, the half-life of the RNA fragment is 20%, 30%, 40%, 50%, 60%, 70%, 80%, 90%, 100%, 2-fold, 5-fold, 10-fold, 50-fold, 100-fold or more, longer with of the RNA stabilizer, compared to without the RNA stabilizer.

The splitter further comprises an internal ribosome entry site "IRES" at its 3' end. Upon cleavage of the initial RNA transcript, the IRES is present in the 3' fragment, upstream of the nucleotide sequence encoding the RNA repressor. An "internal ribosome entry site (IRES) is a RNA element that allows for translation initiation in a cap-independent manner, as part of the greater process of protein synthesis. In eukaryotic translation, initiation typically occurs at the 5' end of mRNA molecules, since 5' cap recognition is required for the assembly of the initiation complex. The presence of an IRES elements allows translation to initiate independent of a 5' cap. As such, the presence of the IRES in the 3' fragment of the initial RNA transcript allows expression of the RNA repressor. IRES s are commonly located in the 5'UTR of RNA viruses. Any of these IRES sequences may be used in accordance with the present disclosure. Information regarding the identify and sequences of IRES is available in the art, e.g., in public data bases such as iresite.org. In some embodiments, the IRES is derived from Encephalomyocarditis virus.

```
Encephalomyocarditis virus IRES Sequence
                                       (SEQ ID NO: 44)
CCCCTCTCCCTCCCCCCCCCCTAACGTTACTGGCCGAAGCCGCTTGGAAT

AAGGCCGGTGTGCGTTTGTCTATATGTTATTTTCCACCATATTGCCGTCT

TTTGGCAATGTGAGGGCCCGGAAACCTGGCCCTGTCTTCTTGACGAGCAT

TCCTAGGGGTCTTTCCCCTCTCGCCAAAGGAATGCAAGGTCTGTTGAATG

TCGTGAAGGAAGCAGTTCCTCTGGAAGCTTCTTGAAGACAAACAACGTCT

GTAGCGACCCTTTGCAGGCAGCGGAACCCCCCACCTGGCGACAGGTGCCT

CTGCGGCCAAAAGCCACGTGTATAAGATACACCTGCAAAGGCGGCACAAC

CCCAGTGCCACGTTGTGAGTTGGATAGTTGTGGAAAGAGTCAAATGGCTC

ACCTCAAGCGTATTCAACAAGGGGCTGAAGGATGCCCAGAAGGTACCCCA

TTGTATGGGATCTGATCTGGGGCCTCGGTGCACATGCTTTACATGTGTTT

AGTCGAGGTTAAAAAACGTCTAGGCCCCCCGAACCACGGGGACGTGGTTT

TCCTTTGAAAAACACGATGATAA
```

In some embodiments, the cell state classifier comprises more than one (e.g., 2, 3, 4, 5, 6, 7, 8, 9, 10, or more) second sensor circuits, each second sensor circuit comprises one or more (e.g., 2, 3, 4, 5, 6, 7, 8, 9, 10, or more) targets sites for a second microRNA (microRNA high). In some embodiments, the one or more second sensor circuits each comprises a nucleotide sequence encoding a same RNA repressor. In some embodiments, the one or more second sensor circuits each comprises a nucleotide sequence encoding a different RNA repressor. Any RNA repressor known in the art and/or described herein may be used. Further, between each second sensor circuit, a splitter as described herein is inserted such that each second sensor circuit is cleaved from the initial RNA transcript and can function independently.

An "RNA version" of the cell state classifier is also provided. As described herein, the cell state classifier may be transcribed into a single RNA transcript, the RNA transcript comprising: (i) a first sensor circuit comprising one or more recognition sites for a RNA repressor, operably linked to a nucleotide sequence encoding an output molecule, and one or more target sites for a first microRNA; and (ii) a second sensor circuit that is downstream of the first sensor circuit, comprising a subgenomic promoter operably linked to a nucleotide sequence encoding the RNA repressor and one or more target sites for a second microRNA, wherein the first sensor circuit and the second sensor circuit are separated by a splitter comprising, from 5' to 3', a first RNA stabilizer, a cleavage site, a second RNA stabilizer, and an internal ribosome entry site. In some embodiments, the RNA version of the cell state classifier is transcribed from the DNA encoding such, either in a cell or in vitro (e.g., in an in vitro transcription reaction). In some embodiments, the RNA version of the cell state classifier is chemically synthesized.

In some embodiments, the RNA version of the cell state classifier comprises more than one of the second sensor circuit. The RNA version of the cell state classifier is cleaved at the cleavage site in the splitters separating the circuits, generating circuits that function independently.

Further provided herein are the functionality of the cell state classifiers encoded on one RNA transcript (including the DNA version and the RNA version) and methods of using them. In some embodiments, the methods comprising delivering the cell state classifiers described herein into a cell (e.g., by any of the methods described herein and known to one skilled in the art). In some embodiments, the methods comprises maintaining the cell containing the cell state classifiers. In some embodiments, the maintaining is carried out under conditions to allow the cell state classifier to function. In some embodiments, the presence of the cell state classifier in the cell does not change the native microRNA profile of the cell.

Once introduced into a cell, the different circuits of the cell state classifier are generated by cleaving at the cleavage site in each splitter (e.g., by an endoribonuclease or a cis-acting ribozyme). If the cleavage is carried out by an endoribonuclease, the endoribonuclease may be provided separately, e.g., on a separate expression vector. Each circuit is able to function independently in a cell for the detection of the microRNA profile.

In some embodiments, no microRNA input is detected. For example, this may occur if none of the microRNAs the cell state classifier is designed to detect (either microRNA-high or microRNA-low) are expressed in the cell (e.g., expression level is not detectable). As such, the output molecule encoded by the first sensor circuit can express in the absence of microRNA-low inhibition. However, since there is no detectable microRNA-high, the RNA repressor is expressed, repressing the expression of the output molecule. It is to be understood that in this instance, repression dominates and no output molecule will be produced.

In some embodiments, the first microRNA expresses (e.g., has a detectable expression level by the cell state classifier) or has high expression level, and the output molecule encoded by the first sensor circuit (e.g., mKate in FIG. 3A) does not express because the first microRNA mediates the degradation of the mRNA encoding the output molecule (translational control).

In some embodiments, the second microRNA (microRNA-high) expresses (e.g., has a detectable expression level by the cell state classifier) or has high expression level, and thus the RNA repressor (e.g., L7Ae in FIG. 3A) does not express, because the second microRNA mediates the degradation of the mRNA encoding the RNA repressor (translational control). As a result, the translational repression of the output molecule is alleviated, leading to the expression of the output molecule, in the absence of the first microRNA-low. In an instance where both the first and second microRNAs (both microRNA-low and microRNA-high) express, the first microRNA mediates the degradation of the mRNA encoding the output molecule. Thus, even in the absence of the translational repression from the RNA repressor, the output molecule still does not express.

As such, the cell state classifier also has a logic function, where the cell state classifier produces an output molecule only when a matching microRNA profile is detected. In some embodiments, a matching microRNA profile comprises: (i) the first microRNAs (microRNA-low) does not express or the expression level is low (e.g., undetectable by the cell state classifier); and (ii) the expression level of the second microRNA (microRNA-high) is high (e.g., at least detectable by the cell state classifier), and the output molecule is produced by the cell state classifier. In some embodiments, the first microRNA (microRNA low) expresses (e.g., expression level is detectable by the cell state classifier) or has high expression level, and the second microRNA (microRNA-high) does not express (e.g., expression level is not detectable by the cell state classifier), and no output molecule or very low output molecule is produced by the cell state classifier. In some embodiments, the first microRNA does not express or the expression level is low (e.g., expression level is detectable by the cell state classifier), and the second microRNAs (microRNA-high) does not express or the expression level is low (e.g., expression level is not detectable by the cell state classifier), and no output molecule or very low output molecule is produced by the cell state classifier. In some embodiments, the first microRNAs (microRNA low) expresses (e.g., expression level is detectable by the cell state classifier) or has high expression level, and the second microRNA expresses or has high expression level, and no output molecule or very low output molecule is produced by the cell state classifier.

By placing the target sites for the first or second microRNA (microRNA-low or microRNA-high) in different circuits of the cell state classifier, additional functions of the cell state classifiers can be provided. For example, if the first sensor circuit comprises target sites for the second microRNA (miRNA-high) and the second sensor circuit comprising target sites for the first microRNA (miRNA-low), then the output of the cell state classifier circuit would be reversed such that output would be produced only in cells in which miRNA-low, but not miRNA-high, is expressed.

In some embodiments, to classify the cell, the method further comprises detecting an output molecule produced by the cell state classifier. For example, the output molecule may be fluorescent protein or an enzyme that acts on a substrate to produce a detectable molecule. One skilled in the art is familiar with methods of detecting different detectable molecules.

Genetic Elements

Further provided herein are the various genetic elements used in the genetic circuits of the cell state classifier. A "genetic element" refers to a particular nucleotide sequence that has a role in nucleic acid expression (e.g., promoter, enhancer, terminator) or encodes a discrete product of a genetic circuit (e.g., an activator, a repressor, a microRNA, or an output molecule).

The first and second sensor circuits of the cell state classifier "senses" microRNAs via microRNA target sites present in the sensor circuits. A "microRNA" or "miRNA" is a small non-coding RNA molecule that functions in RNA silencing and post-transcriptional regulation of gene expression (e.g., as described in Ambros et al., *Nature* 431 (7006): 350-5, 2004; and Bartel et al., *Cell.* 136 (2): 215-33, 2004). A microRNA may be 15-30 nucleotides in length. For example, a microRNA may be 15-30, 15-25, 15-20, 20-30, 20-25, or 25-30 nucleotides in length. In some embodiments, a microRNA may be 16-24 nucleotides in length. In some embodiments, a microRNA may be 20-24 nucleotides in length. In some embodiments, a microRNA may be 15, 16, 17, 18, 19, 20, 21, 22, 23, 24, 25, 26, 27, 28, 29, or 30 nucleotides in length.

A "microRNA target site" is a nucleotide sequence that is complementary to the nucleotide sequence of the microRNA. Naturally, microRNA targeting sites exist in messenger RNAs (mRNA), typically in the 3' untranslated regions of mRNAs. Binding of the microRNA to its target site in via sequence complementarity leads to silencing of an output molecule either via degrading the mRNA or suppressing translation of the mRNA (e.g., as described in Bartel et al., *Cell* 136 (2): 215-33 (2009), incorporated herein by reference) containing the microRNA binding sites. Herein, when microRNA target sites are referred to in the context of the genetic circuits (i.e., in a context of DNA), it intends to mean the nucleotide sequence that encodes the microRNA target sites in the mRNA that is produced from the genetic circuit. As described herein, designated microRNA target sites are placed either upstream or downstream, or both, of a coding sequence in genetic circuits. As such, when a mRNA of such coding sequence is produced from the genetic circuit, the microRNA target sites are present in the 5' UTR or 3 ' UTR, or both 5' and 3' UTRs in the mRNA.

One skilled in the art is familiar with the mechanism of gene silencing by microRNAs. For example, in the cell state classifiers of the present disclosure, if a microRNA is expressed and a sensor circuit (e.g., the first or second sensor circuit) comprise one or more (e.g., 1, 2, 3, 4, 5, 6, 7, 8, 9, 10, or more) targets sites of the microRNA (either upstream or downstream of the coding sequence, or both), the microRNA can bind to the target sites in the mRNA produced by the sensor circuit and mediate the degradation of the mRNA, thus reducing the expression of the protein encoded by the mRNA (translational control). In some embodiments, expression of the protein encoded by the mRNA is reduced by at least 2-fold, at least 5-fold, at least 10-fold, at least 20-fold, at least 30-fold, at least 40-fold, at least 50-fold, at least 60-fold, at least 70-fold, at least 80-fold, at least 90-fold, at least 99-fold, or more compared to when the microRNA is not present. In some embodiments, expression of the protein encoded by the mRNA is no more than 1%, no more than 5%, no more than 10%, no more than 20%, no more than 30%, no more than 40%, no more than 50%, no more than 60%, no more than 70%, no more than 80% of the output molecule when the microRNA is not present. In some embodiments, a higher/lower level of the microRNA results in a higher/lower decrease in the protein encoded by the mRNA containing the microRNA target sites.

Information about the sequences, origins, and functions of known microRNAs maybe found in publically available databases (e.g., mirbase.org/, all versions, as described in Kozomara et al., *Nucleic Acids Res* 2014 42:D68-D73; Kozomara et al., *Nucleic Acids Res* 2011 39:D152-D157; Griffiths-Jones et al., *Nucleic Acids Res* 2008 36:D154-D158; Griffiths-Jones et al., *Nucleic Acids Res* 2006 34:D140-D144; and Griffiths-Jones et al., *Nucleic Acids Res* 2004 32:D109-D111, including the most recently released version miRBase 21, which contains "high confidence" microRNAs). Non-limiting examples of microRNAs that are expressed in cells and are able to be detected by the cell state classifier are: FF4, FF5, let-7b, let-7c, let-7d, let-7e, let-7f, let-7g, let-7i, miR-100, miR-103, miR-106a, miR-107, miR-10a, miR-10b, miR-122, miR-125a, miR-125b, miR-126, miR-126*, miR-127-3p, miR-128a, miR-129, miR-133b, miR-135b, miR-137, miR-141, miR-143, miR-145, miR-146a, miR-146b, miR-148a, miR-149, miR-150, miR-155, miR-15a, miR-17-3p, miR-17-5p, miR-181a, miR-181b, miR-181c, miR-183, miR-184, miR-186, miR-187, miR-189, miR-18a, miR-190, miR-191, miR-192, miR-195, miR-197, miR-199a, miR-199a*, miR-19a, miR-19b, miR-200a, miR-200a*, miR-200b, miR-200c, miR-202, miR-203, miR-205, miR-20a, miR-21, miR-210, miR-216, miR-218, miR-22, miR-221, miR-222, miR-223, miR-224, miR-23a, miR-23b, miR-24, miR-25, miR-26a, miR-26b, miR-27a, miR- 27b, miR-29a, miR-29b, miR-296-5p, miR-301, miR-302a, miR-302a*, miR-30a, miR-30b, miR-30c, miR-30d, miR-30e-3p, miR-30e-5p, miR-31, miR-320, miR-323, miR-324-5p, miR-326, miR-330, miR-331, miR-335, miR-346, miR-34a, miR-370, miR-372, miR-373, miR-373*, miR-497, miR-498, miR-503, miR-92, miR-93, miR-96, and miR-99a.

In some embodiments, the microRNA detected using the cell state classifier of the present disclosure is selected from: hsa-let-7a-2-3p, hsa-let-7a-3p, hsa-let-7a-5p, hsa-let-7b-3p, hsa-let-7b-5p, hsa-let-7c-5p, hsa-let-7d-3p, hsa-let-7d-5p, hsa-let-7e-3p, hsa-let-7e-5p, hsa-let-7f-1-3p, hsa-let-7f-2-3p, hsa-let-7f-5p, hsa-let-7g-3p, hsa-let-7g-5p, hsa-let-7i-5p, hsa-miR-1, hsa-miR-1-3p, hsa-miR-1-5p, hsa-miR-100-3p, hsa-miR-100-5p, hsa-miR-101-3p, hsa-miR-101-5p, hsa-miR-103a-2-5p, hsa-miR-103a-3p, hsa-miR-105-3p, hsa-miR-105-5p, hsa-miR-106a-3p, hsa-miR-106a-5p, hsa-miR-106b-3p, hsa-miR-106b-5p, hsa-miR-107, hsa-miR-10a-3p, hsa-miR-10a-5p, hsa-miR-10b-3p, hsa-miR-10b-5p, hsa-miR-1185-1-3p, hsa-miR-1185-2-3p, hsa-miR-1185-5p, hsa-miR-122a-5p, hsa-miR-1249-3p, hsa-miR-1249-5p, hsa-miR-124a-3p, hsa-miR-125a-3p, hsa-miR-125a-5p, hsa-miR-125b-1-3p, hsa-miR-125b-2-3p, hsa-miR-125b-5p, hsa-miR-126-3p, hsa-miR-126-5p, hsa-miR-127-3p, hsa-miR-1271-3p, hsa-miR-1271-5p, hsa-miR-1278, hsa-miR-128-1-5p, hsa-miR-128-2-5p, hsa-miR-128-3p, hsa-miR-1285-3p, hsa-miR-1285-5p, hsa-miR-1287-3p, hsa-miR-1287-5p, hsa-miR-129-1-3p, hsa-miR-129-2-3p, hsa-miR-129-5p, hsa-miR-1296-3p, hsa-miR-1296-5p, hsa-miR-1304-3p, hsa-miR-1304-5p, hsa-miR-1306-3p, hsa-miR-1306-5p, hsa-miR-1307-3p, hsa-miR-1307-5p, hsa-miR-130a-3p, hsa-miR-130b-3p, hsa-miR-130b-5p, hsa-miR-132-3p, hsa-miR-132-5p, hsa-miR-133a-3p, hsa-miR-133a-5p, hsa-miR-133b, hsa-miR-134-3p, hsa-miR-134-5p, hsa-miR-135a-3p, hsa-miR-135a-5p, hsa-miR-135b-3p, hsa-miR-135b-5p, hsa-miR-136-3p, hsa-miR-136-5p, hsa-miR-138-1-3p, hsa-miR-138-5p, hsa-miR-139-3p, hsa-miR-139-5p, hsa-miR-140-3p, hsa-miR-140-5p, hsa-miR-141-3p, hsa-miR-141-5p, hsa-miR-142-3p, hsa-miR-142-5p, hsa-miR-143-3p, hsa-miR-143-5p, hsa-miR-144-3p, hsa-miR-144-5p, hsa-miR-145-5p, hsa-miR-146a-3p, hsa-miR-146a-5p, hsa-miR-147a, hsa-miR-148a-3p, hsa-miR-148a-5p, hsa-miR-148b-3p, hsa-miR-148b-5p, hsa-miR-149-3p, hsa-miR-144-3p, hsa-miR-150-3p, hsa-miR-150-5p, hsa-miR-151a-3p, hsa-miR-151a-5p, hsa-miR-152-3p, hsa-miR-152-5p, hsa-miR-154-3p, hsa-miR-154-5p, hsa-miR-155-3p, hsa-miR-155-5p, hsa-miR-15a-3p, hsa-miR-15a-5p, hsa-miR-15b-3p, hsa-miR-15b-5p, hsa-miR-16-1-3p, hsa-miR-16-2-3p, hsa-miR-16-5p, hsa-miR-17-3p, hsa-miR-17-5p, hsa-miR-181a-3p, hsa-miR-181a-5p, hsa-miR-181b-2-3p, hsa-miR-181b-5p, hsa-miR-181c-5p, hsa-miR-181d-3p, hsa-miR-181d-5p, hsa-miR-182-3p, hsa-miR-182-5p, hsa-miR-183-3p, hsa-miR-183-5p, hsa-miR-185-3p, hsa-miR-185-5p, hsa-miR-186-3p, hsa-miR-186-5p, hsa-miR-188-3p, hsa-miR-188-5p, hsa-miR-18a-3p, hsa-miR-18a-5p, hsa-miR-18b-5p, hsa-miR-1908-3p, hsa-miR-1908-5p, hsa-miR-190a-3p, hsa-miR-190a-5p, hsa-miR-191-3p, hsa-miR-191-5p, hsa-miR-1910-3p, hsa-miR-1910-5p, hsa-miR-192-3p, hsa-miR-192-5p, hsa-miR-193a-3p, hsa-miR-193a-5p, hsa-miR-193b-3p, hsa-miR-193b-5p, hsa-miR-194-3p, hsa-miR-194-5p, hsa-miR-195-3p, hsa-miR-195-5p, hsa-miR-196a-3p, hsa-miR-196a-5p, hsa-miR-196b-3p, hsa-miR-196b-5p, hsa-miR-197-3p, hsa-miR-197-5p, hsa-miR-199a-3p, hsa-miR-199a-5p, hsa-miR-199b-3p, hsa-miR-199b-5p, hsa-miR-19a-3p, hsa-miR-19a-5p, hsa-miR-19b-1-5p, hsa-miR-19b-2-3p, hsa-miR-19b-3p, hsa-miR-200a-3p, hsa-miR-200a-5p, hsa-miR-200b-3p, hsa-miR-200b-5p, hsa-miR-200c-3p, hsa-miR-200c-5p, hsa-miR-202-3p, hsa-miR-202-5p, hsa-miR-203a-3p, hsa-miR-203a-5p, hsa-miR-204-5p, hsa-miR-208b-3p, hsa-miR-208b-5p, hsa-miR-20a-3p, hsa-miR-20a-5p, hsa-miR-20b-3p, hsa-miR-20b-5p, hsa-miR-21-5p, hsa-miR-210-3p, hsa-miR-210-5p, hsa-miR-211-3p, hsa-miR-211-5p, hsa-miR-2116-3p, hsa-miR-2116-5p, hsa-miR-212-3p, hsa-miR-214-3p, hsa-miR-215-5p, hsa-miR-217, JG_miR-218-1-3p, hsa-miR-218-5p, hsa-miR-219a-1-3p, hsa-miR-219a-2-3p, hsa-miR-219a-5p, hsa-miR-219b-3p, hsa-miR-219b-5p, hsa-miR-22-3p, hsa-miR-22-5p, hsa-miR-221-3p, hsa-miR-221-5p, hsa-miR-222-3p, hsa-miR-222-5p, hsa-miR-223-3p, hsa-miR-223-5p, hsa-miR-23a-3p, hsa-miR-23a-5p, hsa-miR-23b-3p, hsa-miR-24-1-5p, hsa-miR-25-3p, hsa-miR-25-5p, hsa-miR-26a-1-3p, hsa-miR-26a-2-3p, hsa-miR-26a-5p, hsa-miR-26b-5p, hsa-miR-27a-3p, hsa-miR-27a-5p, hsa-miR-27b-3p, hsa-miR-27b-5p, hsa-miR-28-3p, hsa-miR-28-5p, hsa-miR-296-3p, hsa-miR-296-5p, hsa-miR-299-3p, hsa-miR-299-5p, hsa-miR-29a-3p, hsa-miR-29a-5p, hsa-miR-29b-1-5p, hsa-miR-29b-3p, hsa-miR-29c-3p, hsa-miR-301a-3p, hsa-miR-301a-5p, hsa-miR-301b-3p, hsa-miR-301b-5p, hsa-miR-302a-3p, hsa-miR-302a-5p, hsa-miR-302b-5p, hsa-miR-302c-3p, hsa-miR-302c-5p, hsa-miR-3065-3p, hsa-miR-3065-5p, hsa-miR-3074-3p, hsa-miR-3074-5p, hsa-miR-30a-3p, hsa-miR-30a-5p, hsa-miR-30b-3p, hsa-miR-30b-5p, hsa-miR-30c-1-3p, hsa-miR-30c-2-3p, hsa-miR-30c-5p, hsa-miR-30d-3p, hsa-miR-30d-5p, hsa-miR-30e-3p, hsa-miR-30e-5p, hsa-miR-31-3p, hsa-miR-31-5p, hsa-miR-3130-3p, hsa-miR-3130-5p, hsa-miR-3140-3p, hsa-miR-3140-5p, hsa-miR-3144-3p, hsa-miR-3144-5p, hsa-miR-3158-3p, hsa-miR-3158-5p, hsa-miR-32-3p, hsa-miR-32-5p, hsa-miR-320a, hsa-miR-323a-3p, hsa-miR-323a-5p, hsa-miR-324-3p, hsa-miR-324-5p, hsa-miR-326, hsa-miR-328-3p, hsa-miR-328-5p, hsa-miR-329-3p, hsa-miR-329-5p, hsa-miR-330-3p, hsa-miR-330-5p, hsa-miR-331-3p, hsa-miR-331-5p, hsa-miR-335-3p, hsa-miR-335-5p, hsa-miR-337-3p, hsa-miR-337-5p, hsa-miR-338-3p, hsa-miR-338-5p, hsa-miR-339-3p, hsa-miR-339-5p, hsa-miR-33a-3p, hsa-miR-33a-5p, hsa-miR-33b-3p, hsa-miR-33b-5p, hsa-miR-340-3p, hsa-miR-340-5p, hsa-miR-342-3p, hsa-miR-342-5p, hsa-miR-345-3p, hsa-miR-345-5p, hsa-miR-34a-3p, hsa-miR-34a-5p, hsa-miR-34b-3p, hsa-miR-34b-5p, hsa-miR-34c-3p, hsa-miR-34c-5p, hsa-miR-3605-3p, hsa-miR-3605-5p, hsa-miR-361-3p, hsa-miR-361-5p, hsa-miR-3613-3p, hsa-miR-3613-5p, hsa-miR-3614-3p, hsa-miR-3614-5p, hsa-miR-362-3p, hsa-miR-362-5p, hsa-miR-363-3p, hsa-miR-363-5p, hsa-miR-365a-3p, hsa-miR-365a-5p, hsa-miR-365b-3p, hsa-miR-365b-5p, hsa-miR-369-3p, hsa-miR-369-5p, hsa-miR-370-3p, hsa-miR-370-5p, hsa-miR-374a-3p, hsa-miR-374a-5p, hsa-miR-374b-3p, hsa-miR-374b-5p, hsa-miR-375, hsa-miR-376a-2-5p, hsa-miR-376a-3p, hsa-miR-376a-5p, hsa-miR-376c-3p, hsa-miR-376c-5p, hsa-miR-377-3p, hsa-miR-377-5p, hsa-miR-378a-3p, hsa-miR-378a-5p, hsa-miR-379-3p, hsa-miR-379-5p, hsa-miR-381-3p, hsa-miR-381-5p, hsa-miR-382-3p, hsa-miR-382-5p, hsa-miR-409-3p, hsa-miR-409-5p, hsa-miR-411-3p, hsa-miR-411-5p, hsa-miR-412-3p, hsa-miR-421, hsa-miR-423-3p, hsa-miR-423-5p, hsa-miR-424-3p, hsa-miR-424-5p, hsa-miR-425-3p, hsa-miR-425-5p, hsa-miR-431-3p, hsa-miR-431-5p, hsa-miR-432-5p, hsa-miR-433-3p, hsa-miR-433-5p, hsa-miR-449a, hsa-miR-449b-5p, hsa-miR-450a-1-3p, hsa-miR-450a-2-3p, hsa-miR-450a-5p, hsa-miR-450b-3p, hsa-miR-450b-5p, hsa-miR-451a, hsa-miR-452-3p, hsa-miR-4524a-3p, hsa-miR-4524a-5p, hsa-miR-4536-3p, hsa-miR-4536-5p, hsa-miR-454-3p, hsa-miR-454-5p, hsa-miR-4707-3p, hsa-miR-4707-5p, hsa-miR-4755-3p, hsa-miR-4755-5p, hsa-miR-4787-3p, hsa-miR-4787-5p, hsa-miR-483-3p, hsa-miR-483-5p, hsa-miR- 484, hsa-miR-485-3p, hsa-miR-485-5p, hsa-miR-487b-3p, hsa-miR-487b-5p, hsa-miR-488-3p, hsa-miR-488-5p, hsa-miR-489-3p, hsa-miR-490-3p, hsa-miR-490-5p, hsa-miR-491-3p, hsa-miR-491-5p, hsa-miR-493-3p, hsa-miR-493-5p, hsa-miR-494-3p, hsa-miR-494-5p, hsa-miR-495-3p, hsa-miR-495-5p, hsa-miR-497-3p, hsa-miR-497-5p, hsa-miR-498, hsa-miR-5001-3p, hsa-miR-5001-5p, hsa-miR-500a-3p, hsa-miR-500a-5p, hsa-miR-5010-3p, hsa-miR-5010-5p, hsa-miR-503-3p, hsa-miR-503-5p, hsa-miR-504-3p, hsa-miR-504-5p, hsa-miR-505-3p, hsa-miR-505-5p, hsa-miR-506-3p, hsa-miR-506-5p, hsa-miR-508-3p, hsa-miR-508-5p, hsa-miR-509-3-5p, hsa-miR-509-3p, hsa-miR-509-5p, hsa-miR-510-3p, hsa-miR-510-5p, hsa-miR-512-5p, hsa-miR-513c-3p, hsa-miR-513c-5p, hsa-miR-514a-3p, hsa-miR-514a-5p, hsa-miR-514b-3p, hsa-miR-514b-5p, hsa-miR-516b-5p, hsa-miR-518c-3p, hsa-miR-518f-3p, hsa-miR-5196-3p, hsa-miR-5196-5p, hsa-miR-519a-3p, hsa-miR-519a-5p, hsa-miR-519c-3p, hsa-miR-519e-3p, hsa-miR-520c-3p, hsa-miR-520f-3p, hsa-miR-520g-3p, hsa-miR-520h, hsa-miR-522-3p, hsa-miR-525-5p, hsa-miR-526b-5p, hsa-miR-532-3p, hsa-miR-532-5p, hsa-miR-539-3p, hsa-miR-539-5p, hsa-miR-542-3p, hsa-miR-542-5p, hsa-miR-543, hsa-miR-545-3p, hsa-miR-545-5p, hsa-miR-548a-3p, hsa-miR-548a-5p, hsa-miR-548ar-3p, hsa-miR-548ar-5p, hsa-miR-548b-3p, hsa-miR-548d-3p, hsa-miR-548d-5p, hsa-miR-548e-3p, hsa-miR-548e-5p, hsa-miR-548h-3p, hsa-miR-548h-5p, hsa-miR-548j-3p, hsa-miR-548j-5p, hsa-miR-548o-3p, hsa-miR-548o-5p, hsa-miR-548v, hsa-miR-551b-3p, hsa-miR-551b-5p, hsa-miR-552-3p, hsa-miR-556-3p, hsa-miR-556-5p, hsa-miR-561-3p, hsa-miR-561-5p, hsa-miR-562, hsa-miR-567, hsa-miR-569, hsa-miR-570-3p, hsa-miR-570-5p, hsa-miR-571, hsa-miR-574-3p, hsa-miR-574-5p, hsa-miR-576-3p, hsa-miR-576-5p, hsa-miR-577, hsa-miR-579-3p, hsa-miR-579-5p, hsa-miR-582-3p, hsa-miR-582-5p, hsa-miR-584-3p, hsa-miR-584-5p, hsa-miR-589-3p, hsa-miR-589-5p, hsa-miR-590-3p, hsa-miR-590-5p, hsa-miR-595, hsa-miR-606, hsa-miR-607, hsa-miR-610, hsa-miR-615-3p, hsa-miR-615-5p, hsa-miR-616-3p, hsa-miR-616-5p, hsa-miR-617, hsa-miR-619-5p, hsa-miR-624-3p, hsa-miR-624-5p, hsa-miR-625-3p, hsa-miR-625-5p, hsa-miR-627-3p, hsa-miR-627-5p, hsa-miR-628-3p, hsa-miR-628-5p, hsa-miR-629-3p, hsa-miR-629-5p, hsa-miR-630, hsa-miR-633, hsa-miR-634, hsa-miR-635, hsa-miR-636, hsa-miR-640, hsa-miR-642a-3p, hsa-miR-642a-5p, hsa-miR-643, hsa-miR-645, hsa-miR-648, hsa-miR-6503-3p, hsa-miR-6503-5p, hsa-miR-651-3p, hsa-miR-651-5p, hsa-miR-6511a-3p, hsa-miR-6511a-5p, hsa-miR-652-3p, hsa-miR-652-5p, hsa-miR-653-5p, hsa-miR-654-3p, hsa-miR-654-5p, hsa-miR-657, hsa-miR-659-3p, hsa-miR-660-3p, hsa-miR-660-5p, hsa-miR-664b-3p, hsa-miR-664b-5p, hsa-miR-671-3p, hsa-miR-671-5p, hsa-miR-675-3p, hsa-miR-675-5p, hsa-miR-7-1-3p, hsa-miR-7-5p, hsa-miR-708-3p, hsa-miR-708-5p, hsa-miR-744-3p, hsa-miR-744-5p, hsa-miR-758-3p, hsa-miR-758-5p, hsa-miR-765, hsa-miR-766-3p, hsa-miR-766-5p, hsa-miR-767-3p, hsa-miR-767-5p, hsa-miR-769-3p, hsa-miR-769-5p, hsa-miR-802, hsa-miR-873-3p, hsa-miR-873-5p, hsa-miR-874-3p, hsa-miR-874-5p, hsa-miR-876-3p, hsa-miR-876-5p, hsa-miR-885-3p, hsa-miR-885-5p, hsa-miR-887-3p, hsa-miR-887-5p, hsa-miR-9-3p, hsa-miR-9-5p, hsa-miR-92a-1-5p, hsa-miR-92a-2-5p, hsa-miR-92a-3p, hsa-miR-92b-3p, hsa-miR-92b-5p, hsa-miR-93-3p, hsa-miR-93-5p, hsa-miR-941, hsa-miR-942-3p, hsa-miR-942-5p, hsa-miR-96-3p, hsa-miR-96-5p, hsa-miR-98-3p, hsa-miR-98-5p, hsa-miR-99a-3p, hsa-miR-99a-5p, hsa-miR-99b-3p, and hsa-miR-99b-5p.

In some embodiments, the cell state classifier of the present disclosure may be used in a bacterial cell. Though naturally-occurring bacterial cells lack true miRNAs (e.g., as described in Tjaden et al., *Nucleic Acids Res.* 34 (9): 2791-802), short non-coding RNA sequences have been identified in bacterial genome that broadly have comparable function as eukaryotic miRNAs. Such bacterial short non-coding RNAs function similarly as the miRNAs of the present disclosure and may be detected by the cell state classifier described herein.

For classifying a cell type (e.g., a cancer cell), one skilled in the art is familiar with the microRNAs that express specifically in such cell type but not in other cell types, and their respective nucleotide sequences. One skilled in the art is also familiar with the designing the target sites for the microRNA to be detected. Non-limiting, exemplary microRNA and respective target site sequences are provided in Table 8.

TABLE 8

Non-limiting, Exemplary Synthetic microRNA and Target Sites

| microRNA Name | Nucleotide Sequence Encoding microRNA | Target Sequence |
| --- | --- | --- |
| FF3 | TTTGTATTCAGCCCATATCG (SEQ ID NO: 45) | AACGATATGGGCTGAATACAAA (SEQ ID NO: 46) |
| FF4 | TTTAATTAAAGACTTCAAGCG (SEQ ID NO: 47) | CCGCTTGAAGTCTTTAATTAAA (SEQ ID NO: 48) |
| FF5 | TAATTGTCAAATCAGAGTGC (SEQ ID NO: 49) | AAGCACTCTGATTTGACAATTA (SEQ ID NO: 50) |
| FF6 | TTTATGAGGAATCTCTTTGG (SEQ ID NO: 51) | AACCAAAGAGATTCCTCATAAA (SEQ ID NO: 52) |
| T1 | TTCGAAGTATTCCGCGTACG (SEQ ID NO: 53) | CACGTACGCGGAATACTTCGAA (SEQ ID NO: 54) |

One or more (e.g., 1, 2, 3, 4, 5, 6, 7, 8, 9, 10, or more) target sites of the microRNAs to be detected by the cell state classifier are placed in each circuit (e.g., first or second sensor circuit, first or second signal circuit, etc.) in a non-coding region, e.g., upstream and/or downstream of the nucleotide sequence encoding the protein that is produced by the circuit (e.g., activator, repressor, or output molecule). Being "upstream" means the microRNA target sites are placed 5' of the nucleotide sequence encoding the protein that is produced by the circuit (e.g., activator, repressor, or output molecule). Being "downstream" means the microRNA target sites are placed 3' of the nucleotide sequence encoding the protein that is produced by the circuit (e.g., activator, repressor, or output molecule).

In some embodiments, one or more (e.g., 1, 2, 3, 4, 5, 6, 7, 8, 9, 10, or more) microRNA target sites are placed upstream of and is immediately adjacent to (no nucleotides in between) the nucleotide sequence encoding the protein that is produced by the circuit (e.g., activator, repressor, or output molecule). In some embodiments, one or more (e.g., 1, 2, 3, 4, 5, 6, 7, 8, 9, 10, or more) microRNA target sites are placed upstream of and is separated by a nucleotide spacer from the nucleotide sequence encoding the protein that is produced by the circuit (e.g., activator, repressor, or output molecule). In some embodiments, the nucleotide spacer may be 1-20 nucleotides long. For example, the nucleotide spacer may be 1, 2, 3, 4, 5, 6, 7, 8, 9, 10, 11, 12, 13, 14, 15, 16, 17, 18, 19, or 20 nucleotides long. Nucleotide spacers longer than 20 nucleotide may also be used.

In some embodiments, one or more (e.g., 1, 2, 3, 4, 5, 6, 7, 8, 9, 10, or more) microRNA target sites are placed downstream of and is immediately adjacent to (no nucleotides in between) the nucleotide sequence encoding the protein that is produced by the circuit (e.g., activator, repressor, or output molecule). In some embodiments, one or more (e.g., 1, 2, 3, 4, 5, 6, 7, 8, 9, 10, or more) microRNA target sites are placed downstream of and is separated by a nucleotide spacer from the nucleotide sequence encoding the protein that is produced by the circuit (e.g., activator, repressor, or output molecule). In some embodiments, the nucleotide spacer may be 1-20 nucleotides long. For example, the nucleotide spacer may be 1, 2, 3, 4, 5, 6, 7, 8, 9, 10, 11, 12, 13, 14, 15, 16, 17, 18, 19, or 20 nucleotides long. Nucleotide spacers longer than 20 nucleotide may also be used.

In some embodiments, one or more (e.g., 1, 2, 3, 4, 5, 6, 7, 8, 9, 10, or more) microRNA target sites are placed upstream and downstream of and is immediately adjacent (no nucleotides in between) to the nucleotide sequence encoding the protein that is produced by the circuit (e.g., activator, repressor, or output molecule). In some embodiments, one or more (e.g., 1, 2, 3, 4, 5, 6, 7, 8, 9, 10, or more) microRNA target sites are placed upstream and downstream of and is separated by a nucleotide spacer from the nucleotide sequence encoding the protein that is produced by the circuit (e.g., activator, repressor, or output molecule). In some embodiments, the nucleotide spacer may be 1-20 nucleotides long. For example, the nucleotide spacer may be 1, 2, 3, 4, 5, 6, 7, 8, 9, 10, 11, 12, 13, 14, 15, 16, 17, 18, 19, or 20 nucleotides long. Nucleotide spacers longer than 20 nucleotide may also be used. In some embodiments, placing multiple microRNA target sites at different locations of each circuit strengthens (e.g., by at least 30%) the inhibitory effect of the microRNA on the product of the circuit. When multiple microRNA target sites are used, there may be a nucleotide spacer (e.g., a nucleotide spacer of 1, 2, 3, 4, 5, 6, 7, 8, 9, or 10 nucleotides long), or no space between each target site.

An "activator," as used herein, refers to a transcriptional activator. The terms "activator" or "transcriptional activator" are used interchangeably herein. A transcriptional activator is a protein that increases gene transcription of a gene or set of genes. Most activators function by binding sequence-specifically to a DNA site located in or near a promoter and making protein-protein interactions with the general transcription machinery (RNA polymerase and general transcription factors), thereby facilitating the binding of the general transcription machinery to the promoter.

Herein, the expression of a gene is considered to be "activated" by an activator if the expression of the genes is at least 20% higher in the presence of the activator, compared to without the activator. For example, the expression of a gene is considered to be activated by an activator if the expression of the genes is at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold, or higher in the presence of the activator, compared to without the activator. In some embodiments, the expression of a gene is considered to be activated by an activator if the expression of the genes is 20%, 30%, 40%, 50%, 60%, 70%, 80%, 90%, 100%, 2-fold, 5-fold, 10-fold, 100-fold, 1000-fold, or higher in the presence of the activator, compared to without the activator.

Conversely, the expression of a gene is considered to be "repressed" by a repressor (e.g., the RNA repressor described herein) if the expression of the gene is at least 20% lower in the presence of the repressor, compared to without the repressor. For example, the expression of a gene is considered to be repressed by a repressor if the expression of the genes is at least 20%, at least 30%, at least 40%, at least 50%, at least 60%, at least 70%, at least 80%, at least 90%, at least 95%, at least 99% or lower in the presence of the repressor, compared to without the repressor. In some embodiments, the expression of a gene is considered to be repressed by a repressor if the expression of the genes is 20%, 30%, 40%, 50%, 60%, 70%, 80%, 90%, 95%, 99%, or even 100% in the presence of the repressor, compared to without the repressor.

One skilled in the art is able to choose the transcriptional activators or RNA repressors for use in accordance with the present disclosure. Public databases are available for known or predicted transcriptional regulators, e.g., transcriptionfactor.org.

An "output molecule," as used herein, refers to a signal produced by the cell state classifier after detecting the microRNA profile (e.g., a matching microRNA profile). The cell state classifier of the present disclosure is designed such that the output molecule is expressed when a matching microRNA profile is detected. In some embodiments, the output molecule has a basal expression level and the expression level increases (e.g., by at least 20%) when a matching microRNA profile is detected, compared to when a non-matching microRNA profile is detected. For example, the expression level of the output molecule may be at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold, or higher when a matching microRNA profile is detected, compared to when a non-matching microRNA profile is detected. In some embodiments, the expression level of the output molecule is 20%, 30%, 40%, 50%, 60%, 70%, 80%, 90%, 100%, 2-fold, 5-fold, 10-fold, 100-fold, 1000-fold, or higher when a matching microRNA profile is detected, compared to when a non-matching microRNA profile is detected.

The output molecule, in some embodiments, is a detectable protein. In some embodiments, a detectable protein is a fluorescent protein. A fluorescent protein is a protein that emits a fluorescent light when exposed to a light source at an appropriate wavelength (e.g., light in the blue or ultraviolet range). Suitable fluorescent proteins that may be used in accordance with the present disclosure include, without limitation, eGFP, eYFP, eCFP, mKate2, mCherry, mPlum, mGrape2, mRaspberry, mGrape1, mStrawberry, mTangerine, mBanana, and mHoneydew. In some embodiments, a detectable protein is an enzyme that hydrolyzes an substrate to produce a detectable signal (e.g., a chemiluminescent signal). Such enzymes include, without limitation, beta-galactosidase (encoded by LacZ), horseradish peroxidase, or luciferase. In some embodiments, the output molecule is a fluorescent RNA. A fluorescent RNA is an RNA aptamer that emits a fluorescent light when bound to a fluorophore and exposed to a light source at an appropriate wavelength (e.g., light in the blue or ultraviolet range). Suitable fluorescent RNAs that may be used as an output molecule in the sensor circuit of the present disclosure include, without limitation, Spinach and Broccoli (e.g., as described in Paige et al., Science Vol. 333, Issue 6042, pp. 642-646, 2011, incorporated herein by reference). In some embodiments, the output molecule is a detectable protein fused to a degradation domain (e.g., the PEST sequence, DDd sequence or DDe sequence described herein), so as to reduce its half-life in cells, allowing for more accurate measuring of changes in the output signal.

In some embodiments, the output molecule is a therapeutic molecule. A "therapeutic molecule" is a molecule that has therapeutic effects on a disease or condition, and may be used to treat a diseases or condition. Therapeutic molecules of the present disclosure may be nucleic acid-based or protein or polypeptide-based.

In some embodiments, nucleic acid-based therapeutic molecule may be an RNA interference (RNAi) molecule (e.g., a microRNA, siRNA, or shRNA) or an nucleic acid enzyme (e.g., a ribozyme). RNAi molecules and there use in silencing gene expression are familiar to those skilled in the art. In some embodiments, the RNAi molecule targets an oncogene. An oncogene is a gene that in certain circumstances can transform a cell into a tumor cell. An oncogene may be a gene encoding a growth factor or mitogen (e.g., c-Sis), a receptor tyrosine kinase (e.g., EGFR, PDGFR, VEGFR, or HER2/neu), a cytoplasmic tyrosine kinase (e.g., Src family kinases, Syk-ZAP-70 family kinases, or BTK family kinases), a cytoplasmic serine/threonine kinase or their regulatory subunits (e.g., Raf kinase or cyclin-dependent kinase), a regulatory GTPase (e.g., Ras), or a transcription factor (e.g., Myc). In some embodiments, the oligonucleotide targets Lipocalin (Lcn2) (e.g., a Lcn2 siRNA). One skilled in the art is familiar with genes that may be targeted for the treatment of cancer.

Non-limiting examples of protein or polypeptide-based therapeutic molecules include enzymes, regulatory proteins (e.g., immuno-regulatory proteins), antigens, antibodies or antibody fragments, and structural proteins. In some embodiments, the protein or polypeptide-based therapeutic molecules are for cancer therapy.

Suitable enzymes (for operably linking to a synthetic promoter) for some embodiments of this disclosure include, for example, oxidoreductases, transferases, polymerases, hydrolases, lyases, synthases, isomerases, and ligases, digestive enzymes (e.g., proteases, lipases, carbohydrases, and nucleases). In some embodiments, the enzyme is selected from the group consisting of lactase, beta-galactosidase, a pancreatic enzyme, an oil-degrading enzyme, mucinase, cellulase, isomaltase, alginase, digestive lipases (e.g., lingual lipase, pancreatic lipase, phospholipase), amylases, cellulases, lysozyme, proteases (e.g., pepsin, trypsin, chymotrypsin, carboxypeptidase, elastase), esterases (e.g. sterol esterase), disaccharidases (e.g., sucrase, lactase, beta-galactosidase, maltase, isomaltase), DNases, and RNases.

Non-limiting examples of antibodies and fragments thereof include: bevacizumab (AVASTIN®), trastuzumab (HERCEPTIN®), alemtuzumab (CAMPATH®, indicated for B cell chronic lymphocytic leukemia), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-05, IOR-T6 (anti-CD1), IOR EGF/R3, celogovab (ONCOSCINT® OV103), epratuzumab (LYMPHOCIDE®), pemtumomab (THERAGYN®), Gliomab-H (indicated for brain cancer, melanoma). In some embodiments, the antibody is an antibody that inhibits an immune check point protein, e.g., an anti-PD-1 antibody such as pembrolizumab (Keytruda®) or nivolumab (Opdivo®), or an anti-CTLA-4 antibody such as ipilimumab (Yervoy®). Other antibodies and antibody fragments may be operably linked to a synthetic promoter, as provided herein.

A regulatory protein may be, in some embodiments, a transcription factor or a immunoregulatory protein. Non-limiting, exemplary transcriptional factors include: those of the NFkB family, such as Rel-A, c-Rel, Rel-B, p50 and p52; those of the AP-1 family, such as Fos, FosB, Fra-1, Fra-2, Jun, JunB and JunD; ATF; CREB; STAT-1, -2, -3, -4, -5 and -6; NFAT-1, -2 and -4; MAF; Thyroid Factor; IRF; Oct-1 and -2; NF-Y; Egr-1; and USF-43, EGR1, Sp1, and E2F1. Other transcription factors may be operably linked to a synthetic promoter, as provided herein.

As used herein, an immunoregulatory protein is a protein that regulates an immune response. Non-limiting examples of immunoregulatory include: antigens, adjuvants (e.g., flagellin, muramyl dipeptide), cytokines including interleukins (e.g., IL-2, IL-7, IL-15 or superagonist/mutant forms of these cytokines), IL-12, IFN-gamma, IFN-alpha, GM-CSF, FLT3-ligand), and immunostimulatory antibodies (e.g., anti-CTLA-4, anti-CD28, anti-CD3, or single chain/antibody fragments of these molecules). Other immunoregulatory proteins may be operably linked to a synthetic promoter, as provided herein.

As used herein, an antigen is a molecule or part of a molecule that is bound by the antigen-binding site of an antibody. In some embodiments, an antigen is a molecule or moiety that, when administered to or expression in the cells of a subject, activates or increases the production of antibodies that specifically bind the antigen. Antigens of pathogens are well known to those of skill in the art and include, but are not limited to parts (coats, capsules, cell walls, flagella, fimbriae, and toxins) of bacteria, viruses, and other microorganisms. Examples of antigens that may be used in accordance with the disclosure include, without limitation, cancer antigens, self-antigens, microbial antigens, allergens and environmental antigens. Other antigens may be operably linked to a synthetic promoter, as provided herein.

In some embodiments, the antigen of the present disclosure is a cancer antigen. A cancer antigen is an antigen that is expressed preferentially by cancer cells (i.e., it is expressed at higher levels in cancer cells than on non-cancer cells) and, in some instances, it is expressed solely by cancer cells. Cancer antigens may be expressed within a cancer cell or on the surface of the cancer cell. Cancer antigens that may be used in accordance with the disclosure include, without limitation, MART-1/Melan-A, gp100, adenosine deaminase-binding protein (ADAbp), FAP, cyclophilin b, colorectal associated antigen (CRC)-0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4 and MAGE-05. The cancer antigen may be selected from the group consisting of GAGE-1, GAGE-2, GAGE-3, GAGE-4, GAGE-5, GAGE-6, GAGE-7, GAGE-8 and GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pme1117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, PIA, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, CD20 and c-erbB-2. Other cancer antigens may be operably linked to a synthetic promoter, as provided herein.

In some embodiments, a protein or polypeptide-based therapeutic molecule is a fusion protein. A fusion protein is a protein comprising two heterologous proteins, protein domains, or protein fragments, that are covalently bound to each other, either directly or indirectly (e.g., via a linker), via a peptide bond. In some embodiments, a fusion protein is encoded by a nucleic acid comprising the coding region of a protein in frame with a coding region of an additional protein, without intervening stop codon, thus resulting in the translation of a single protein in which the proteins are fused together.

A "promoter" refers to a control region of a nucleic acid sequence at which initiation and rate of transcription of the remainder of a nucleic acid sequence are controlled. A promoter drives expression or drives transcription of the nucleic acid sequence that it regulates. A promoter may also contain sub-regions at which regulatory proteins and molecules may bind, such as RNA polymerase and other transcription factors. Promoters may be constitutive, inducible, activatable, repressible, tissue-specific or any combination thereof. A promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter can be referred to as "endogenous."

In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. Nos. 4,683,202 and 5,928,906).

In some embodiments, a promoter is an "inducible promoter," which refer to a promoter that is characterized by regulating (e.g., initiating or activating) transcriptional activity when in the presence of, influenced by or contacted by an inducer signal. An inducer signal may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter.

The administration or removal of an inducer signal results in a switch between activation and inactivation of the transcription of the operably linked nucleic acid sequence. Thus, the active state of a promoter operably linked to a nucleic acid sequence refers to the state when the promoter is actively regulating transcription of the nucleic acid sequence (i.e., the linked nucleic acid sequence is expressed). Conversely, the inactive state of a promoter operably linked to a nucleic acid sequence refers to the state when the promoter is not actively regulating transcription of the nucleic acid sequence (i.e., the linked nucleic acid sequence is not expressed).

An inducible promoter of the present disclosure may be induced by (or repressed by) one or more physiological condition(s), such as changes in light, pH, temperature, radiation, osmotic pressure, saline gradients, cell surface binding, and the concentration of one or more extrinsic or intrinsic inducing agent(s). An extrinsic inducer signal or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters of the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, an inducer signal of the present disclosure is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters.

In some embodiments, an inducer signal of the present disclosure is anhydrotetracycline (aTc), which is a derivative of tetracycline that exhibits no antibiotic activity and is designed for use with tetracycline-controlled gene expression systems, for example, in bacteria.

In some embodiments, an inducer signal of the present disclosure is isopropyl β-D-1-thiogalactopyranoside (IPTG), which is a molecular mimic of allolactose, a lactose metabolite that triggers transcription of the lac operon, and it is therefore used to induce protein expression where the gene is under the control of the lac operator. IPTG binds to the lac repressor and releases the tetrameric repressor from the lac operator in an allosteric manner, thereby allowing the transcription of genes in the lac operon, such as the gene coding for beta-galactosidase, a hydrolase enzyme that catalyzes the hydrolysis of β-galactosides into monosaccharides. The sulfur (S) atom creates a chemical bond which is non-hydrolyzable by the cell, preventing the cell from metabolizing or degrading the inducer. IPTG is an effective inducer of protein expression, for example, in the concentration range of 100 μM to 1.0 mM. Concentration used depends on the strength of induction required, as well as the genotype of cells or plasmid used. If lacIq, a mutant that over-produces the lac repressor, is present, then a higher concentration of IPTG may be necessary. In blue-white screen, IPTG is used together with X-gal. Blue-white screen allows colonies that have been transformed with the recombinant plasmid rather than a non-recombinant one to be identified in cloning experiments.

Other inducible promoter systems are known in the art and may be used in accordance with the present disclosure.

In some embodiments, inducible promoters of the present disclosure are from prokaryotic cells (e.g., bacterial cells). Examples of inducible promoters for use prokaryotic cells include, without limitation, bacteriophage promoters (e.g. Pls1con, T3, T7, SP6, PL) and bacterial promoters (e.g., Pbad, PmgrB, Ptrc2, Plac/ara, Ptac, Pm), or hybrids thereof (e.g. PLlacO, PLtetO). Examples of bacterial promoters for use in accordance with the present disclosure include, without limitation, positively regulated *E. coli* promoters such as positively regulated σ70 promoters (e.g., inducible pBad/araC promoter, Lux cassette right promoter, modified lambda Prm promoter, plac Or2-62 (positive), pBad/AraC with extra REN sites, pBad, P(Las) TetO, P(Las) CIO, P(Rhl), Pu, FecA, pRE, cadC, hns, pLas, pLux), GS promoters (e.g., Pdps), σ32 promoters (e.g., heat shock) and σ54 promoters (e.g., glnAp2); negatively regulated *E. coli* promoters such as negatively regulated σ70 promoters (e.g., Promoter (PRM+), TetR-TetR-4C P(Las) TetO, P(Las) CIO, P(Lac) IQ, RecA_DlexO_DLacO1, dapAp, FecA, Pspac-hy, pcI, plux-cI, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, LacI, LacIQ, pLacIQ1, pLas/cI, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, RcnR), σS promoters (e.g., Lutz-Bujard LacO with alternative sigma factor σ38), σ32 promoters (e.g., Lutz-Bujard LacO with alternative sigma factor σ32), and σ54 promoters (e.g., glnAp2); negatively regulated *B. subtilis* promoters such as repressible *B. subtilis* GA promoters (e.g., Gram-positive IPTG-inducible, Xyl, hyper-spank) and GB promoters. Other inducible microbial promoters may be used in accordance with the present disclosure.

The different genetic circuits of the cell state classifier may be included in one or more (e.g., 2, 3, 4, 5, 6, 7, 8, 9, 10, or more) nucleic acid molecules (e.g., vectors) and introduced into a cell. A "nucleic acid" is at least two nucleotides covalently linked together, and in some instances, may contain phosphodiester bonds (e.g., a phosphodiester "backbone"). A nucleic acid may be DNA, both genomic and/or cDNA, RNA or a hybrid, where the nucleic acid contains any combination of deoxyribonucleotides and ribonucleotides (e.g., artificial or natural), and any combination of bases, including uracil, adenine, thymine, cytosine, guanine, inosine, xanthine, hypoxanthine, isocytosine and isoguanine. Nucleic acids of the present disclosure may be produced using standard molecular biology methods (see, e.g., *Green and Sambrook, Molecular Cloning*, A Laboratory Manual, 2012, Cold Spring Harbor Press).

In some embodiments, nucleic acids are produced using GIBSON ASSEMBLY® Cloning (see, e.g., Gibson, D. G. et al. *Nature Methods,* 343-345, 2009; and Gibson, D. G. et al. *Nature Methods,* 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies.

In some embodiments, different genetic circuits of the cell state classifier are is delivered to a cell on one or more (e.g., 2, 3, 4, 5, 6, 7, 8, 9, 10, or more) vectors. A "vector" refers to a nucleic acid (e.g., DNA) used as a vehicle to artificially carry genetic material (e.g., an engineered nucleic acid) into a cell where, for example, it can be replicated and/or expressed. In some embodiments, a vector is an episomal vector (see, e.g., Van Craenenbroeck K. et al. *Eur. J. Biochem.* 267, 5665, 2000, incorporated by reference herein). A non-limiting example of a vector is a plasmid. Plasmids are double-stranded generally circular DNA sequences that are capable of automatically replicating in a host cell. Plasmid vectors typically contain an origin of replication that allows for semi-independent replication of the plasmid in the host and also the transgene insert. Plasmids may have more features, including, for example, a "multiple cloning site," which includes nucleotide overhangs for insertion of a nucleic acid insert, and multiple restriction enzyme consensus sites to either side of the insert. Another non-limiting example of a vector is a viral vector (e.g., retroviral, adenoviral, adeno-association, helper-dependent adenoviral systems, hybrid adenoviral systems, herpes simplex, pox virus, lentivirus, Epstein-Barr virus). In some embodiments, the viral vector is derived from an adeno-associated virus (AAV). In some embodiments, the viral vector is derived from an herpes simplex virus (HSV).

The nucleic acids or vectors containing the genetic circuits of the cell state classifier may be delivered to a cell by any methods known in the art for delivering nucleic acids. For example, for delivering nucleic acids to a prokaryotic cell, the methods include, without limitation, transformation, transduction, conjugation, and electroporation. For delivering nucleic acids to a eukaryotic cell, methods include, without limitation, transfection, electroporation, and using viral vectors.

Cells containing the cell state classifiers are also provided herein. A "cell" is the basic structural and functional unit of all known independently living organisms. It is the smallest unit of life that is classified as a living thing. Some organisms, such as most bacteria, are unicellular (consist of a single cell). Other organisms, such as humans, are multicellular.

In some embodiments, a cell for use in accordance with the present disclosure is a prokaryotic cell, which may comprise a cell envelope and a cytoplasmic region that contains the cell genome (DNA) and ribosomes and various sorts of inclusions. In some embodiments, the cell is a bacterial cell. As used herein, the term "bacteria" encompasses all variants of bacteria, for example, prokaryotic organisms and cyanobacteria. Bacteria are small (typical linear dimensions of around 1 micron), non-compartmentalized, with circular DNA and ribosomes of 70S. The term bacteria also includes bacterial subdivisions of Eubacteria and Archaebacteria. Eubacteria can be further subdivided into gram-positive and gram-negative Eubacteria, which depend upon a difference in cell wall structure. Also included herein are those classified based on gross morphology alone (e.g., cocci, bacilli). In some embodiments, the bacterial cells are gram-negative cells, and in some embodiments, the bacterial cells are gram-positive cells. Examples of bacterial cells that may be used in accordance with the invention include, without limitation, cells from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., Hemophilus spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Stremtomyces* spp. In some embodiments, the bacterial cells are from *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans, Bacteroides, cyanobacteria, Escherichia coli, Helobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus planta rum, Streptococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes, Streptomyces ghanaenis, Halobacterium* strain GRB, or *Halobaferax* sp. strain Aa2.2.

In some embodiments, a cell for use in accordance with the present disclosure is a eukaryotic cell, which comprises membrane-bound compartments in which specific metabolic activities take place, such as a nucleus. Examples of eukaryotic cells for use in accordance with the invention include, without limitation, mammalian cells, insect cells, yeast cells (e.g., *Saccharomyces cerevisiae*) and plant cells. In some embodiments, the eukaryotic cells are from a vertebrate animal. In some embodiments, the cell is a mammalian cell. In some embodiments, the cell is a human cell. In some embodiments, the cell is from a rodent, such as a mouse or a rat. Examples of vertebrate cells for use in accordance with the present disclosure include, without limitation, reproductive cells including sperm, ova and embryonic cells, and non-reproductive cells, including kidney, lung, spleen, lymphoid, cardiac, gastric, intestinal, pancreatic, muscle, bone, neural, brain and epithelial cells. Stem cells, including embryonic stem cells, can also be used.

In some embodiments, the cell is a diseased cell. A "diseased cell," as used herein, refers to a cell whose biological functionality is abnormal, compared to a non-diseased (normal) cell. In some embodiments, the diseased cell is a cancer cell.

Applications

The cell state classifier described herein may be used for a variety of applications. In some embodiments, the cell state classifier may be used for diagnostic purposes. For example, in some embodiments, the cell state classifier may be designed to detect the microRNA profile in a diseased cell (e.g., a cancer cell). As such, if an output signal is detected when such cell state classifier is delivered to a cell, the cell may be classified as a diseased cell (e.g., a cancer cell). For diagnostic purposes, the output molecules of the cell state classifier (e.g., the first or second cell state classifier) is typically a detectable molecule (e.g., a fluorescent protein or chemiluminescent protein). Depending on the cell type to be detected and the specific microRNA profile, in some embodiments, the expression of the first and/or second output molecule indicates a diseased cell. In some embodiments, the lack of expression of the output molecule indicates a diseased cell.

In another example, the cell state classifier is used for therapeutic purposes. For example, in some embodiments, the cell state classifier may be designed to detect the microRNA profile in a diseased cell (e.g., a cancer cell) and to produce an output molecule that is a therapeutic molecule (e.g., a therapeutic protein or RNA). Upon detecting of a matching microRNA profile in the diseased cell, the cell state classifier produces the therapeutic molecule, thus treating the disease. Such therapeutic methods are highly specific to the diseased cell and have low impact on healthy cells because the cell state classifier will not detect a matching microRNA profile in a healthy cell and thus will not produce the output molecule. Further, the therapeutic effect of the cell state classifier is long lasting. For example, the cell state classifier will continuing to produce the therapeutic molecule until the diseased cell no longer has a matching microRNA profile that fit the disease (e.g., cancer). Once therapeutic effects have taken place, the cell state classifier can sense the change in the microRNA profile (e.g., from cancer profile to normal profile) and stop the production of the therapeutic molecule.

For either diagnostic or treatment purposes, the cell may be in vitro (e.g., cultured cell), ex vivo (e.g., isolated from a subject), or in vivo in a subject. For in vivo applications, in some embodiments, the method comprises administering an effective amount of a composition comprising the cell state classifier described herein to a subject in need thereof. The composition can further comprise additional agents (e.g. for specific delivery, increasing half-life, or other therapeutic agents). In some embodiments, the composition further comprises a pharmaceutically acceptable carrier. The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. A "pharmaceutically acceptable carrier" is a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

Some examples of materials which can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as peptides and amino acids (23) serum component, such as serum albumin, HDL and LDL; (24) C2-C12 alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient," "carrier," "pharmaceutically acceptable carrier" or the like are used interchangeably herein.

An "effective amount" refers to the amount of the cell state classifier or composition comprising such required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a disorder. Alternatively, sustained continuous release formulations of agent may be appropriate. Various formulations and devices for achieving sustained release are known in the art.

An effective amount of the cell state classifier or composition comprising such agents may be administered repeatedly to a subject (e.g., 2, 3, 4, 5, 6, 7, 8, 9, 10 times or more). In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the agents used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the agent (such as the half-life of the agent, and other considerations well known in the art).

For the purpose of the present disclosure, the appropriate dosage of the cell state classifiers compositions as described herein will depend on the specific agent (or compositions thereof) employed, the formulation and route of administration, the type and severity of the disorder, previous therapy, the subject's clinical history and response to the agents, and the discretion of the attending physician. Typically the clinician will administer an agent until a dosage is reached that achieves the desired result. Administration can be continuous or intermittent, depending, for example, upon the recipient's physiological condition, and other factors known to skilled practitioners. The administration of an agent may be essentially continuous over a preselected period of time or may be in a series of spaced dose, e.g., either before, during, or after developing a disorder.

A "subject" refers to human and non-human animals, such as apes, monkeys, horses, cattle, sheep, goats, dogs, cats, rabbits, guinea pigs, rats, and mice. In one embodiment, the subject is human. In some embodiments, the subject is an experimental animal or animal substitute as a disease model. A "subject in need thereof" refers to a subject who has or is at risk of a disease or disorder (e.g., cancer).

The cell state classifiers of the present disclosure may be delivered to a subject (e.g., a mammalian subject, such as a human subject) by any in vivo delivery method known in the art. For example, engineered nucleic acids may be delivered intravenously. In some embodiments, engineered nucleic acids are delivered in a delivery vehicle (e.g., non-liposomal nanoparticle or liposome). In some embodiments, the cell state classifiers are delivered systemically to a subject having a cancer or other disease and produces a therapeutic molecule specifically in cancer cells or diseased cells of the subject. In some embodiments, the cell state classifiers are delivered to a site of the disease or disorder (e.g., site of cancer).

Non-limiting examples of cancers that may be treated using the cell state classifiers and methods described herein include: premalignant neoplasms, malignant tumors, metastases, or any disease or disorder characterized by uncontrolled cell growth such that it would be considered cancerous or precancerous. The cancer may be a primary or metastatic cancer. Cancers include, but are not limited to, ocular cancer, biliary tract cancer, bladder cancer, pleura cancer, stomach cancer, ovary cancer, meninges cancer, kidney cancer, brain cancer including glioblastomas and medulloblastomas, breast cancer, cervical cancer, choriocarcinoma, colon cancer, endometrial cancer, esophageal cancer, gastric cancer, hematological neoplasms including acute lymphocytic and myelogenous leukemia, multiple myeloma, AIDS-associated leukemias and adult T-cell leukemia lymphoma, intraepithelial neoplasms including Bowen's disease and Paget's disease, liver cancer, lung cancer, lymphomas including Hodgkin's disease and lymphocytic lymphomas, neuroblastomas, oral cancer including squamous cell carcinoma, ovarian cancer including those arising from epithelial cells, stromal cells, germ cells and mesenchymal cells, pancreatic cancer, prostate cancer, rectal cancer, sarcomas including leiomyosarcoma, rhabdomyosarcoma, liposarcoma, fibrosarcoma, and osteosarcoma, skin cancer including melanoma, Kaposi's sarcoma, basocellular cancer, and squamous cell cancer, testicular cancer including germinal tumors such as seminoma, non-seminoma, teratomas, choriocarcinomas, stromal tumors and germ cell tumors, thyroid cancer including thyroid adenocarcinoma and medullar carcinoma, and renal cancer including adenocarcinoma and Wilms' tumor. Commonly encountered cancers include breast, prostate, lung, ovarian, colorectal, and brain cancer. In some embodiments, the tumor is a melanoma, carcinoma, sarcoma, or lymphoma.

EXAMPLES

The ability to classify individual cell types in a mixed tissue or during cellular differentiation is a powerful tool for synthetic biologists. This can be achieved using unique microRNA (miRNA) profiles, which are unique to different cell types or even different states of a single cell type. Genetic classifiers have been developed to monitor the levels of various miRNAs, allowing gene circuits to respond to miRNAs with "low" and "high" activity in the cell (Xie et al., 2011). Such miRNA classifiers can be used to activate therapeutic genes in specific cells, identify or eliminate cells in a diseased state, or monitor differentiation in a tissue.

MiRNA classifiers rely on two different sensor topologies to function (Xie et al., 2011). "Low" miRNA sensors are simpler, with repeated target sites for multiple miRNAs in cis on the mRNA for the protein of interest (which may be a fluorescent protein, a toxin, a transcription factor, etc.) Each of these miRNAs is expected to have low activity in the cells of interest. If the miRNAs are higher than expected, they will lead to repression of the target mRNA. "High" miRNA sensors are more complicated. Instead of directly acting upon the target mRNA, individual miRNA target sites are encoded in the mRNA of transcriptional repressor proteins. When the miRNA activity is high, as expected, the repressor is suppressed and the target mRNA is expressed. When the miRNA activity is lower than expected, the repressor is expressed, and the target mRNA is repressed. Additionally, an RNA-regulation-based high miRNA sensor has been described (Wroblewska et al., 2015). This involves using the RNA binding protein L7Ae to repress translation of the target mRNA, rather than repressing transcription.

In order to improve on the miRNA classifier design, two new technologies have been developed. First, a new "high" miRNA sensor design to tightly regulate a DNA-launched self-amplifying RNA (DREP) to express genes of interest at very high levels was developed. Second, a strategy to express all components of a miRNA classifier from a single initial RNA transcript was developed.

Figure 1C:
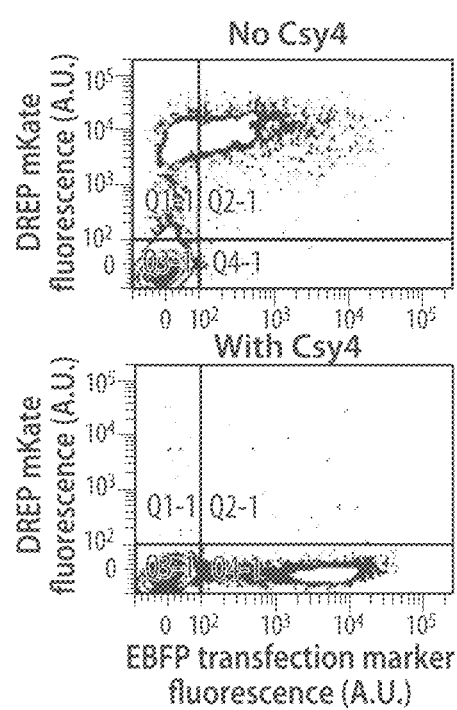

Example 1: Csy4-Based High miRNA Sensor for Regulation of High Expressing DNA-Launched Self-Amplifying RNAs The alpha-virus-derived RNA replicon is a self-amplifying RNA that rapidly reaches high expression in the cell (Wroblewska et al., 2015). While the replicon can be transfected directly into cells, it can also be launched from a DNA gene. This DNA-launched replicon (DREP) has the replicon, including non-structural proteins and subgenomic payloads, encoded in DNA under control of a transcriptional promoter. DREP produces high expression of payload genes even at low transfection efficiencies (FIG. 1A), which is useful for many applications. DREP expression can be regulated both by transcriptional promoters (FIG. 1B) and by the CRISPR-associated endoribonuclease Csy4 (FIG. 1C). Both methods provide tight control of DREP expression, allowing for tight "off" states and high "on" states.

A miRNA classifier was designed to regulate DREP expression (FIG. 2). DREP is activated by constitutively expressed Gal4-VP16, and repressed by a tTA-regulated Csy4 (or versions of Csy4 with various degradation domains to further modulate its strength). A "low" miRNA sensor was incorporated into Gal4-VP16 and DREP, with binding sites for miRNAs in the 5' and 3' UTRs of Gal4-VP16 and the replicon payload. For the "high" sensor, miRNA sites are located in the UTRs of Csy4 and tTA.

If the "low" miRNAs are low activity, and the "high" miRNAs are high activity, the payload will be activated. Gal4-VP16 will be expressed to drive transcription of DREP, which will self-amplify and express the payload. The repressor Csy4 will be knocked down by miRNAs, as will tTA, which will further drive down Csy4 levels.

On the other hand, if the "low" miRNAs are actually high, the payload will be knocked down. Similarly, Gal4-VP16 will be knocked down, reducing the amount of DREP produced. Furthermore, if the "high" miRNAs are actually low, Csy4 will be activated and will repress DREP.

Example 2: miRNA Classifier Circuit Expressed from a Single RNA Transcript

Expressing both the low and high miRNA sensors from a single RNA transcript can both limit the amount of parts to be transfected into the cell, and so help reduce epigenetic silencing issues for integrated circuits. The design described herein incorporates the RNA based classifier (Wroblewska et al., 2015) into a single RNA transcript (FIG. 3A). To allow for independent regulation of the gene of interest and the repressor, the mRNA was split using either ribozymes or endoribonucleases (such as Csy4), and protecting the newly formed ends with a MALAT1 triplex structure at the newly formed 3' end and a poliovirus cloverleaf at the new 5' end (Nissim et al., 2014; Kempf and Barton, 2008). The downstream open reading from (ORF) is translated from an IRES. The entire transcript is under control of a constitutive promoter. After transcription, the mRNAs are split, allowing for independent regulation of each ORF.

A low miRNA sensor was incorporated into the payload in the first ORF (FIG. 3A). If these miRNAs are high, the target mRNA will be knocked down. For the high sensor, an L7Ae protein expressed from the second ORF represses the payload by binding to a K-Turn motif upstream of the first ORF. L7Ae is regulated by a "high" miRNA sensor. If this miRNA is low, L7Ae will be expressed, repressing the protein of interest. Additional high sensors can be added by incorporating more splitters, and can use either additional copies of the same repressor (FIG. 3B) or alternative repressors, such as Cse3, TetR, or MS2-CNOT7 (FIG. 3C).

REFERENCES

1. Kempf, B. J. and Barton, D. J. (2008) Poly(rC) binding proteins and the 5' cloverleaf of uncapped poliovirus mRNA Function during de novo assembly of polysomes. *Journal of Virology*. 82: 5835-5846
2. Nissim, L. et al. (2014) Multiplexed and programmable regulation of gene networks with an integrated RNA and CRISPR/Cas toolkit in human cells. *Molecular Cell*. 54: 1-13
3. Wroblewska, L. et al. (2015) Mammalian synthetic circuits with RNA binding proteins for RNA-only delivery. *Nature Biotechnology*. 33: 839-841
4. Xie, Z., et al. (2011) Multi-input RNAi-based logic circuit for identification of specific cancer cells. *Science*. 333: 1307-1311

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A cell state classifier, comprising:
   (i) a first sensor circuit comprising a promoter operably linked to a nucleotide sequence encoding a first activator and one or more target sites for a first microRNA;
   (ii) a second sensor circuit comprising:
      (a) a first part comprising a promoter operably linked to a nucleotide sequence encoding a second activator, and one or more target sites for a second microRNA, wherein the second microRNA is different from the first microRNA; and
      (b) a second part comprising a promoter that is activated by the second activator, operably linked to a nucleotide sequence encoding an endoribonuclease, and one or more target sites for the second microRNA; and
   (iii) a signal circuit comprising an activatable promoter that is activated by the first activator, operably linked to a nucleotide encoding a self-amplifying RNA comprising a subgenomic promoter operably linked to a nucleotide sequence encoding an output molecule, one or more target sites for the first microRNA, and a recognition site for the endoribonuclease of (ii)(b).

2. The cell state classifier of claim 1, wherein the endoribonuclease belongs to the CRISPR-associated endoribonuclease 6 (Cas6) family.

3. The cell state classifier of claim 2, wherein the endoribonuclease is fused to a degradation domain.

4. The cell state classifier of claim 1, wherein the self-amplifying RNA is derived from a virus.

5. An isolated cell comprising the cell state classifier of claim 1.

6. A method comprising maintaining the cell of claim 5 in a culture.

7. A method comprising delivering the cell state classifier of claim 1 to a cell and detecting an output molecule.

8. A method of treating a disease or disorder comprising delivering the cell having the disease or disorder state classifier of claim 1 to a cell, wherein the output molecule is a therapeutic molecule that is effective for treating the disease or disorder.

9. A method of diagnosing a disease or disorder comprising delivering the cell, and diagnosing a disease or disorder in the cell state classifier of claim 1 to a cell.

10. A method of treating a disease or disorder comprising administering an effective amount of a composition comprising the cell state classifier of claim 1 to a subject in need thereof, wherein the output molecule is a therapeutic molecule that is effective for treating the disease or disorder.

11. A method of diagnosing a disease or disorder comprising administering an effective amount of a composition comprising the cell state classifier of claim 1 to a subject in need thereof, and detecting the output molecule.

* * * * *

UNITED STATES PATENT AND TRADEMARK OFFICE
CERTIFICATE OF CORRECTION

PATENT NO. : 11,339,395 B2
APPLICATION NO. : 16/528697
DATED : May 24, 2022
INVENTOR(S) : Ron Weiss et al.

It is certified that error appears in the above-identified patent and that said Letters Patent is hereby corrected as shown below:

In the Claims

Claim 8, at Column 86, Lines 45-49:
"A method of treating a disease or disorder comprising delivering the cell having the disease or disorder state classifier of claim 1 to a cell, wherein the output molecule is a therapeutic molecule that is effective for treating the disease or disorder."
Should read:
-- A method of treating a disease or disorder comprising delivering the cell state classifier of claim 1 to a cell having the disease or disorder, wherein the output molecule is a therapeutic molecule that is effective for treating the disease or disorder. --

Claim 9, at Column 86, Lines 50-52:
"A method of diagnosing a disease or disorder comprising delivering the cell, and diagnosing a disease or disorder in the cell state classifier of claim 1 to a cell."
Should read:
-- A method of diagnosing a disease or disorder comprising delivering the cell state classifier of claim 1 to a cell, and diagnosing a disease or disorder in the cell. --

Signed and Sealed this
Eighteenth Day of October, 2022

Katherine Kelly Vidal
*Director of the United States Patent and Trademark Office*